US008501924B2

(12) United States Patent
Falini et al.

(10) Patent No.: US 8,501,924 B2
(45) Date of Patent: Aug. 6, 2013

(54) NUCLEOPHOSMIN PROTEIN (NPM) MUTANTS, CORRESPONDING GENE SEQUENCES AND USES THEREOF

(76) Inventors: Brunangelo Falini, Perugia (IT); Cristina Mecucci, Perugia (IT)

( * ) Notice: Subject to any disclaimer, the term of this patent is extended or adjusted under 35 U.S.C. 154(b) by 717 days.

(21) Appl. No.: 11/982,679

(22) Filed: Nov. 2, 2007

(65) Prior Publication Data
US 2008/0299560 A1 Dec. 4, 2008

Related U.S. Application Data

(62) Division of application No. 11/666,542, filed as application No. PCT/IT2005/000643 on Oct. 28, 2005, now Pat. No. 8,222,370.

(30) Foreign Application Priority Data

Oct. 29, 2004 (IT) .............................. RM2004A0534

(51) Int. Cl.
*C07H 21/04* (2006.01)
*C12Q 1/68* (2006.01)

(52) U.S. Cl.
USPC ........................................ 536/23.5; 435/6.12

(58) Field of Classification Search
None
See application file for complete search history.

(56) References Cited

U.S. PATENT DOCUMENTS
6,174,674 B1 1/2001 Morris et al. ..................... 436/6

FOREIGN PATENT DOCUMENTS
WO WO 02/06471 1/2002
WO WO 2004/005517 7/2004
WO WO 2004/096142 11/2004

OTHER PUBLICATIONS

Falini eta l, 2007, Blood, 109: 874-885.*
Bowie (Science, 1990, 257:1306-1310).*
Burgess et al ( J of Cell Bio. 111:2129-2138, 1990).*
Lazar et al (Molecular and Cellular Biology, 1988, 8:1247-1252).*
Wen et al (Cell, 1995, 82:463-473, IDS).*
Falini et al, New England J of Medicine, 2005, 352:254-266, IDS.*
Bertwistle, et al., Mol Cell Biol 2004; 24:985-996.
Bischof, et al., Mol Cell Biol 1997; 17:2312-2325.
Borer, et al., Cell 1989; 56:379-390.
Bullinger, et al., New England Journal of Medicine 2004; 350:1605-1616.
Byrd, et al., Blood 2002; 100:4325-4336.
Carnicer, et al., Leuk Res 2004; 28:19-23.
Chang, et al., Biochem J 1998; 329:539-544.
Christiansen, et al., Leukemia 2001;15:1848-1851.
Cimino, et al., Cancer Res 1995; 55:1625-1628.
Colombo, et al., Nat Cell Biol 2002; 4:529-533.
Cordell, et al., Blood 1999; 93:632-642.
Cordell, et al., J Histochem Cytochem 1984; 32:219-229.
Crescenzi et al., Cancer Genet Cytogenet 2000;120:25-29.
Dohner, et al., Blood (online Jul. 28, 2005).
Downward, et al., BMJ 2004; 328:1245-1248.
Dumbar, et al., Biochemistry 1989; 28:9495-9501.
Engelhardt, et al., Leukemia 2002; 16:1603-1608.
Falini et al., Blood 1999; 94:3509-3515.
Falini, et al., N Engl J Med 2005; 352:254-266.
Falini, et al., Blood 1999; 93:2697-2706.
Falini, et al., Blood 2002; 99:409-426.
Falini, et al., The New England Journal of Medicine 2005; 352:254-266.
Falini, et al., Blood 2006; (entire document).
Frohling, et al., Blood 2002; 100:4372-4380.
Gabert, et al., Leukemia 2003; 17:1013-1034.
Gabert,et al., Leukemia 2003; 17:2318-2357.
GenBank Accession No. AY740634.
GenBank Accession No. AY740635.
GenBank Accession No. AY740636.
GenBank Accession No. AY740637.
GenBank Accession No. AY740638.
GenBank Accession No. AY740639.
GenBank Accession No. NM002520.
Goodell, et al., Nat Med 1997; 3:1337-1345.
Gorello, et al., Leukemia 2006; 1-6 (entire document).
Grimwade, et al., Blood 1998; 92:2322-2333.
Grisendi, et al., Nature 2005; 437:147-153.
Hingorani, et al., J Biol Chem 2000; 275:24451-24457.
Horn, et al., Nature 2004; 427:110-111.
Kurki, et al., Cancer Cell 2004; 5:465-475.
Morris, et al., Science 1994; 263:1281-1284.
Nishimura, et al., Biosci Biotechnol Biochem 2002; 66:2239-2242.
Noguera et al., Leukemia 2002; 16:2185-2189.
Okuda, et al., Cell 2000; 103:127-140.
Pabst, et al. Nat Genet 2001; 27:263-270.
Quentmeier, Leukemia 2005; 19:1760-1767.
Redner, et al. Blood 1996; 87:882-886.
Schnittger, et al., Blood 2002; 100:59-66.
Schnittger, et al., Blood (online Aug. 2, 2005).
Schreiber, et al., Nucleic Acids Res. 1989; 17:6419.
Shuker, et al., Science 1996 ; 274 :1531-1534.
Soekarman, et al., Blood 1992; 79:2990-2997.
Steudel, et al., Genes Chromosomes & Cancer 2003; 37:237-251.
Stocks, et al., Drug Discov Today 2004; 9:960-966.
Valk, et al., New England Journal of Medicine 2004; 350:1617-1628.
Van der Velden, et al., Leukemia 2003; 17:1013-1034.
Van Dongen, et al., Leukemia 1999; 13:1901-1928.
Verhaak, et al., Blood (online Aug. 18, 2005).
Wang, et al., Nat Cell Biol 2005; 7:823-830.
Yoneda-Kato, et al., Oncogene 1996; 12:265-275.
European Search Report for EP 07 02 1463, dated Jun. 4, 2008.

(Continued)

Primary Examiner — Laura B Goddard
(74) Attorney, Agent, or Firm — Patentique PLLC

(57) ABSTRACT

The invention relates to new nucleophosmin protein (NPM) mutants, corresponding gene sequences and relative uses thereof for diagnosis, monitoring of minimal residual disease; prognostic evaluation and therapy of the acute myeloid leukaemia (AML).

13 Claims, 17 Drawing Sheets
(8 of 17 Drawing Sheet(s) Filed in Color)

OTHER PUBLICATIONS

International Search Report for PCT/IT/2005/000634, mailed Sep. 8, 2006.

Cazzaniga et al., "Nucleophosmin mutations in childhood acute myelogenous leukemia with normal karyotype", *Blood*, 106(4):1419-1422 (2005).

Suzuki et al., "Clinical characteristics and prognostic implications of *NPM1* mutations in acute myeloid leukemia", *Neoplasia*, 106(8):2854-2861 (2005).

Wen, et al., Identification of a Signal for Rapid Export of Proteins from the Nucleus; *Cell*, 82:463-473 (1995).

* cited by examiner

Fig. 6

| | List of exon-12 NPM1 mutations identified in AML patients | | | | | | Predicted protein (C-terminus) | (%) | IH |
|---|---|---|---|---|---|---|---|---|---|
| Wild-type* | gaccaagaggctattcaagatctct | | | g | gcag | ggagg | aagtctctttaagaaaatag | 286-DLQWRKSL | | Nuclear |
| Mutation A | gaccaagaggctattcaagatctct | | TCTG | g | gcag | ggagg | aagtctctttaagaaaatag | 286-DLCLAVEEVSLRK | 81 | cit |
| Mutation B | gaccaagaggctattcaagatctct | | CATG | g | gcag | ggagg | aagtctctttaagaaaatag | 286-DLCMAVEEVSLRK | 7 | cit |
| Mutation C | gaccaagaggctattcaagatctct | | CGTG | g | gcag | ggagg | aagtctctttaagaaaatag | 286-DLCVAVEEVSLRK | <1 | cit |
| Mutation D | gaccaagaggctattcaagatctct | | CCTG | g | gcag | ggagg | aagtctctttaagaaaatag | 286-DLCLAVEEVSLRK | 5 | cit |
| Mutation E | gaccaagaggctattcaagatctct | | | g | gcag | ggagg | aagtctctttaagaaaatag CTCTTGCCC | 286-DLMQSLAQVSLRK | <1 | cit |
| Mutation F | gaccaagaggctattcaagatctct | | | g | gcag | ggagg | aagtctctttaagaaaatag CCCTGGAGA | 286-DLMQSLEKVSLRK | <1 | cit |
| Mutation G | gaccaagaggctattcaagatctct | | | g | gcag | | aagtctctttaagaaaatag GCTTCGCCG | 286-DLMQCFRQVSLRK | | nd |
| Mutation H | gaccaagaggctattcaagatctct | | | g | gcag | | aagtctctttaagaaaatag GTTTTTCAA | 286-DLMQCFSKVSLRK | | nd |
| Mutation I | gaccaagaggctattcaagatctct | | | g | gcag | | aagtctctttaagaaaatag CCCTCGCCC | 286-DLMQSLAQVSLRK | | nd |
| Mutation J | gaccaagaggctattcaagatctct | | | g | gcag | | aagtctctttaagaaaatag CTCTTTCTA | 286-DLMQSLSKVSLRK | <1 | cit |
| Mutation K | gaccaagaggctattcaagatctct | CCCG | | g | gcag | ggagg | aagtctctttaagaaaatag | 286-DLSRAVEEVSLRK | <1 | cit |
| Mutation L | gaccaagaggctattcaagatctct | | | g | gcag | | aagtctctttaagaaaatag CCCTTTCCA | 286-DLMQSLSRVSLRK | <1 | cit |
| Mutation M | gaccaagaggctattcaagatctct | | TAGC | g | gcag | ggagg | aagtctctttaagaaaatag | 286-DLCTAVEEVSLRK | <1 | cit |
| Mutation N | gaccaagaggctattcaagatctct | CCCA | | g | gcag | ggagg | aagtctctttaagaaaatag | 286-DLSQAVEEVSLRK | <1 | nd |
| Mutation O | gaccaagaggctattcaagatctct | | CCAC | g | gcag | ggagg | aagtctctttaagaaaatag | 286-DLCHAVEEVSLRK | <1 | cit |
| Mutation P | gaccaagaggctattcaagatctct | | | g | gcag | ggagg | aagtctctttaagaaaatag CGTTTCC | 286-DLMQRFQEVSLRK | <1 | nd |
| Mutation Q | gaccaagaggctattcaagatctct | | TACCTTCC | g | gcag | ggagg | aagtctctttaagaaaatag | 286-DLCTFLEEVSLRK | <1 | nd |
| Mutation R | gaccaagaggctattcaagatctct | | | g | gcag | ggagg | aagtctctttaagaaaatag AGGA | 286-DLMQRMEEVSLRK | <1 | nd |
| Mutation Gm | gaccaagaggctattcaagatctct | | CAGG | g | gcag | ggagg | aagtctctttaagaaaatag | 286-DLMQSMEEVSLRK | | nd |
| Mutation Km | gaccaagaggctattcaagatctct | | CCGG | g | gcag | ggagg | aagtctctttaagaaaatag | 286-DLCLAHAVEEVSLRK | | nd |
| Mutation Lm | gaccaagaggctattcaagatctct | | CCGCGG | ag | gcag | ggagg | aagtctctttaagaaaatag | 286-DLCLRGVEEVSLRK | | nd |
| Mutation Nm | gaccaagaggctattcaagatctct | | CCAG | g | gcag | ggagg | aagtctctttaagaaaatag | 286-DLCQAVEEVSLRK | | nd |
| Mutation Om | gaccaagaggctattcaagatctct | | TTTG | g | gcag | ggagg | aagtctctttaagaaaatag | 286-DLCLAVEEVSLRK | | nd |
| Mutation Qm | gaccaagaggctattcaagatctct | | TCGG | g | gcag | ggagg | aagtctctttaagaaaatag | 286-DLCRAVEEVSLRK | | nd |
| Mutation 1 | gaccaagaggctattcaagatctct | | CAGG | g | gcag | ggagg | aagtctctttaagaaaatag TCCA | 286-DLMQSMEEVSLRK | | nd |
| Mutation 3 | gaccaagaggctattcaagatctct | | TCAT | g | gcag | ggagg | aagtctctttaagaaaatag | 286-DLCHAVEEVSLRK | | nd |
| Mutation 4 | gaccaagaggctattcaagatctct | | CTTG | g | gcag | ggagg | aagtctctttaagaaaatag | 286-DLCLAVEEVSLRK | | nd |
| Mutation 6 | gaccaagaggctattcaagatctct | | AGATTTCTTAAATC | g | gca | ggagg | gtccctttaagaaaatag | 286-DLMQQFLNLFKKIV | | nd |
| Mutation 7 | accaagaggctattcaagatctct | ATGC | | g | gcag | ggagg | aagtctctttaagaaaatag | 286-DLCLAVEEVSLRK | | nd |
| Mutation 12 | gaccaagaggctattcaagatctct | | GCCC | g | gcag | ggagg | aagtctctttaagaaaatag | 286-DLCAAVEEVSLRK | | nd |
| Mutation 13 | gaccaagaggctattcaagatctct | | TAAG | g | gcag | ggagg | aagtctctttaagaaaatag | 286-DLCKAVEEVSLRK | | nd |
| Mutation 10 | gaccaagaggctattcaagatctct | | | g | gcag | | aagtctctttaagaaaatag CTGCTCCC | 286-DLMQCCSQVSLRK | | nd |
| Mutation 14 | gaccaagaggctattcaagatctct | | | g | gcag | | aagtctctttaagaaaatag TATTTCCC | 285-DLMQCCSQVSLRK | | nd |
| Mutation G' | gaccaagaggctattcaagatctct | | TTTG | g | gcag | ggagg | aagtctctttaagaaaatag | 286-DLCLAVEEVSLRK | | nd |
| Mutation H' | gaccaagaggctattcaagatctct | | CTTG | g | gcag | ggagg | aagtctctttaagaaaatag | 286-DLCLAVEEVSLRK | | nd |
| Mutation I' | gaccaagaggctattcaagatctct | | TAAG | g | gcag | ggagg | aagtctctttaagaaaatag | 286-DLCKAVEEVSLRK | | nd |
| Mutation J' | gaccaagaggctattcaagatctct | | TATG | g | gcag | ggagg | aagtctctttaagaaaatag | 286-DLCMAVEEVSLRK | | nd |
| Mutation I* | gaccaagaggctattcaagatctct | | CAGA | g | gcag | ggagg | aagtctctttaagaaaatag | 286-DLCRAVEEVSLRK | | nd |

Bold: amino acids part of the NES motif. Underlined: tryptophan residues

Fig. 7
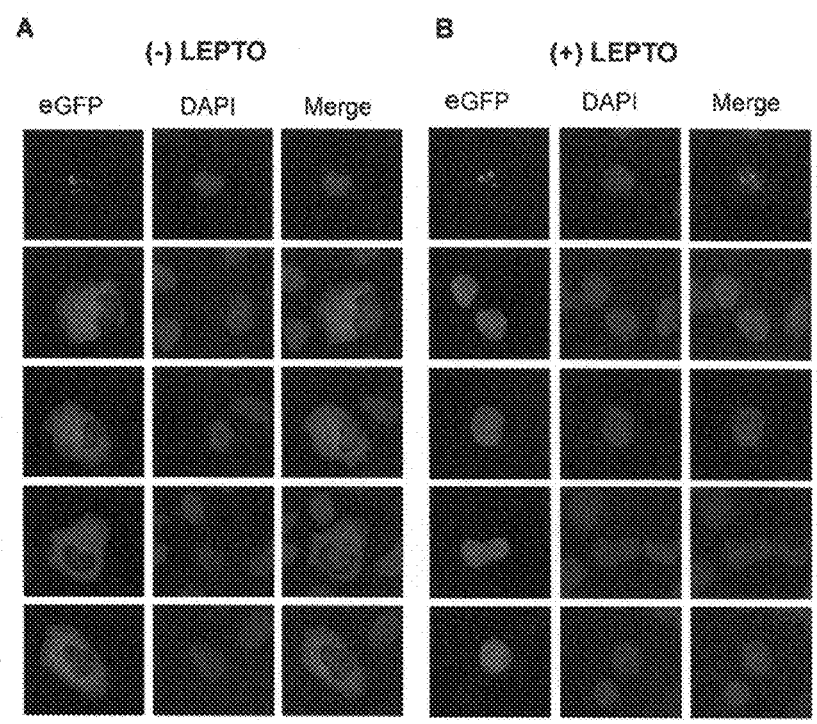
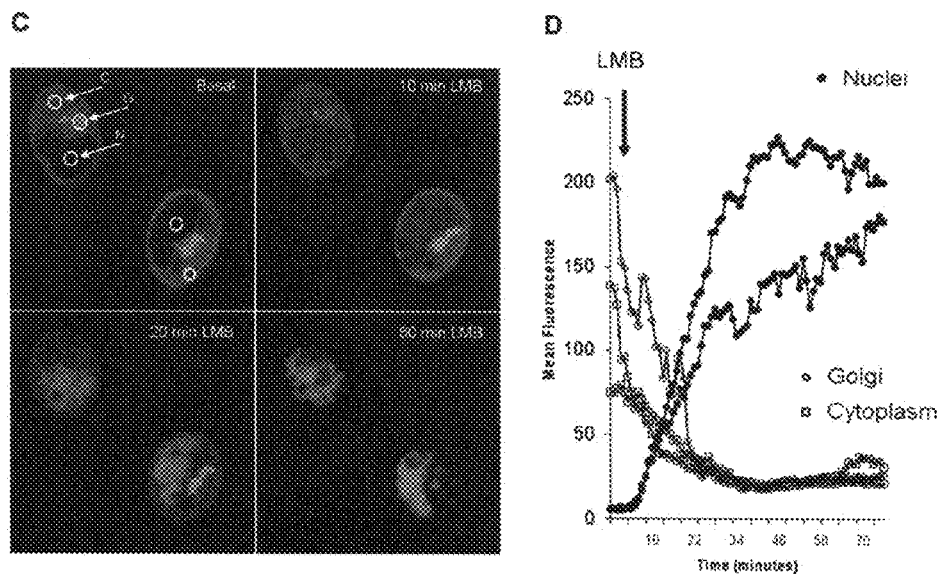
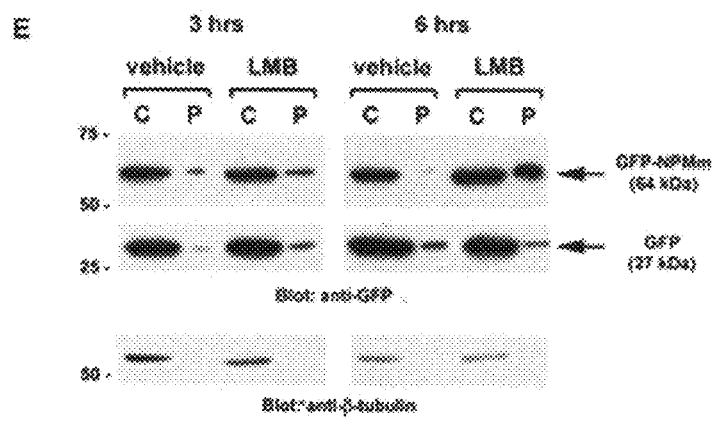

NUCLEOPHOSMIN PROTEIN (NPM) MUTANTS, CORRESPONDING GENE SEQUENCES AND USES THEREOF

CROSS-REFERENCE TO RELATED APPLICATIONS

This application is a divisional of U.S. application Ser. No. 11/666,542 filed Jan. 28, 2009 now U.S. Pat. No. 8,222,370, a national stage application filed under 35 U.S.C. §371, of International Application No. PCT/IT2005/000643 filed on Oct. 28, 2005, which claims the benefits of International Application No. RM2004A000534 filed on Oct. 29, 2004. The entire teachings of these applications are incorporated herein by reference.

INCORPORATION-BY-REFERENCE OF SEQUENCE LISTING

The contents of the text file named "29480508DIVSeqList.txt", which was created on Sep. 8, 2010 and is 19 KB in size, are hereby incorporated by reference in their entirety.

DESCRIPTION

The present invention refers to new nucleophosmin protein mutants, corresponding gene sequences and diagnosis use thereof, monitoring of the minimal residual disease, prognostic evaluation and therapy of the acute myeloid leukaemia (LAM).

More particularly, the invention refers to new mutants of the cytoplasmic nucleophosmin protein (NPM) and corresponding gene sequences and use thereof as markers for the diagnosis, prognosis and therapy of the acute myeloid leukaemia with normal karyotype.

The primary acute myeloid leukaemia, the more common leukaemic form in adults, is a disease originated from the bone marrow, more frequently from a pluripotent or multipotent stem cell, already "committed" for the myelopoiesis. The neoplastic transformation modifies the mechanisms regulating the proliferation and differentiation of the stem cell by preventing the maturation of its progeny. The consequence of this event is an accumulation, mainly in the bone marrow and then in the peripheral blood and in other organs and tissues, of leukaemic cells (or blastic) that proliferate autonomously.

To date, LAMs are divided into different prognostic groups based on cytogenetic analyses and molecular biology, in order to program the best treatment. Currently, the LAM therapy primarily is based on the sequential administration of different active chemotherapeutic drugs against the leukaemic cells.

There are different steps in the treatment of LAMs. The first step, named induction therapy, aims to destroy the most part of the leukaemic cells with the objective to lead the patients to the attainment of the so-called complete hematological remission, namely disappearance of the leukaemic cells with normalization of the peripheral and medullary hematological data. The destruction of the leukaemic cells remaining after this first step of therapy (so-called minimal residual disease) can be achieved through the continuation of the chemotherapy (maintenance or intensification or re-induction), followed or not by autologous or allogenic transplant (according to the presence or absence of negative prognostic factors and availability of a donor). Unfortunately, because of the aggressiveness of these malignant tumours, the treatment is decisive only for 30% of the patients. Three are main usable approaches in order to improve the diagnosis and survival of the LAM affected patients: i) providing rapid and specific diagnostic tests in order to achieve a more accurate diagnosis and be able in monitoring the so-called "minimal residual disease"; ii) identification of biological prognostic factors that allow to stratify the therapeutic treatment according to "risk categories" and iii) development of new more targeting therapy forms that allow to interfere with the neoplastic transformation mechanisms induced by some genetic lesions.

Some of these objectives have been pursued in some LAM subtypes, as those with the translocation t (8;21) or inv (16), which can be identified/monitored with extreme accuracy using cytogenetic techniques/FISH or RT-PCR, and show a prognosis better than other forms of leukaemia. Even, in some LAM subtypes as the promyelocytic leukaemia with translocation (15; 17), the employment, in combination with the chemotherapy and the trans-retinoic acid or ATRA (an agent that directly acts on the genetic lesion) has led to an evident improvement in the survival of these patients.

Nevertheless these diagnostic/therapeutic improvements concern only a minority of LAMs. In fact a major part of LAM, about 40% of the cases, in the cytogenetic analysis show a normal karyotype (Grimwade et al., 1998) and represents clinically and biologically an heterogeneous category (Grimwade et al., 1998; Schnittger et al., 2002; Byrd et al, 2002).

The analysis of LAM gene expression with normal karyotype has been proposed as means for characterizing different prognosis subgroups (Bullinger et al, 2004; Valk et al, 2004), but it has not allowed to identify genetic lesions specifically associated with the normal karyotype. Unique genetic lesions till now associated with the normal karyotype map at level of FLT3 (Schnittger et al., 2002; Frohling et al., 2002), CEBPα (Pabst et al., 2001), and MLL (Steudel of to the, 2003) genes. Nevertheless, they cannot be considered normal karyotype-specific because they are present also in cases of LAM with greater chromosomal translocations (Carnicer et al., 2004) besides in the acute secondary myeloid leukaemia (Christiansen et al., 2001).

Therefore, up to now, there are not diagnostic/prognostic assays or molecular markers, which allow to detect and discriminate specifically the primary normal karyotype LAMs, whose characterization and classification is still based on fallacious morphological criterions. In addition, the ignorance about the genetic lesion represents an impediment for the monitoring of the minimal residual disease (with relevant difficulty in the therapeutic choices) and to the potential development of new forms of molecular therapy for this category of LAM.

From the above it is clear the need to provide new diagnostic and prognostic markers for the primary acute myeloid leukaemia with normal karyotype, and new molecular targets for the specific therapy of this subtype of leukaemia.

The authors of the present invention have now identified mutants of the nucleophosmin gene (NPM) and nucleophosmin protein codified from the same, specifically associated to normal karyotype LAM.

The nucleophosmin (NPM) is a protein largely restricted at the nucleolus (Cordell et al., 1999) that acts as shuttle from the nucleus to cytoplasm (Borer et al., 1989). It is a "chaperon" molecule (Dumbar et al., 1989), probably involved in the prevention of the aggregation of the proteins in the nucleolus and regulation of the assemblage and transport of the pre-ribosomal structures through the nuclear membrane. It is also a target of CDK2/ciclin E in the duplication of the centrosome (Okuda et al., 2000) and is involved in the regulation of the tumour suppression mechanism mediated by Arf-p53

(Bertwistle et al., 2004; Colombo et al., 2002; Kurki et al., 2004). In the murine model ("knock-out" mouse), NPM gene seems to play a fundamental role in the regulation of the haemopoiesis (Grisendi et al., 2005).

The NPM gene is involved in the chromosomal translocations of leukaemias and lymphomas resulting in the formation of fusion proteins, such as, for example, NPM-ALK (Morris et al., 1994), NPM RARα (Redner et al, 1996), and NPM-MLF 1 (Yoneda-Kato et al., 1996), that preserve only the N-terminal region of NPM molecule (Falini et al., 1999; Falini et al., 2002). The nucleophosmin is supposed to contribute to oncogenesis by activating the oncogenic potential of the fusion partner (ALK, MLF1, RARα (Bischof et al, 1997).

Since NPM is presumed to have a role in the tumour suppression mediated by Arf/p53, the physiological traffic alterations from the nucleus to the cytoplasm could be critical during the transformation. Alterations in the sub-cellular distribution of NPM and/or fusion proteins containing NPM can be revealed by immuno-histochemistry studies. For example, in the so-called ALK positive lymphomas with t(2;5) (Falini et al., 1999) and acute leukaemia with t(3;5) is observed a cytoplasmic delocalization of NPM protein (Falini et al., 1999; Falini et al., 2002) with respect to the expected nucleolus location of the same NPM (Cordell et al., 1999). This find is due to the reactivity of the anti-NPM monoclonal antibody with NPM-ALK fusion protein [the product of the t(2;5)] or NPM-MLF1 [the product of the t(2;5)] or NPM-MLF1 [the product of the t(3;5)] and/or with the NPM protein dislocated in the cytoplasm probably through formation of heterodimers with NPM-MLF1.

The authors of the present invention have now shown that about a third of LAMs in adults at the immunohistochemical examination shows an aberrant cytoplasmic distribution of NPM protein (NPMc+) (normally nucleus-restricted) and that such immunohistochemical find is correlated to the presence in the leukaemic cells of specific mutations at level of the eson 12 of the NPM gene (GenBank NM_002520), in the portion encoding for the C-terminal structure of NPM protein (GenBank NP_002511).

The acute leukaemia expressing NPM protein mutants and corresponding gene sequences, named by the authors LAM NPMc+ (Falini et al., 2005), represents a well-distinct entity that is characterized by wide morphological spectrum, normal karyotype, elevated frequency of mutations of FLT3 gene ("internal tandem duplication") and good response to induction therapy. The mutations of NPM gene and consequent distribution of the mutated NPM protein in the cytoplasm of leukaemic cells represent the more specific and frequent molecular events till now found in normal karyotype LAM. The authors of the present invention have also shown that NPM mutations represent an excellent marker for prognosis (Sclmittger et al., 2005) and monitoring the minimal residual disease normal karyotype LAMs.

Therefore the authors of the present invention have identified mutant sequences of nucleophosmin protein (NPM) and mutants of NPM gene encoding for them, which advantageously can be employed as: markers in the preparation of diagnostic kits and prognostic markers and for monitoring minimal residual disease, and as therapeutic targets in the primary normal karyotype-LAMs.

Therefore, the present invention provides a specific method for diagnosing, within the heterogeneous category of normal karyotype LAMs, a new subtype, called LAM NPMc+, through immunohistochemical studies with anti-NPM antibodies (identification of cytoplasmic NPM) and/or analysis of mutations of NPM gene. This observation has important diagnostic implications, because, till now, the normal karyotype LAM was classified only based on fallacious morphological criterions (Jaffe et al., 2001). Particularly, the authors have used monoclonal antibodies against epitopes resistant to the fixatives of NPM molecule (Cordell et al., 1999; Falini et al., 2002) that make them applicable to analysis of routine biopsy samples fixed and included in paraffin such as, for example, osteomedullary biopsies or bone marrow clots. Since the NPM mutations are always heterozygote, leukaemic cells contain both wild-type and mutated NPM protein. These two types of proteins cannot be distinguish each other using the actual anti-NPM monoclonal antibodies.

More specifically, in order to study the sub-cellular distribution of NPM mutants without the interference of wild-type NPM protein, the authors have produced a polyclonal antibody (denominated Sil-C) that is able to recognize specifically NPM mutants.

The cytoplasmic location of NPM (and the mutation of NPM gene) is specifically associated to the normal karyotype. Therefore, it represents an excellent immunohistochemical marker for prognosis, since it allows the assignment to the "intermediary risk" LAM category (in which are included the patients with normal karyotype) of those leukaemic patients that cannot be otherwise classified cytogenetically because of insufficient material, deterioration of the biological sample, absence of mitosis, difficulty to interpret surely the karyotype.

In addition, the immunohistochemical test for the demonstration of cytoplasmic NPM (NPMc+) (predictive at 100% of mutations of exon-12 of NPM gene) can be considered as predictive factor for prognosis in normal karyotype LAMs, by identifying survival differences in the LAM NPMc+ cases compared with NPMc−. More specifically, the presence of exon 12 mutations of NPM in absence of mutations of FLT3 gene has allowed us to identify a new group of good prognosis myeloid leukaemias with normal karyotype (Schnittger et al., 2005).

In addition, the immunohistochemical identification of cytoplasmic NPM (NPMc+) can be considered as predictive factor for a good response to the induction therapy in the normal karyotype LAMs.

The NPM assays at cytoplasmic level or for mutation at gene level, provided by the authors of the present invention, are highly sensitive, specific, simple, economic and rapid diagnostic tests (48-72 hours to achieve the result) and they use immunohistochemical and biomolecular techniques well known to those skilled in the art. In addition, such assays can advantageously be employed for monitoring the minimal residual disease in a situation (normal karyotype) for which until today are not available molecular or immunophenotypical markers.

In addition, the results of the study carried out by the authors of the present invention suggest the provision of new therapeutic treatments of LAMs NPMc+ by the use of anti-sense oligonucleotides or small RNAs, which, packaged in lipid particles or virus (Downward J., 2004), are able to interfere with the translation and transcription processes of the genes carrying the mutations encoding for mutated NPM proteins according to the invention. Among the possible therapeutic applications there is the employment of intracellular antibodies ("intrabodies") (Stocks M R, 2005) specifically directed against the C-terminal portion of NPM mutants or the use of small molecules (peptides or like) able to inhibit the specific C-terminal region of NPM mutants.

Among the possible therapeutic applications must be included also those that interfere with post-translational changes (acetylation, phosphorylation, ubiquitination, etc.)

of NPM molecule (mutated and wild-type) and molecules interacting with them or alterations of routes of the cellular signal specifically associated with the presence of mutated NPM proteins.

In addition, the administration of the mutant NPM protein or portions thereof (e.g. peptides) or nucleotide sequences encoding for the protein or portions thereof for the induction of anti-tumour immunity can advantageously be employed for preventive or therapeutic use.

Therefore are object of the present invention mutated nucleophosmin proteins (NPM) characterized in that they have a cytoplasmic location and comprise an amino acid sequence mutated at level of at least one of the tryptophan residues 288 and/or 290, and/or a signal motif of nuclear export (NES), present in the C-terminal region of the sequence of the human nucleophosmin (NP_002511). In a preferred embodiment of the protein of the present invention, the mutation interests both two tryptophan 288 and 290 (67.5% of all NPM mutants) or only tryptophan 290.

In a preferred embodiment of the protein of the present invention said signal motif of nuclear export (NES) comprises an amino acid sequence YxxxYxxYxY (SEQ ID No 56) where Y is a hydrophobic amino acid selected from the group usually consisting of leucine, isoleucine, methionine, valine, phenylalanine, and x can be any amino acid or fragments and variants thereof. Preferably, the sequence Yxxx-YxxYxY (SEQ ID No 56) is selected from the group consisting of LxxxVxxVxL (SEQ ID No 1), LxxxLxxVxL (SEQ ID No 2), LxxxFxxVxL (SEQ ID No 3), LxxxMxxVxL (SEQ ID No 4), LxxxCxxVxL (SEQ ID No 5). More preferably Lxxx-VxxVxL (SEQ ID No 1) (the most common NES motif) it is selected from the group consisting of LCLAVEEVSL (SEQ ID No 6); LCMAVEEVSL (SEQ ID No 7); LCVAVEEVSL (SEQ ID No 8); LSRAVEEVSL (SEQ ID No 9); LCTAVEEVSL (SEQ ID No 10); LSQAVEEVSL (SEQ ID No 11); LCHAVEEVSL (SEQ ID No 12); LCRAVEEVSL (SEQ ID No 13); LCRGVEEVSL (SEQ ID No 14); LCQAVEEVSL (SEQ ID No 15); LCAAVEEVSL (SEQ ID No 16); LCKAVEEVSL (SEQ ID No 17). Preferably, Lxxx-LxxVxL (SEQ ID No 2) is selected from the group consisting of LWQSLAQVSL (SEQ ID No 18); LWQSLEKVSL (SEQ ID No 19); LWQSLSKVSL (SEQ ID No 20); LCTFLEEVSL (SEQ ID No 21). Yet more preferably LxxxFxxVxL (SEQ ID No 3) is selected from the group consisting of LWQC-FAQVSL (SEQ ID No 22); LWQCFSKVSL (SEQ ID No 23); LWQRFQEVSL (SEQ ID No 24); LWQDFLNRL (SEQ ID No 25). In a preferred embodiment of the present invention LxxxMxxVxL (SEQ ID No 4) is LWQSMEEVSL (SEQ ID No 26) or LWQSMEEVSL (SEQ ID No 27). In another preferred embodiment LxxxCxxVxL (SEQ ID No 5) is LWQCCSQVSL (SEQ ID No 28).

Preferably, the C-terminal region of the mutated proteins according to the invention can include also the VSLRK peptide (SEQ ID No 29) in which the L-amino acid represents the last amino acid of NES motifs as above defined.

In a preferred embodiment the amino acid sequences of NES motif, as above defined, can comprise further a D-amino acid upstream of L-amino acid at the N-terminal end of said NES motif (for instance DLCLAVEEVSLRK (SEQ ID No 30); DLCMAVEEVSLRK (SEQ ID No 31); DLCVAVEEVSLRK (SEQ ID No 32); DLCLAVEEVSLRK (SEQ ID No 33); DLWQSLAQVSLRK (SEQ ID No 34); DLWQSLEKVSLRK (SEQ ID No 35).

According to a particular aspect of the present invention the mutated NPM proteins, as above described, can be fused to a reporter protein that in turn can be selected from the group consisting of EGFP, β-galactosidase, luciferase, GFP. The fusion proteins can be prepared by melting DNA encoding for the aforesaid proteins, commercially available, with the peptide of the present invention and then expressing the so prepared fusion product.

The present invention refers to a mutated or fusion NPM protein as above described, conjugated with a nanoparticle (i.e. Quantum Dot).

Are further object of the present invention the oligonucleotide sequences encoding for the mutated proteins or fragments and variants thereof, as above defined. The oligonucleotide sequences according to the invention can be deoxyribonucleotide or ribonucleotide sequences or their complementary sequences.

According to a preferred embodiment of the present invention the deoxyribonucleotide sequences can include one of the sequences having the following deposit numbers of Gen-Bank: AY740634, AY740635, AY740636, AY740637 AY740638, AY740639.

In a particular embodiment of the invention the oligonucleotide sequences can be labelled with an agent selected from the group consisting of fluorescent substance, biotin, radioisotope, nanoparticle. The labelling can be also useful for the use of the aforesaid oligonucleotide sequences as markers for in vitro diagnosis and/or monitoring the minimal residual disease and/or prognosis of LAMs characterized by normal karyotype. Particularly, the marker consists in at least a couple of primers, that can be labelled or not in one or in both the primers with an agent selected from the group consisting of fluorescent substance, biotin, radioisotope, nanoparticle (Quantumdot). In another embodiment the marker consists in at least an oligonucleotide probe that can be labelled with an agent selected from the group consisting of fluorescent substance, biotin, radioisotope, nanoparticle.

Further objects of the present invention are the primers having the following sequences:

i) NPM1_25F:
(SEQ ID No 36)
5'-GGTTGTTCTCTGGAGCAGCGTTC-3';

NPM1_111 2R:
(SEQ ID No 37)
5'-CCTGGACAACATTTATCAAACACGGTA-3';

ii) NPM1_390F:
(SEQ ID No 38)
5'-GGTCTTAAGGTTGAAGTGTGGT-3';

NPM1_1043_R;
(SEQ ID No 39)
5'-TCAACTGTTACAGAAATGAAATAAGACG-3';

iii) NPM_940F_mutA
(SEQ ID No 40)
5'-GAGGCTATTCAAGATCTCTGTCT-3';

NPM1_1112 R
(SEQ ID No 41)
5'-CCTGGACAACATTTATCAAAGACGGTA-3';

iv) NPM_940F_mutB
(SEQ ID No 42)
5'-GAGGCTATTCAAGATCTCTGCAT 3';

NPM1_1112 R
(SEQ ID No 43)
5'-CCTGGACAACATTTATCAAACACGGTA3';

v) NPM_940F_mutC
(SEQ ID No 44)
5'-GAGGCTATTCAAGATCTCTGCGT-3';

NPM1_1112 R

```
                                                    (SEQ ID No 45)
        5'-CCTGGACAACATTTATCAAACACGGTA-3';

vi)   NPM_940F_mutD
                                                    (SEQ ID No 46)
        5'-GAGGCTATTCMGATCTCTGCCT-3';

NPM1_1112 R
                                                    (SEQ ID No 47)
        5'-CGTGGACAACATTTATCAAACACGGTA-3';

vii)  NPM1-F:
                                                    (SEQ ID No 48)
        5'-TTAACTCTCTGGTGGTAGAATGAA-3';

NPM1-R:
                                                    (SEQ ID No 49)
        5'-CCAGACTATTTGCCATTCCTAAC-3';

viii) NPM1_89F_BamHI:
                                                    (SEQ ID No 50)
        5'-GCCACGGATCCGAAGATTCGATGGAC-3';

NPM1_1044R_EcoRI:
                                                    (SEQ ID No 51)
        5'ATCAAGAATTCCAGAAATGAAATAAGA CG-3';

ix)   cNPM-F:
                                                    (SEQ ID No 52)
        5'-GAAGAATTGCTTCCGGATGACT-3'
        and cNPM mut.A-R:
                                                    (SEQ ID No 53)
        5'-CTTCCTCCACTGCCAGACAGA-3'
        or cNPM mut.B-R:
                                                    (SEQ ID No 54)
        5'-TTCCTCCACTGCCATGCAG-3'.
```

Particularly, the primers i) can be employed for the amplification, preferably by RT-PCR, of the encoding region of NPM gene (NM_002520). The primers ii) can be used alone for the amplification that produces a construct with a pCRII-mouse vector (Invitrogen). The primers iii), iv), v), vi) above mentioned have been designed respectively for the amplification by RT-PCR of oligonucleotide sequences encoding for the mutated proteins:

```
A) DLCLAVEEVSLRK    (SEQ ID No 30)  - primer iii);

B) DLCMAVEEVSLRK    (SEQ ID No 31)  - primer iv);

C) DLCVAVEEVSLRK    (SEQ ID No 32)  - primer v);

D) DLCLAVEEVSLRK    (SEQ ID No 33)  - primer vi);
``` characterized by having as mutation a duplication of tetranucleotide. Finally, the primers vii) are employed for the amplification by genomic DNA of the exon 12 of the C-terminal region of NPM protein; while the primers viii) are used for the insertion in an expression vector of the sequences according to the invention.

It is a further object of the present invention a plasmid comprising one of the above described oligonucleotide sequences. Preferably, said plasmid can be selected from the group consisting of pGEM-T and pGEM-T Easy (Promega).

A further object of the present invention is represented by an expression vector (such as, for instance, a viral vector or pEGFP-cl) comprising one of the above described oligonucleotide sequences. In a preferred embodiment of the present invention said vector is pEGFP-cl, that comprises the sequence of EGFP reporter gene.

The present invention also refers to a host cell able to express at least one of the proteins mutated as above described, said cell comprising the plasmid with above defined characteristics. Preferably, the host cell is prokaryotic.

In addition it is object of the present invention a cellular line, preferably mammal (yet more preferably murine such as NIH 3T3 and BaF3), comprising the expression vector to be employed as experimental study model of LAM NPMc+ or as screening model to test new molecules to be used as potential drugs for such type of leukaemia.

It is a further object of the present invention a method for the preparation of mutated nucleophosmin proteins (NPM) comprising the following steps of:
a) amplification of the oligonucleotide sequence according to the invention by RT-PCR through at least a couple of primers;
b) introduction of the oligonucleotide sequence amplified in step a) in the pGEM-T Easy vector and transfer in an expression vector by restriction enzymes;
c) transfection of the expression vector in a mammalian competent cellular line selected among the murine cellular lines NIH 3T3 and BaF3;
d) extraction and purification of the mutated proteins.

In a preferred form of the method according to the invention said at least couple of primers of the step a) is:

```
        NPM1_89F_BamHI:
                                                    (SEQ ID No 50)
        5'-GCCACGGATCCGAAGATTCGATGGAC-3'

NPM1_1044R_EcoRI:
                                                    (SEQ ID No 51)
        5'-ATCAAGAATTCCAGAAATGAAATAAGACG-3'.
```

According to a further aspect the present invention refers to a monoclonal or polyclonal antibody or a fragment thereof (such as, for instance, a scFv fragment) able to recognize and join selectively at least an antigenic epitope of the C-terminal region (that can comprise VSLRK (SEQ ID No 29)) of mutated NPM proteins according to the invention.

According to a particular aspect of the present invention the monoclonal and polyclonal antibodies can be conjugated with an agent selected from the group consisting of fluorescent substance, enzyme, radioisotope, nanoparticle, medicine.

Particularly the monoclonal antibodies and the polyclonal antibodies according to the invention are specifically directed against the leukaemia-specific epitopes of the C-terminal of NPM that can comprise the peptide VSLRK (SEQ ID No 29), and/or the mutation of at least one of tryptophan residues 288 and 290 (preferably of both tryptophan residues contemporarily or only tryptophan residue 290), and/or the NES motif as above defined.

It is a further object of the present invention the use of monoclonal or polyclonal antibodies as markers for in vitro diagnosis and prognosis, for monitoring minimal residual disease and/or preparation of a drug for the therapy of normal karyotype LAMs. In a preferred embodiment, the present invention contemplates the use of intracellular antibodies ("intrabodies") directed specifically against epitopes of the C-terminal part of the mutants as medicine to inhibit the activity of mutated NPM proteins.

It is an object of the present invention a diagnostic kit for the detection of normal karyotype LAMs starting from a biological sample, comprising the antibody or a fragment thereof. Said antibody or fragment can be directed against epitopes resistant to the fixatives of the native NPM protein or against the C-terminal mutated portion of NPM. Said detection can be achieved by immunohistochemical, immunoenzymatic, immunoblotting, immunoprecipitation assays or a combination thereof.

Further object of the present invention is represented by the use of the oligonucleotide sequences or of the nucleophosmin proteins encoded by them according to the invention, for the preparation of means for in vitro diagnosis or prognosis of normal karyotype LAMs and/or monitoring minimal residual disease. Such means for diagnosis are preferably selected from the group consisting of oligonucleotide probes, primers, epitopes, antibodies.

A particular object of the present invention is represented by the leukaemia-specific antigenic epitope that is created at level of the C-terminal region of mutated nucleophosmin proteins, characterized by comprising the VSLRK peptide (SEQ ID No 29), and/or the mutation of at least one of tryptophan residues 288 and 290 (preferably of both the tryptophan residues contemporarily or only of the tryptophan residue 290), and/or the NES motif as above defined.

Further object of the present invention is constituted by a diagnostic kit for the detection of the normal karyotype LAMs in a biological sample and/or for monitoring minimal residual disease, comprising at least one of the oligonucleotide sequences according to the invention or portion thereof. Said detection can occur through PCR, RT-PCR, Real-time or in situ hybridization, Reverse Dot Blot (RBD), Multiple Tissue Array (My) techniques or a combination thereof.

Particularly, the invention refers to a Real-Time PCR diagnostic kit for monitoring minimal residual disease comprising the following components:

```
i) the couple of primers
                                      (SEQ ID No 52)
cNPM-F:        5'-GAAGAATTGCTTCCGGATGACT-3'
and
                                      (SEQ ID No 53)
cNPM mut.A-R:  5'-CTTCCTCCACTGCCAGACAGA-3'
or
                                      (SEQ ID No 54)
cNPM mut.B-R:  5'-TTCCTCCACTGCCATGCAG-3' ii) and the probe
                                      (SEQ ID No 55)
5'FAM-ACCAAGAGGCTATTCAA-MGB-3'.
```

In addition it is object of the present invention a solid support, such as for example a membrane, or an array, comprising at least one of the oligonucleotide sequences according to the invention.

According to a further aspect, the present invention refers to a in vitro method for the detection of the oligonucleotide sequences encoding for above described mutated nucleophosmin proteins comprising the following steps of:
a) extraction of RNA from the biological test sample;
b) retro-transcription and amplification by RT-PCR or Real-Time PCR by the use of NPM sequence specific primers (Gen Bank NM_002520) as above defined;
c) purification and sequencing of PCR products by using primers.

In a preferred embodiment of the aforesaid method the primers employed in the step b) are the couples of forward and reverse primers from i) to ix) above listed. Preferably, the primers of the step c) are selected from the group consisting of:

```
                                      (SEQ ID No 36)
NPM1_25F:      5'-GGTTGTTCTCTGGAGCAGCGTTC-3';

(SEQ ID No 37)
NPM1_1112R:    5'-CCTGGACAACATTTATCAAACACGGTA-3';
```

-continued
```
                                      (SEQ ID No 38)
NPM1_390F:     5'-GGTCTTAAGGTTGAAGTGTGGT-3';

(SEQ ID No 39)
NPM1_1043_R;   5'-TCAACTGTTACAGAAATGMATAAGACG-3'.
```

The same primers i) taken singly as also the primers ii) can be used in the step c) of the aforesaid method (for the sequencing).

Particularly, in the case in which it is employed the Real-time for the detection, the "Hybridization probe" or "SYBR green detection" or "Hydrolysis probe" system can alternatively be employed.

In a preferred embodiment the present invention refers to a method that in the step b) employs a mutation-specific Real Time PCR system. The primers used are
cNPM-F: 5'-GAAGAATTGCTTCCGGATGACT-3' (SEQ ID No 52) and
cNPM mut.A-R: 5'-CTTCCTCCACTGCCAGACAGA-3' SEQ ID No 53) or
cNPM mut.B-R: 5'-TTCCTCCACTGCCATGCAG-3' (SEQ ID No 54)
and the probe is 5'FAM-ACCAAGAGGCTATTCAA-MGB-3' (SEQ ID No 55) as shown in FIG. 13 (see also Example 5).

Further the invention refers to an oligonucleotide probe having the following oligonucleotide sequence 5'FAM-ACCAAGAGGCTATTCAA-MGB-3' (SEQ ID No 55).

It is a further object of the present invention a method for the detection of the oligonucleotide sequences encoding for the above described mutated nucleophosmin proteins comprising the following steps of:
a) extraction of RNA from the biological test sample;
b) amplification by the use of specific primers for the NPM sequence of (Gen Bank NM_002520);
c) detection of the PCR products.

Preferably, the amplification occurs through diagnostic PCR or Real-time PCR. Particularly in the case in which Real-time is employed for the detection, the "Hybridization probe" or "SYBR green detection" or "Hydrolisis probe" system can alternatively be employed.

In a preferred embodiment of the aforesaid method the primers employed in the step b) are selected from the group consisting of:

```
i)   NPM_940F_mutA:
                                      (SEQ ID No 40)
     5'-GAGGCTATTCAAGATCTCTGTCT-3';

NPM1_111 2R:
                                      (SEQ ID No 41)
     5'-CCTGGACAACATTTATCAAACACGGTA-3';
or
     NPM1_390F:
                                      (SEQ ID No 38)
     5'-GGTCTTAAGGTTGAAGTGTGGT-3';

NPM1_1043_R;
                                      (SEQ ID No 39)
     5'-TCAACTGTTACAGAAATGAAATAAGACG-3';

ii)  NPM_940F_mutB:
                                      (SEQ ID No 42)
     5'-GAGGCTATTCAAGATCTCTGCAT 3';

NPM1_1112R:
                                      (SEQ ID No 43)
     5'-CCTGGACAACATTTATCAAACACGGTA 3';
```

-continued iii) NPM_940F_mutC (SEQ ID No 44)
5'-GAGGCTATTCAAGATCTCTGCGT-3;

NPM1_1112R (SEQ ID No 45)
5'-CCTGGACAACATTTATCAAACACGGTA-3';

iv) NPM_940F_mutD (SEQ ID No 46)
5'-GAGGCTATTCAAGATCTCTGCCT-3';

NPM1_1112 R (SEQ ID No 47)
5'-CCTGGACAACATTTATCAAACACGGTA-3'.

Particularly in the case in which Real-time is employed for the detection the Hybridization probe" or "SYBR green detection" or "Hydrolisis probe" system can alternatively be employed.

According to a further aspect, the present invention has as object an in vitro method for the detection of the cytoplasmic location of NPM in a biological sample comprising the following steps of:
a) contacting the biological sample with at least an antibody or a fragment thereof able to detect the cytoplasmic location of NPM;
b) detection of the antibody-antigenic epitope bond, by standard immunofluorescence or immuno enzymatic techniques.

Said biological sample of step a) of the aforesaid method is selected from the group consisting of: paraffin embedded tissue sections, preferably of bone marrow (osteomedullary biopsy or haematic clot) or medullary smears and blood or liquor cytological samples.

Preferably said antibody of the step a) of the method is a monoclonal antibody. Particularly, can be used monoclonal antibodies directed against epitopes resistant to fixatives of NPM (Cordell et al., 1999; Falini et al., 2002) that are able to detect the cytoplasmic location of the protein.

In a preferred embodiment the aforesaid method can subsequently include another step c) for the detection of mutated NPM proteins in the above described pathological samples (sections, smears, cytological samples) through antibodies able to recognize and join selectively at least an antigenic epitope of mutated NPM proteins according to the invention or c1) for the detection of oligonucleotide sequences mutated, for example, by amplification methods with specific primers. The primers of the step c1) can be:

(SEQ ID No 40)
NPM_940F_mutA    5'-GAGGCTATTCAAGATCTCTGTCT-3';

(SEQ ID No 41)
NPM1_1112R    5'-CCTGGACAACATTTATCAAACACGGTA-3';

(SEQ ID No 42)
NPM_940F_mutB    5'-GAGGCTATTCAAGATCTCTGCAT 3';

(SEQ ID No 43)
NPM1_1112R    5'-CCTGGACAACATTTATCAAACACGGTA 3';

(SEQ ID No 44)
NPM_940F_mutC    5'-GAGGCTATTCAAGATCTCTGCGT-3';

(SEQ ID No 45)
NPM1_1112R    5'-GCTGGACAACATTTATCAAACACGGTA-3';

(SEQ ID No 46)
NPM_940F_mutD    5'-GAGGCTATTCAAGATGTCTGCCT-3';

(SEQ ID No 47)
NPM1_1112R    5'-CCTGGACAACATTTATCAAACACGGTA-3';

for the identification of the mutations A-D.

In a preferred embodiment of the method according to the invention the antigenic epitope of step c) can comprise the VSLRK peptide (SEQ ID No 29), and/or the mutation of at least one of tryptophan residues 288 and 290 (preferably both tryptophan residues contemporarily or only tryptophan residue 290), and/or the NES motif as above defined.

Further object of the present invention is represented by anti-sense oligonucleotides able of hybridize to at least one of the oligonucleotide sequences encoding for mutated nucleophosmin proteins according to the invention and to interfere with their transcription process. In a preferred embodiment, it is an object of the present invention the use of the anti-sense oligonucleotides for the preparation of a drug for the treatment of primary LAMs.

The present invention has as further object, a ribonucleotide sequence (RNAi) able to hybridize selectively to at least one of the oligonucleotide sequences encoding for mutated nucleophosmin proteins according to the invention and to interfere with their expression. RNAi is a double strand RNA molecule, comprising a combination of sense and anti-sense oligonucleotide strands, which prevents the translation of the target mRNAs.

According to a particular aspect, the present invention refers to the use of the ribonucleotide sequence RNAi, also in the form of microRNA, for the preparation of a drug for the treatment of primary LAMs.

In addition among the possible therapeutic applications, are contemplated, according to the invention, the molecules interfering with the post-translational change processes (acetylation, phosphorylation, ubiquitination) of NPM molecule (mutated and wild-type) or with alterations of routes of the cellular signal specifically associated with the presence of one of mutated NPM proteins that are object of the present invention. In addition, the present invention suggests the use of specific inhibitors of the C-terminal portion of mutant NPM proteins by small molecules (peptides or others) identified using "SAR by NMR" (Shuker et al., 1996) or other methods.

It is a further object of the present invention the use of oligonucleotide sequences or nucleophosmin proteins encoded by them according to the invention, or portions (peptides) thereof, or a combination thereof, for the preparation of an anti-tumour vaccine. In fact, the nucleophosmin proteins or peptides are usable as vaccines against LAM NPMc+ leukaemias.

Further object of the present invention is represented by a pharmaceutical composition comprising at least one of the oligonucleotide sequences or nucleophosmin proteins encoded by them according to the invention, or portions (peptides) thereof, along with pharmacologically acceptable excipients and adjuvants.

It is a further object of the present invention an anti-tumour vaccine comprising at least one of the oligonucleotide sequences or nucleophosmin proteins encoded by them according to the invention, or portions (peptides) thereof, along with pharmacologically acceptable excipients and adjuvants. Said anti-tumour vaccines are specific for the preventive and therapeutic treatment of LAM NPMe+.

The present invention finally has also as object a non human transgenic animal comprising a oligonucleotide sequence encoding for a mutated nucleophosmin protein as above described. Said non human transgenic animal can be employed as experimental study model for the study of new drugs for the treatment of LAM NPMc+.

The patent or application file contains at least one drawing executed in color. Copies of this patent or patent application publication with color drawings will be provided by the Office upon request and payment of the necessary fee.

The present invention now will be described by illustrative not limiting way, according to its preferred embodiments, with particular reference to figures of enclosed drawings, in which:

FIG. 1A shows the histograms relating to the sub-cellular nucleophosmin expression in LAM, respectively, NPMc+ and NPMC− in the left and right panel, respectively; in the left panel the arrows indicate leukaemic cells while the arrowhead indicates a residual haemopoietic cell with expected nucleus-restricted NPM positivity (×1,000); the arrows in the right panel indicate a mitotic cell with expected NPM cytoplasmic expression (×1,000);

Figure 1:
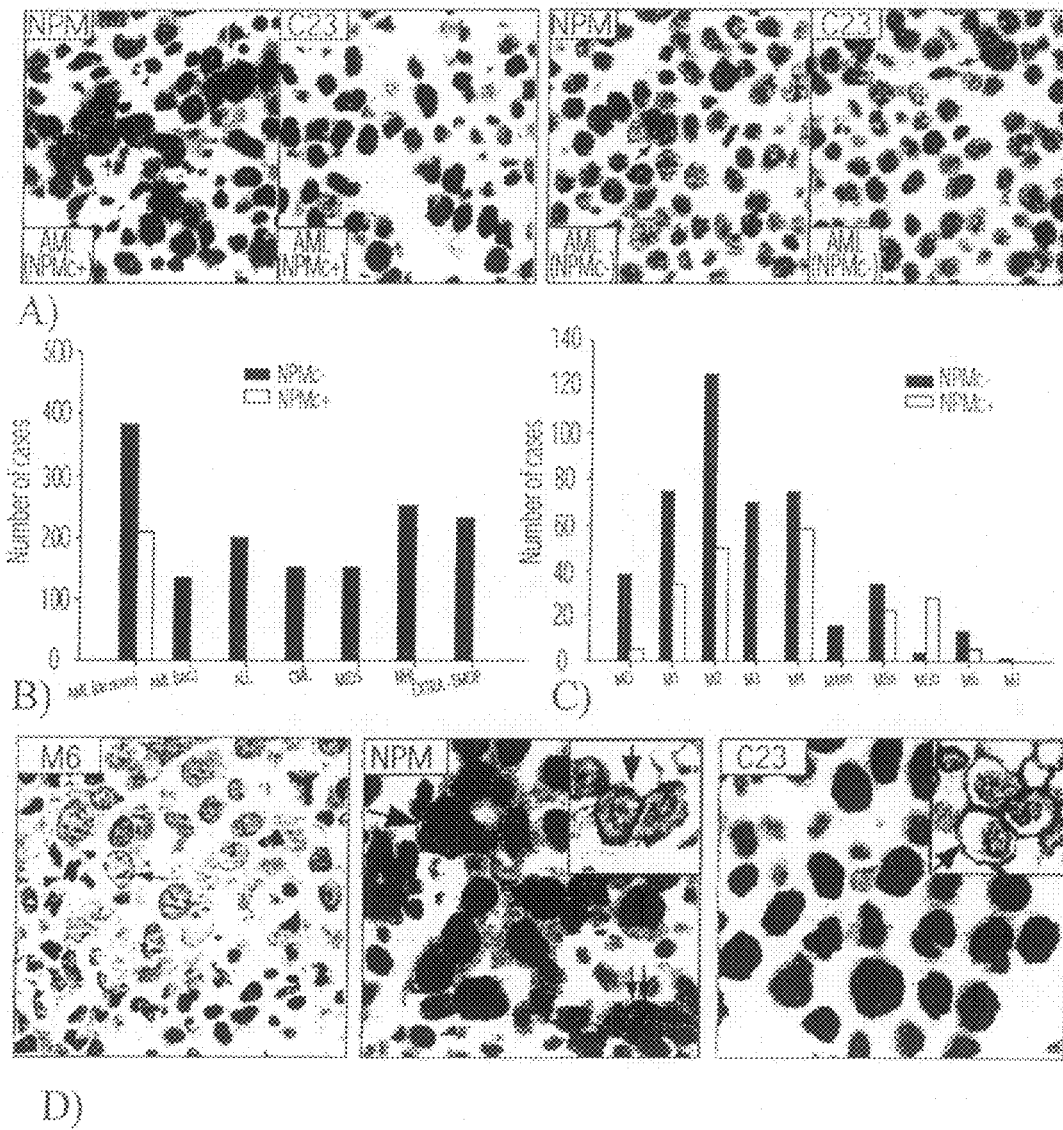
FIG. 1B shows the cytoplasmic NPM expression in 1706 human tumours, which is specific for primary LAMs, not being detectable in other haemopietic and extra-haemopietic tumours such as secondary LAMs; acute lymphoid leukaemia (ALL); chronic myeloid leukaemia (CML); myelodysplastic syndromes (MDS); non-Hodgkin lymphomas (NHL) and extra-haemopoietic solid tumours (EXTRA-HEMOP)
FIG. 1C shows the histograms relating to the correlation between NPM sub-cellular expression and morphology in 591 primary LAMs of GIMEMA/EORTC study plus 70 LAMs of M3 subtype with t(15;17); the LAM-NPMc+s can belong to all FAB subgroups, but are more often M4-M5 type, the FAB-M5b form almost always contains NPM mutations.
Figure 2:
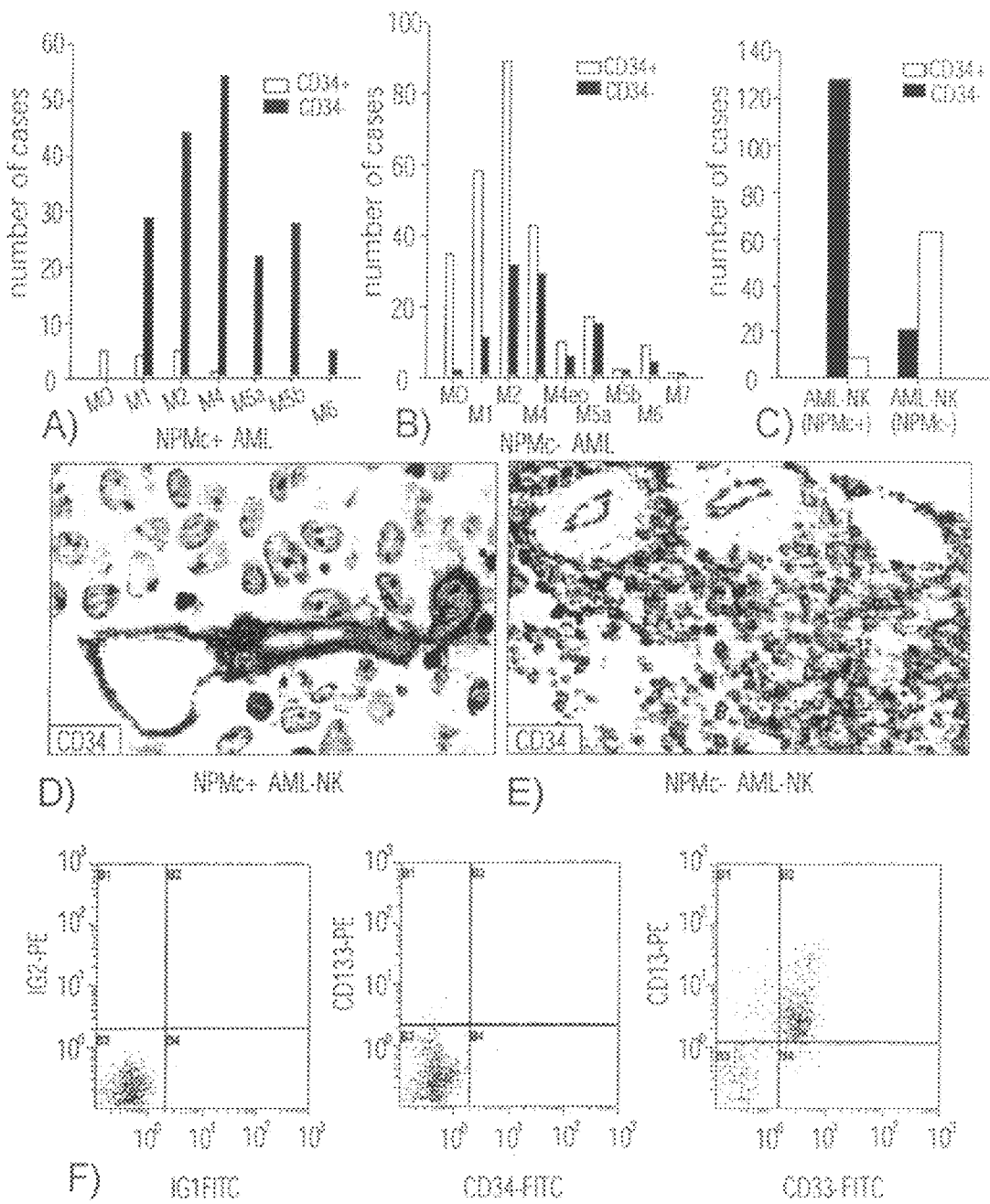
Figure 3:
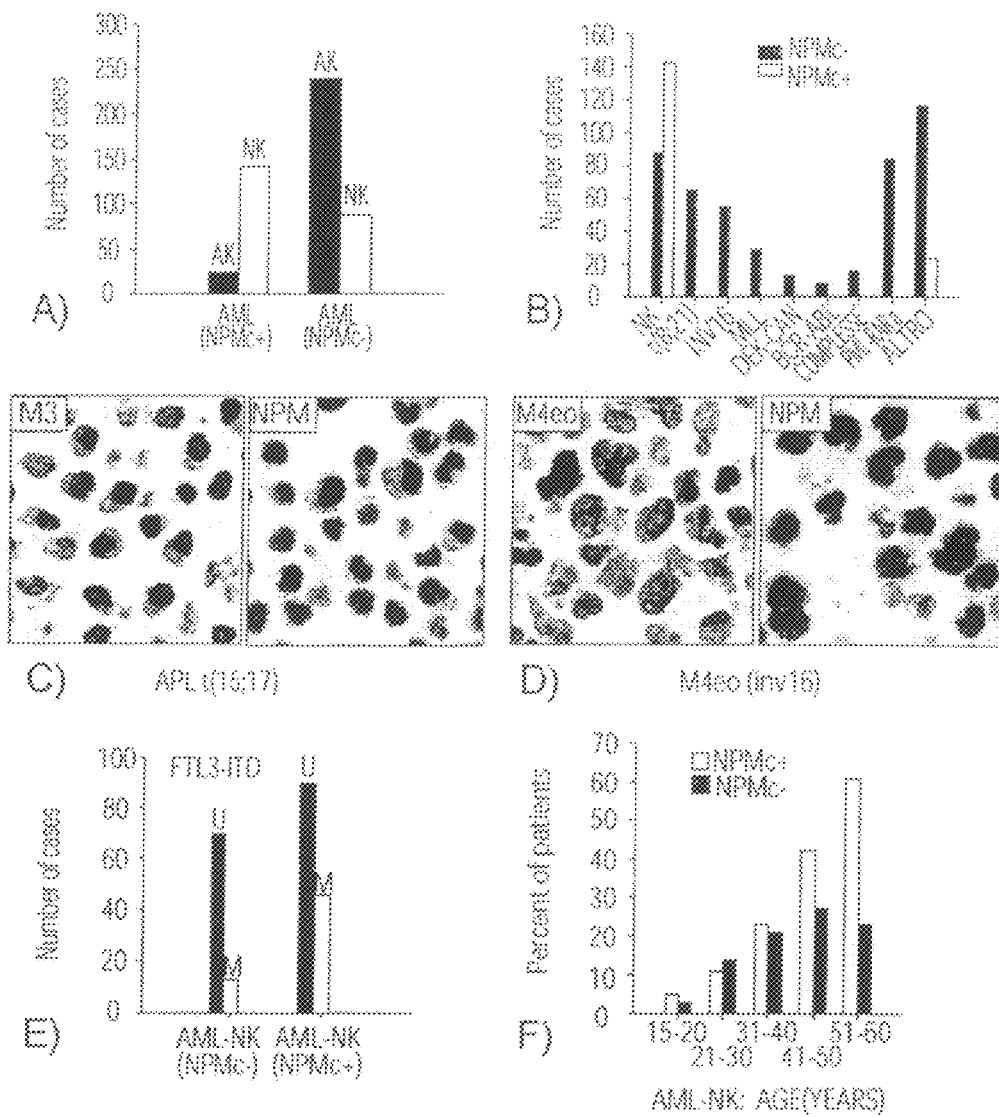
Figure 4:
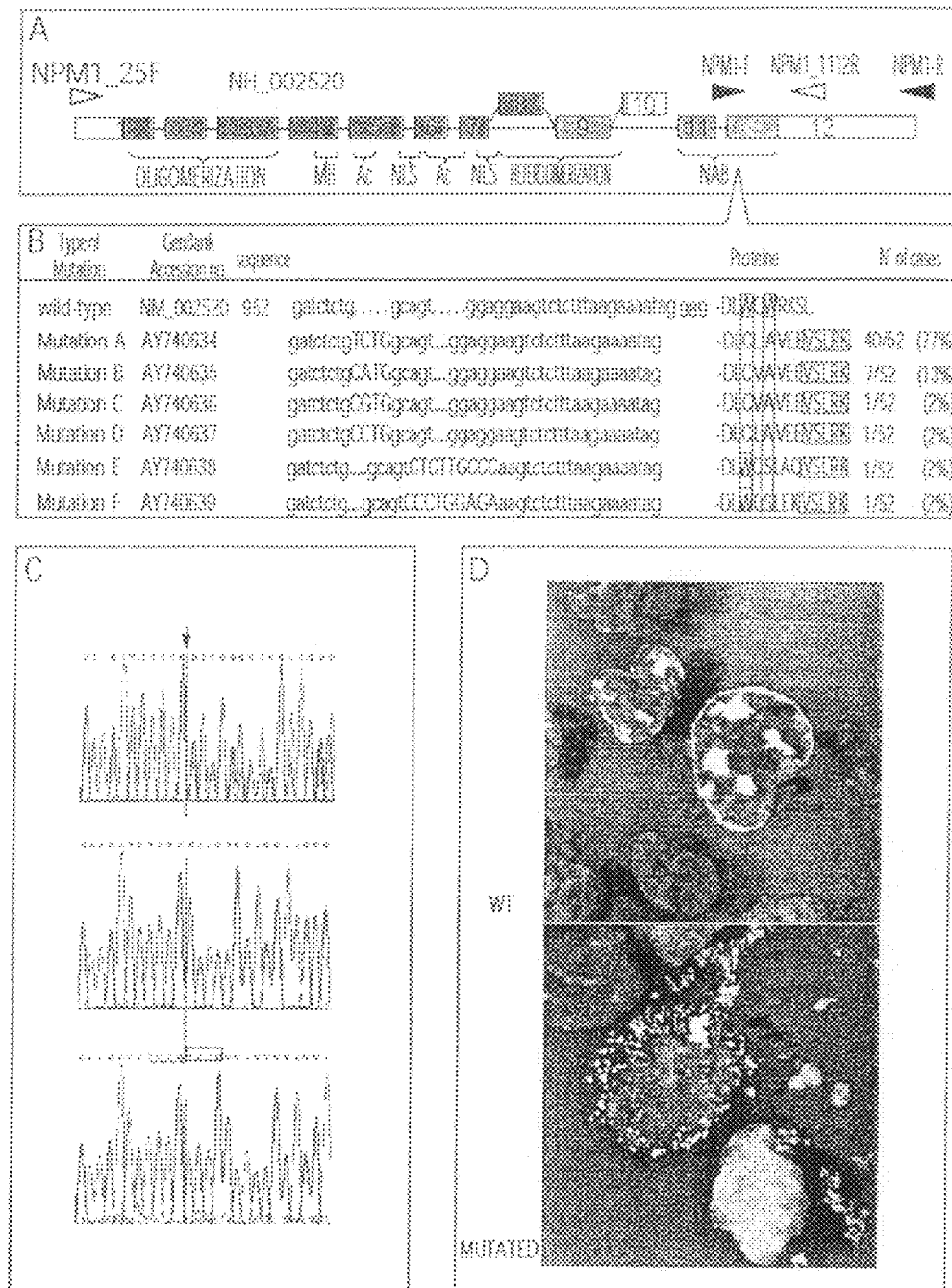
Figure 5:
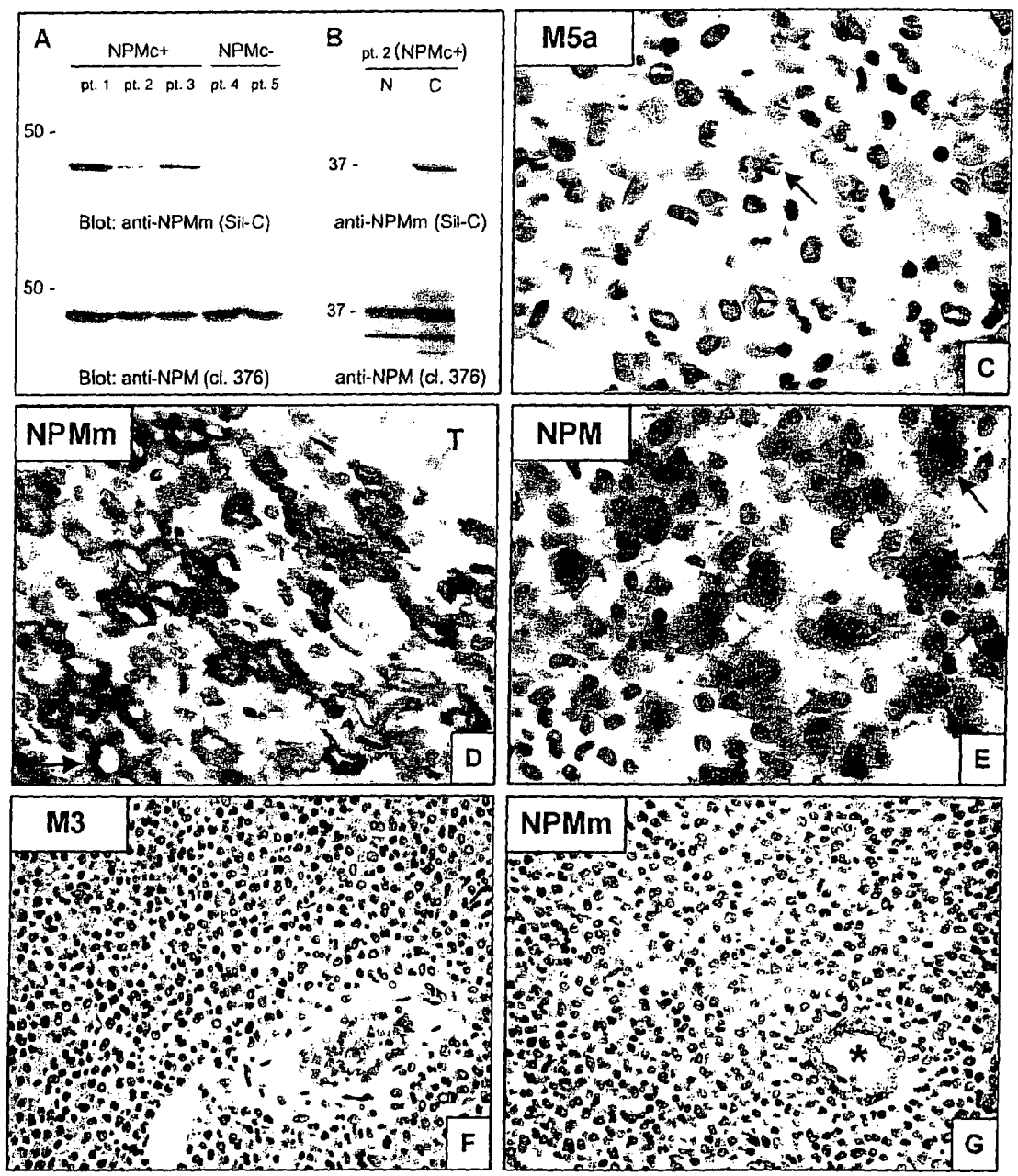
Figure 9A:
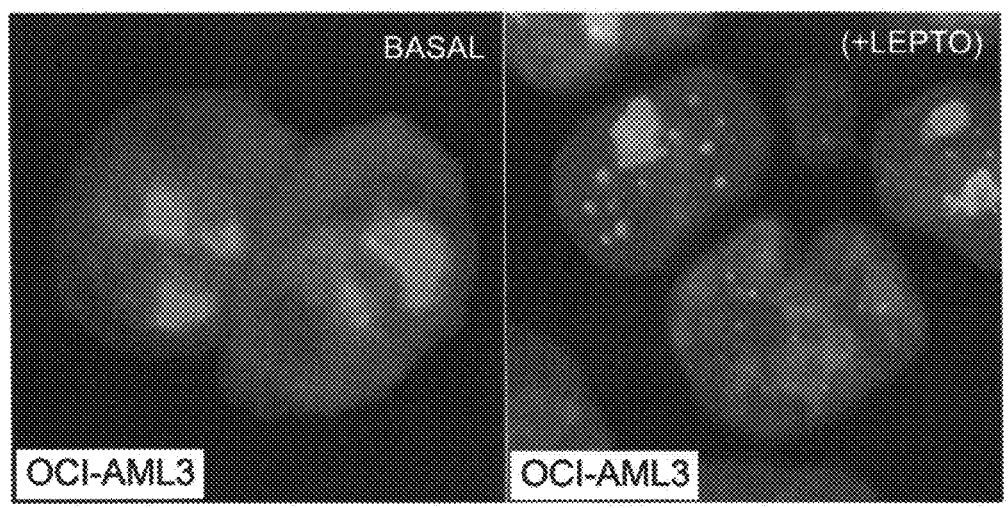
Figure 9B:
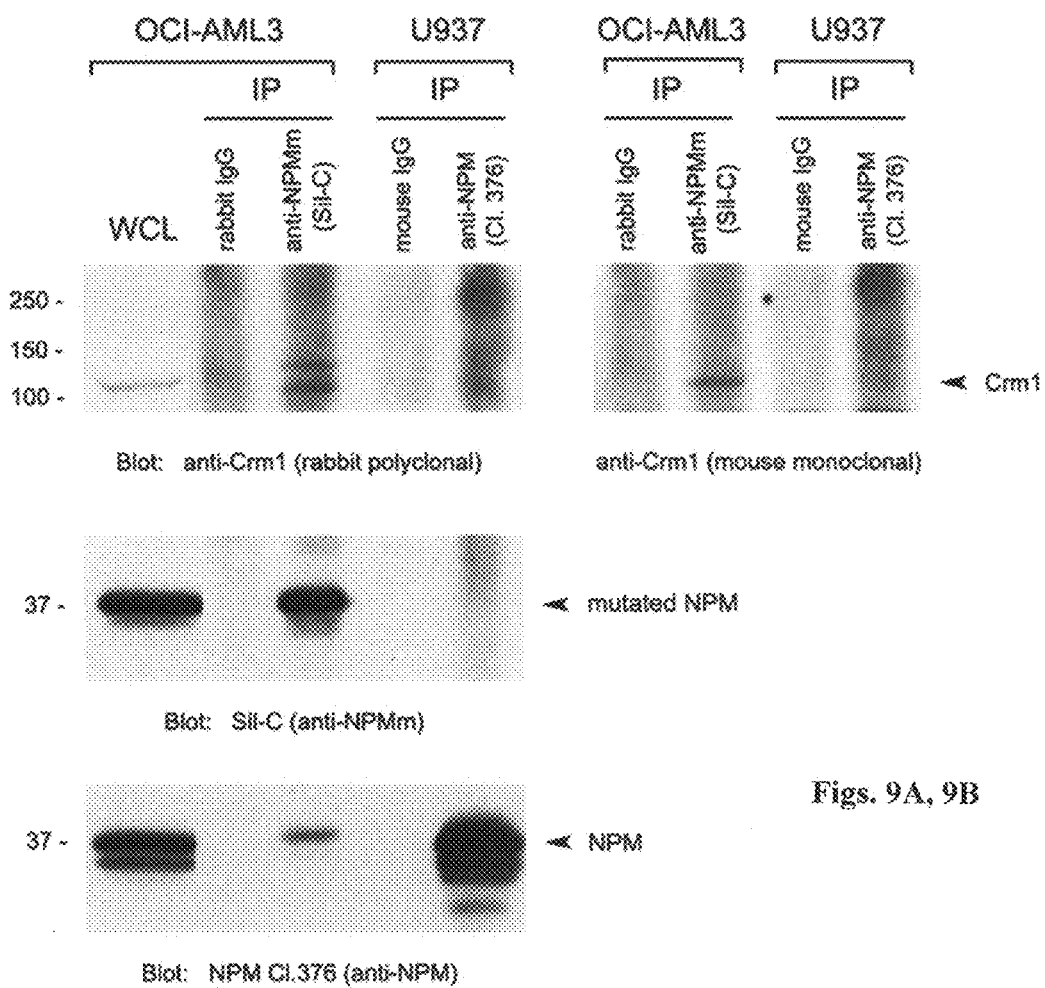
Figure 10:
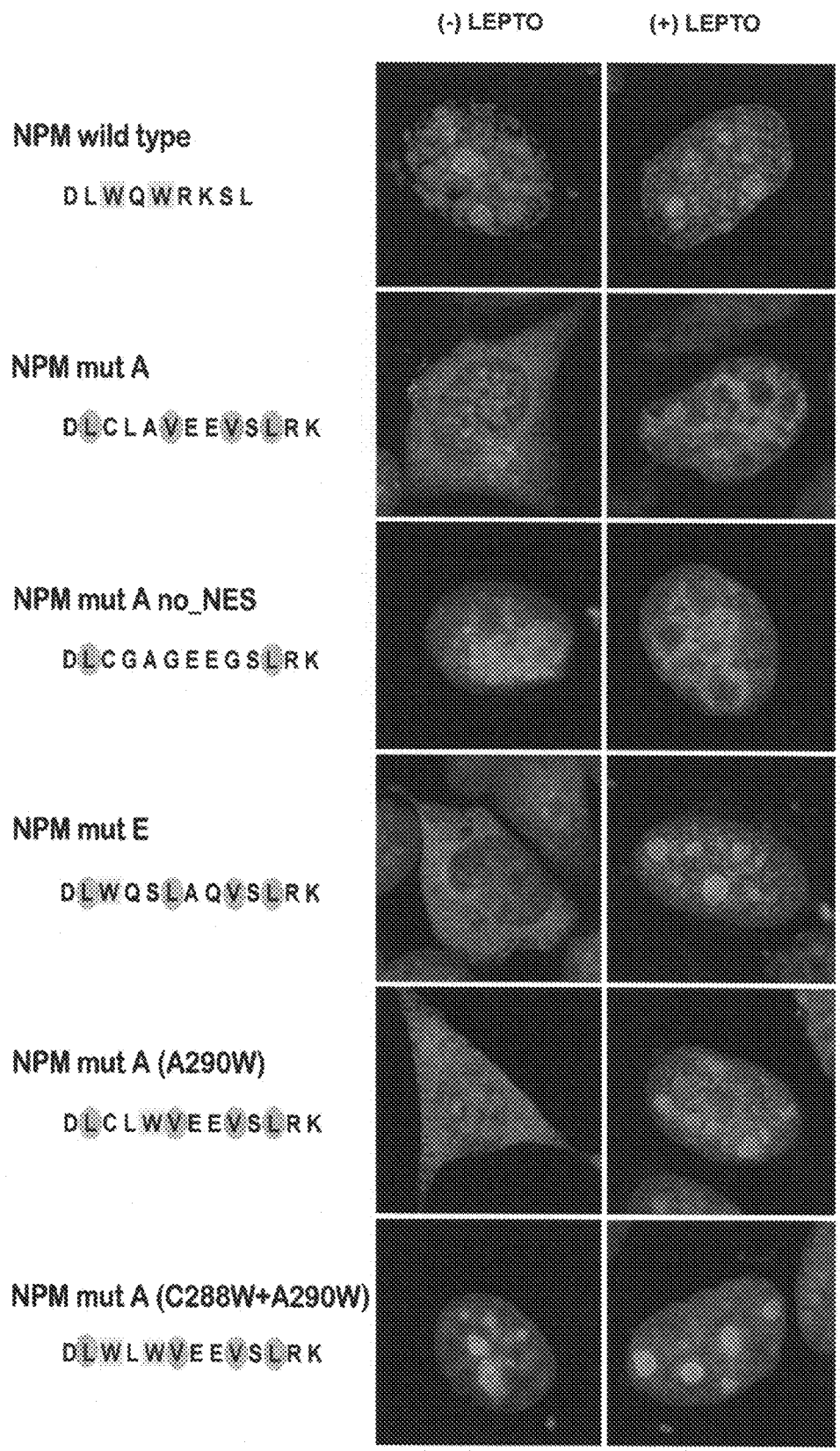
Figure 11A:
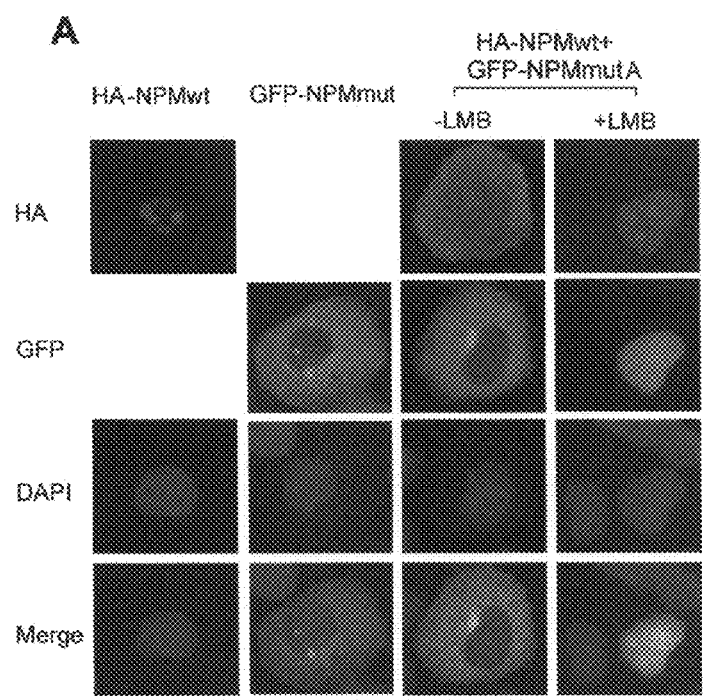
Figure 11B:
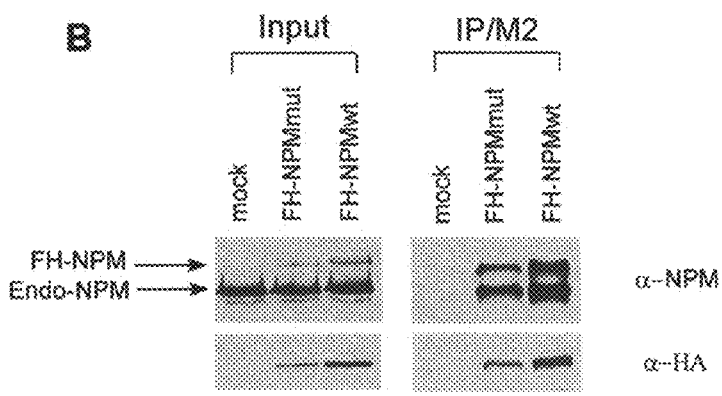
Figure 11C:
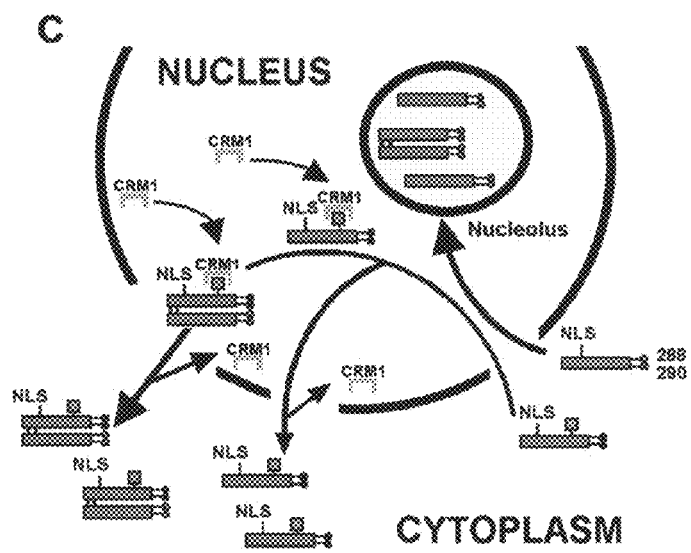
Figure 12:
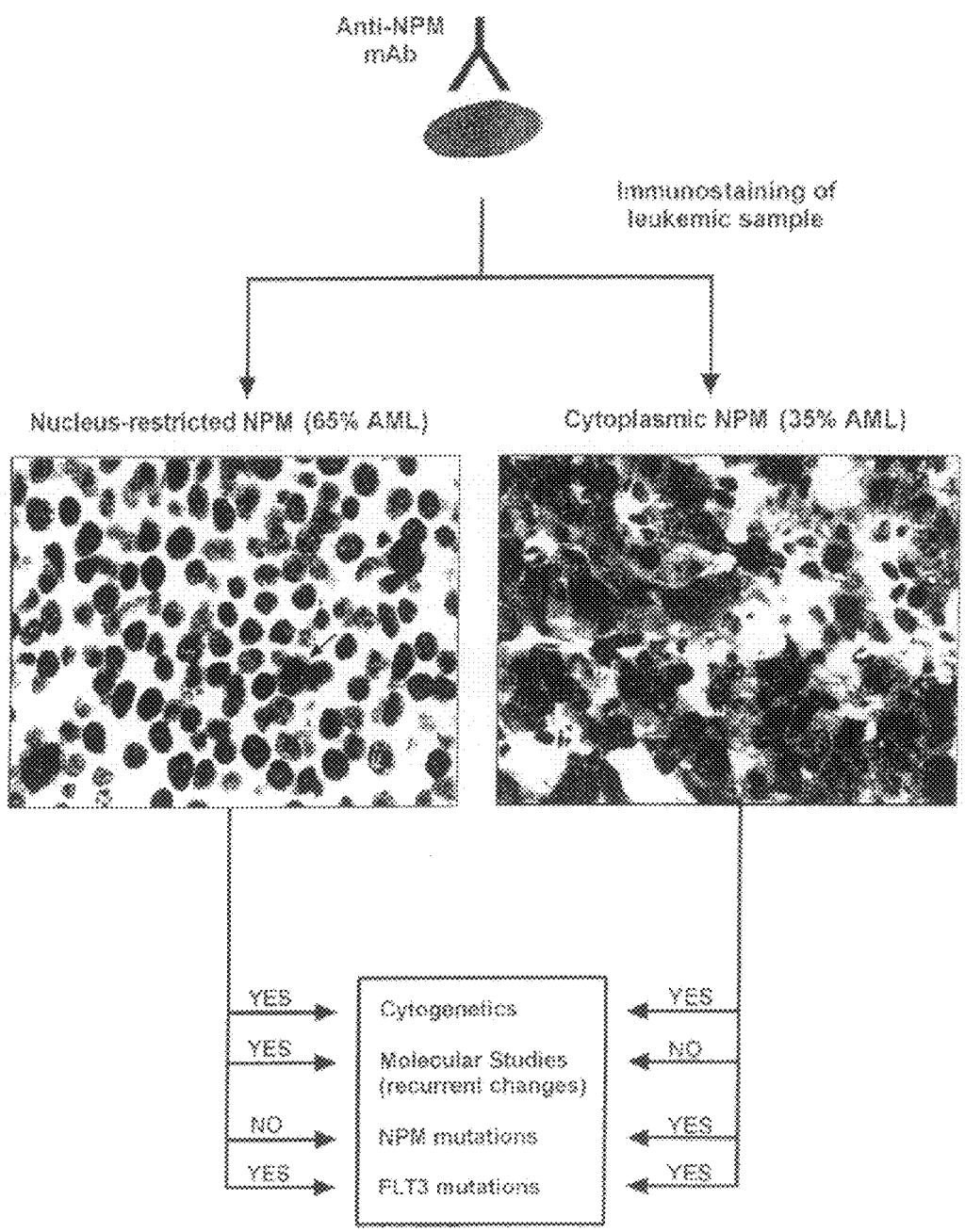
Figure 13:
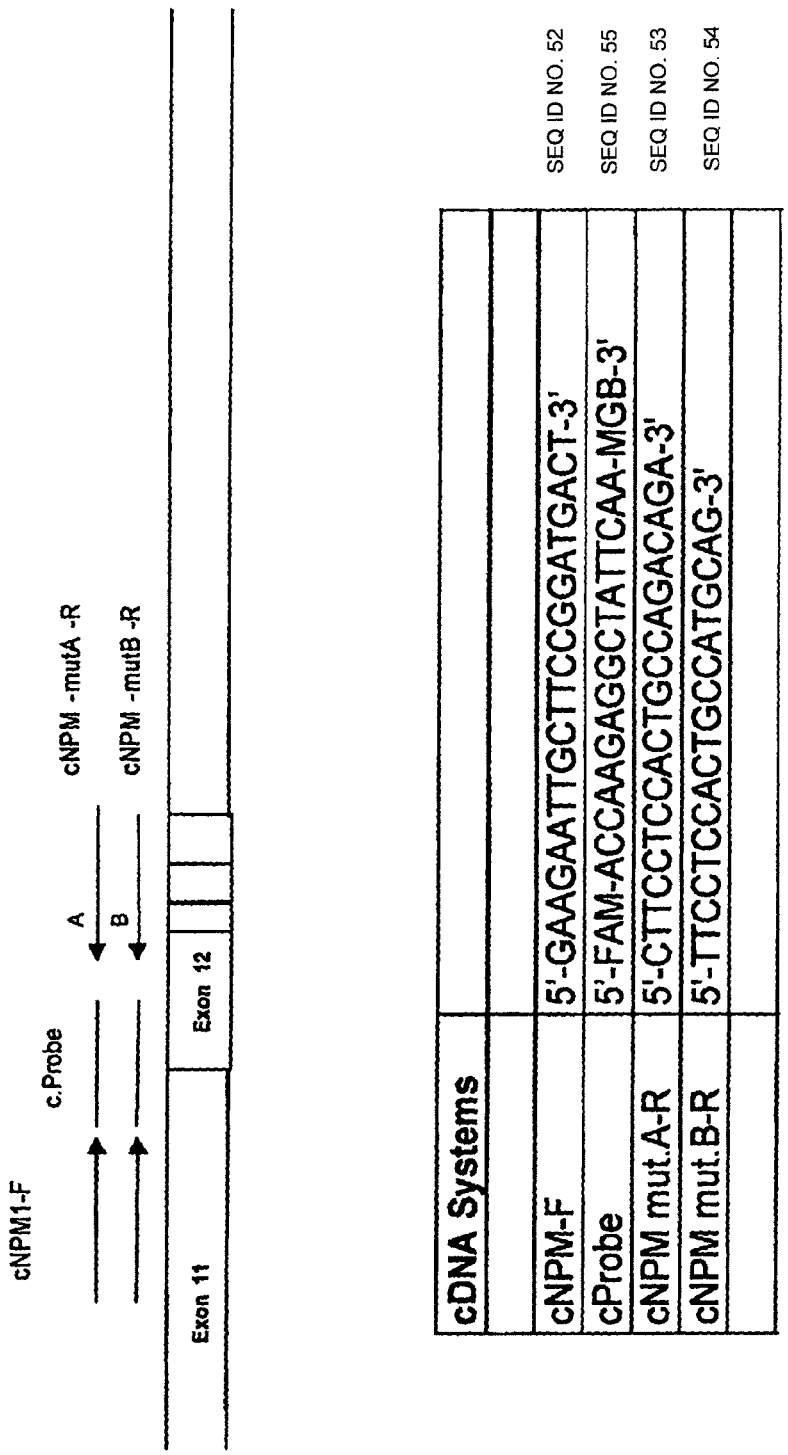
Figure 14:
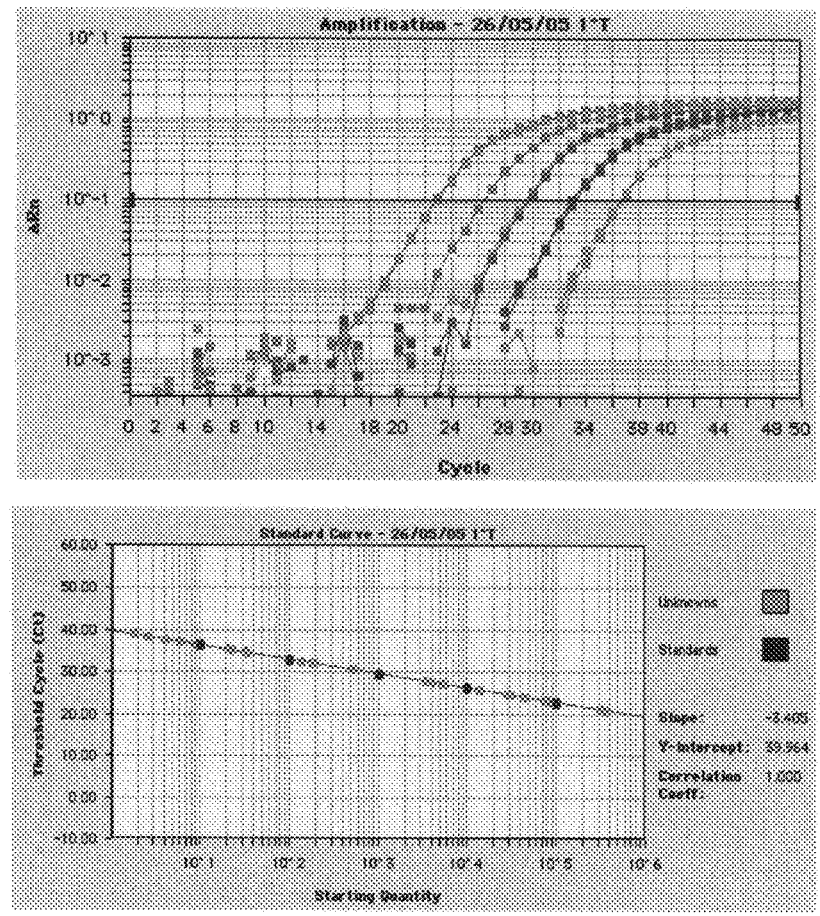
Figure 15:
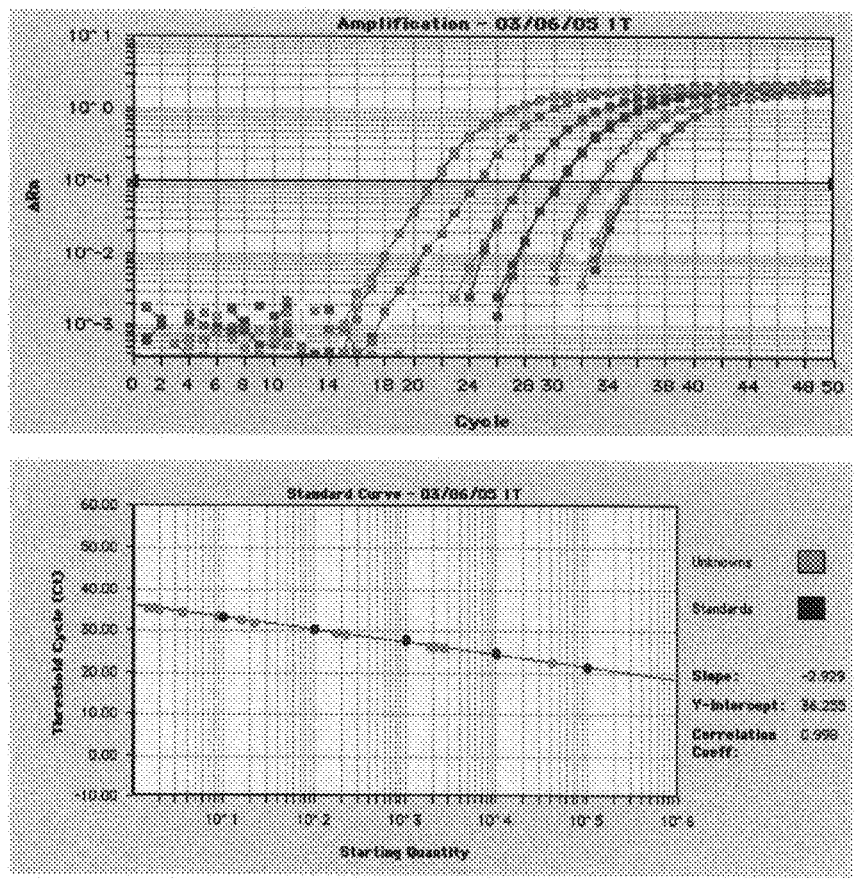
Figure 16:
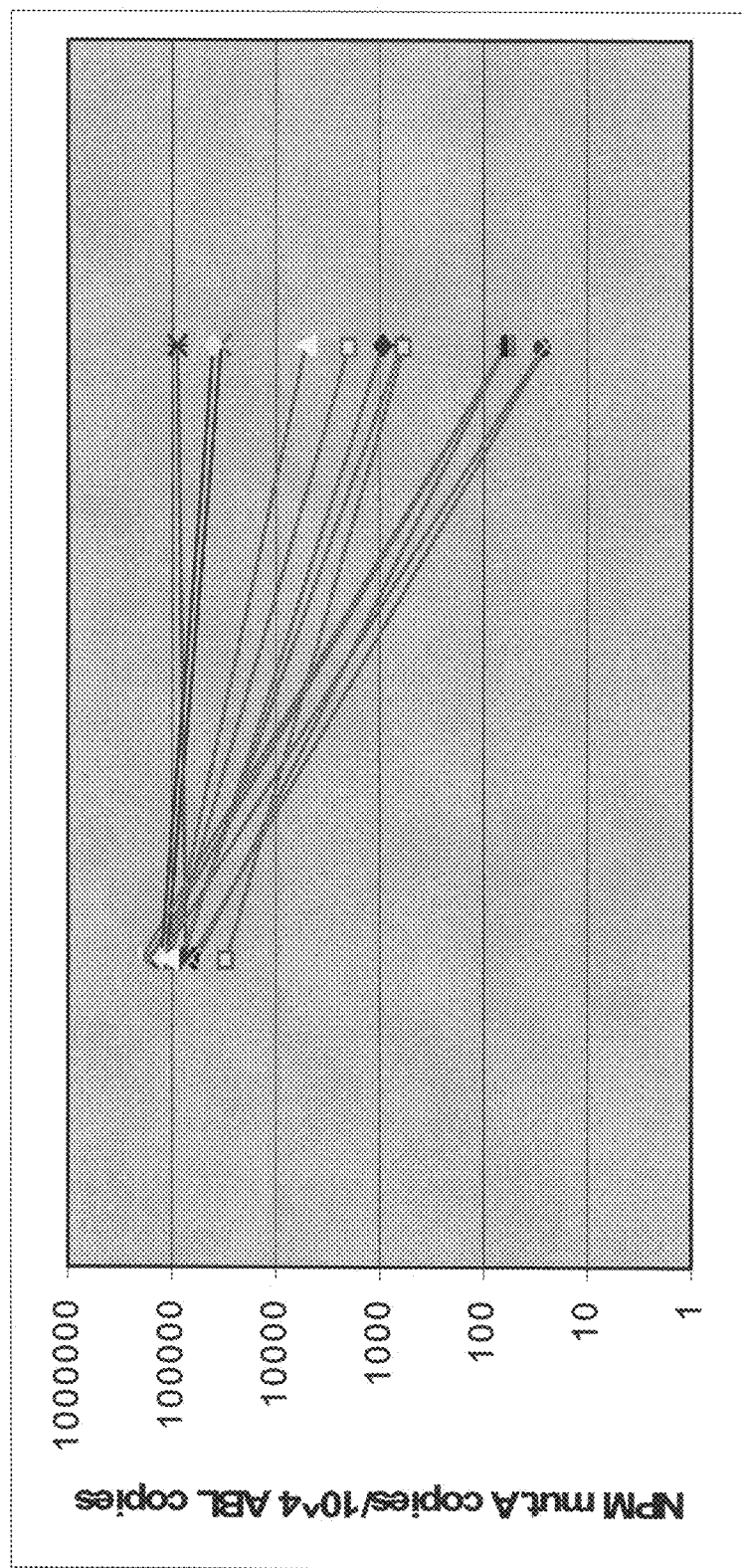
Figure 17:
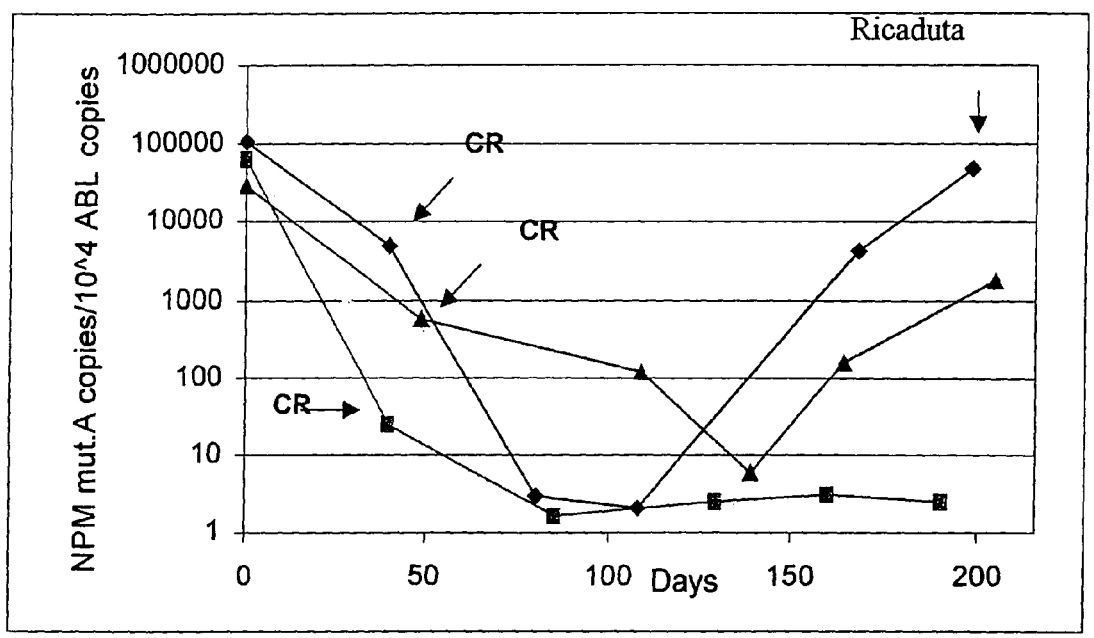

FIG. 1D shows cytoplasmic NPM expression in erythroid and myeloid leukaemic cell lineage ("multilineage involvement"); in the left panel it is shown the marrow infiltrated by myeloid (arrowhead) and erythroid blasts (arrow); in the central panel are indicated abnormal erythroid precursors (arrow) and clusters of myeloid blasts (double arrows), both expressing NPM at cytoplasmic and nuclear level; arrowhead indicates a residual haemopoietic cell with expected nucleus-restricted NPM; in the right panel are indicated the cells with the expected nucleus-restricted nucleolin (C23) expression; arrows in middle and right panels indicate leukaemic cells brown double stained for glycophorin (surface) and blue stained for NPM (cytoplasm plus nucleus) or for C23 (nucleus-restricted); all figures have been obtained using APAAP immunoenzymatic technique; ×1,000;

FIG. 2 shows the histograms relating to the association between cytoplasmic NPM expression and the presence of CD34: FIGS. 2A-C show that in most cases the cytoplasmic NPM expression associates with CD34-negativity, while NPMc− LAM cases show an opposite behavior; FIG. 2D shows a NPMc+ normal karyotype LAM and absence of CD34 expression (osteomedullary biopsy, APAAP technique×1,000); FIG. 2E shows a NPMc-LAM with karyotype normal and intense CD34 positivity (osteomedullary biopsy, APAAP technique×1,000); figure F represents FACS analysis of a NPMc+ LAM; left panel: control; central panel: CD34 (FITC) and CD133 (PE) lacking leukaemic cells; right panel: CD33 (FITC) and CD13 (PE) co-expressing leukaemic cells;

FIG. 3A refers to analysis of 493 patients with LAM of the GIMEMA/EORTC study and shows that the NPMc+ cases associate exclusively to the normal karyotype (NK: normal karyotype; AK: abnormal karyotype);

FIG. 3B shows analysis of 493 LAM GIMEMA/EORTC study plus 109 patients not included in the study (70 acute promyelocytic leukaemias with t(15;17) and 39 LAMs with major chromosomal rearrangements); 24 NPMc+ (column "other") don't associate never to major chromosomal abnormalities and show only smaller abnormalities; none of the NPMe+LAMs associates to major chromosomal abnormalities; 24 NPMc+ cases (column "other") show only smaller abnormalities;

FIGS. 3C and 3D show the expected NPM localization at nuclear level in NPMc+ LAM of M3 and M4eo type (APAAP technique; ×1,000);

FIG. 3E shows that, in context of normal karyotype LAMs (NK), FLT3-ITD mutations (internal tandem duplication-ITD) occur more frequently in the NPMc+ LAMs compared with NPMc− LAMs (U=not mutated; M=mutated);

FIG. 3F shows that, in context of normal karyotype LAMs (NK), NPMc+ forms occur more frequently in more advanced age ranges;

FIG. 3G shows multivariate logistic regression model that establishes the independent association between cytoplasmic NPM and FLT3-ITD; Indip Var: independent variable; GL: degree of freedom; Sig: significance; OR: risk measurements; *: Normal vs abnormal karyotype (excluded greater genetic events); M: mutated; U: not mutated;

FIG. 4A is a schematic representation of NPM gene; the dark blocks indicate encoding sequences; not colored blocks indicate 3'- and 5'-UTRs; MB is the metal binding domain; Ac: is the acid domain; NLS represents nuclear localization signal; NAB represents nucleic acid binding domain; dark arrows indicate the position on the map of primers for genomic DNA and not colored arrows indicate primers for cDNA amplification;

FIG. 4B shows wild-type NPM sequence (nucleotides 952-989) aligned with six mutant variants, named A to F; the capital letters indicate nucleotide insertions; the mutated protein sequence with C-terminal underlined tryptophan residues (W) is represented on the right, while the novel amino acid sequence common to all mutated proteins is indicated in the box area; for each variant, the total number of affected cases is given;

FIG. 4C shows sequencing of NPM from one patient hearing mutation A, as obtained by direct sequencing (on top) and after cloning and sequencing of the two variant alleles (middle, wild-type, bottom, mutated allele); the arrows indicate the position wherein allele diverges;

FIG. 4D shows the tridimensional reconstruction at confocal microscopy of NIH 3T3 cells transfected with plasmids encoding for EGFP-tagged wild-type (on top) and mutant NPM alleles (in the bottom); the wild-type protein localizes in the nucleoli and nuclear membrane, while the mutated NPM shows aberrant cytoplasmic localization;

FIG. 5A shows Western Blot (antibodies Sil-C vs 376) of whole lysed cells of NPMc+ or NPMc− leukaemic cells; Sil-C antibody specifically recognizes mutated NPM protein only in LAM cases with NPM mutation (NPMc+);

FIG. 5B shows Western Blot (Sil-C antibody) of a nuclear (N) and cytoplasmic (C) fraction in a leukaemic patient with the mutation A of NPM: Sil-C recognizes specifically mutated NPM protein in cytoplasmic fraction of NPMc+ primary leukaemic cells; results represent 3 independent experiments;

FIGS. 5C-5E show the osteomedullary biopsies of NPMc+ leukaemic cells with the mutation A: (5C) typical image of FAB-M5 acute myeloid leukaemia; the arrow indicates a big leukaemic cell with kidney-shaped nucleus; (5D) Sil-C antibody specifically recognizing the mutant (NPMm), shows a cytoplasm-restricted positivity (arrow); T indicates a bony trabecula; (5E) the anti-NPM 376 monoclonal antibody recognizes both wild-type NPM and mutated NPM protein and it stains the leukaemic cells in the cytoplasm and in nucleus (arrow);

FIGS. 5F-5G show osteomedullary biopsies of NPM mutations lacking promyelocytic leukaemia (NPMc−): (5F) typical morphology of a LAM-M3 (haematoxylin-eosin, ×400); (5G) Sil-C antibody doesn't stain M3 leukaemic cells and stains only vessel wall by cross-reactivity; the asterisk indicates the vessel lumen (APAAP technique; counterstaining in haematoxylin; ×400);

FIG. 6 shows the changes in 288 and 290 tryptophan and the creation of a NES motif in 40 mutant NPM proteins identified in leukaemic patients; Cit: cytoplasmic; nd: unavailable; IH: immunohistochemistry; amino acids in the panels: NES motif; underlined amino acids: tryptophan residues;

FIGS. 7A-B shows HI299 cells transfected with c-DNA encoding for NPMwt and NPM mutants from A to D in the absence (7A) and in the presence (7B) of Leptomycin B (LMB). eGFP-NPMwt is localized in nucleoli both in the presence and in the absence of LMB. In the absence of LMB, all the mutants associated with GFPs (from A to D) show the aberrant cytoplasmic localization (7A) while the same mutants associated with eGFP are completely replaced in the nucleus in the presence of LMB (7B);

FIGS. 7C-E shows the analysis at various time intervals of LMB effects on mutant A joined to eGFP (eGFP-NPMmutA) in NIH-3T3 cells: (7C) images at confocal microscopy of NIH-3T3 cells at the indicated times where the white circles represent the regions (regions of interest, ROI) in which the fluorescence intensity of eGFP-NPMmutA has been calculated; (7D) fluorescence measurement in selected areas (ROI) of NIH-3T3 cells; (7E) Western Blot analysis of sub-cellular distribution of eGFP-NPMmutA in NIH-3T3 cells using anti-GFP monoclonal antibody;

FIGS. 8 A-B show confocal microscopy experiments in order to verify the re-localization of NPM mutants in the nucleoplasm with Leptomicin B (LMB): (8A) confocal microscopy of NIH-3T3 cells transfected with GFP-mutA or with GFP-NPMwt in the presence or in the absence of LMB; under basal conditions, the mutant is localized only in cytoplasm (on top in the left) but it repositions in nucleoplasm (on top in the right) after incubation with LMB; GFP-NPMwt localizes in the nucleoli both in the presence and in the absence of LMB (middle panel, left and right); the lower panel shows cells treated with LMB and transfected with GFP-mutA and stained in nucleoli with anti-nucleolin monoclonal antibody (C23) (arrow); the mutant NPM protein (green) localizes in the nucleoplasm while the nucleolin/C23 (red) is restricted at nucleoli, the nuclear membrane is stained in blue; (8B) confocal microscopy of bone marrow of a NPMc+ leukaemia with mutation A of NPM (superior panel); the leukaemic cells show myeloid differentiation in medullary aspirate (on top in the left, arrow) and bony biopsy (on top in the middle); the leukaemic cells, mostly near to a bony trabecula (T), show cytoplasmic (and nuclear) NPM expression (on top in the right); in the middle and inferior panels purified leukaemic cells stained with anti-NPM 376 monoclonal antibody and observed at confocal microscopy in the absence (middle panel) and in the presence (inferior panel) of leptomycin B are shown; the images have been reconstructed in 3-D and an electronic cut on the nuclear surface has been carried out in order to better observe NPM localization. Under basal conditions the 376 monoclonal antibody that doesn't distinguish between NPM wild-type and mutant A, labels both the nucleoli and the cytoplasm (middle panel); after treatment with leptomycin B NPM is in nucleus again (inferior panel);

FIG. 9A shows the nuclear re-localization of mutant NPM by leptomycin B in OCI/AML3 cells: (9A) in the absence of LMB, the anti-NPM 376 antibody underlines both the nucleoli and the cytoplasm (left); the incubation with LMB determines a re-localization of NPM in the nucleoplasm (right);

FIG. 9B shows the immunoprecipitation (IP) of lysed cells of OCI-AML3 cells and U937 cells with control IgG or anti-NPMm rabbit antibodies (Sil-C) and anti-NPM murine antibody; Western blots with anti-Crml antibodies are shown in superior panels while those with anti-NPMm (Sil-C) and anti-NPM (CI-376) antibodies are shown in middle and inferior panels; WCL indicates OCI-AML3 lysed cells included as control; the figure shows the physical interaction between mutated NPM protein and Crm1;

FIG. 10 shows confocal microscope analysis of NIH-3T3 cells transfected with wild type eGFP-NPM or mutant eGFP-NPM and shows that NES and tryptophan mutations are both necessary for exporting NPM mutants; the destruction of NES structure in NPM mutant A (NPM mut A no-NES) prevents exportation from nucleus so that the mutant appears localized in the nucleoplasm both in presence and in absence of LMB; the NPM mutant E which possesses tryptophan 288 but lacks 290 one, repositions partially in nucleoli after treatment with LMB; the reinsertion of tryptophan 290 (NPM-mutA, A290W) produced about the same effect; when both tryptophans (288 and 290) have been inserted again in mutant A (C288W+A290W) the corresponding protein fused to eGFP, despite the presence of NES, is exclusively localized in nucleoli, both in presence and in absence of LMB;

FIG. 11A shows co-transfection experiments of murine cells with mutant A GFP-NPM and wild-type HA-NPM; NPM mutant acts as negative dominant versus wild-type NPM determining its partial moving in cytoplasm;

FIG. 11B shows Western blot with α-NPM or α-HA (left panel) and immunoprecipitation with an anti-Flag antibody and Western blot with α-NPM or α-HA (right panel); the biochemical data confirm those of labelling with fluorescent proteins;

FIG. 11C shows a hypothetical scheme of the mechanism of nucleus-cytoplasma altered localization of NPM mutant A and wild-type NPM, white not colored dots: tryptophan residues; dark dots: mutated tryptophans; square: Nuclear Export Signal (NES);

FIG. 12 shows the scheme of a NPM immunostaining approach for studying the acute myeloid leukaemia in which the cases are respectively divided in two groups for cytoplasmic (NPMc+) or nuclear (NPMc−) NPM expression;

FIG. 13 illustrates probe and primers used in RQ-PCR; two specific systems for mutations A and B are shown; the amplification strategy uses a primer forward (cNPM1-F) (SEQ ID NO:52) and a probe (c.Probe) (SEQ ID NO:55) common to both systems; the primer forward is positioned in exon 11 while the probe in the junction between exon 11 and exon 12; two reverses are cNPM-mut.A-R (SEQ ID NO:53) and cNPM-mut.B-R (SEQ ID NO:54) mutation-specific and are both designed in exon 12; the table indicates primers and probe sequences;

FIG. 14 shows the amplification plot in Plasmidic RQ-PCR related to 5 plasmidic dilutions tested in duplicate; the plasmid contains the sequence of NPM1 gene with the mutation A; the table shows the data reproducibility in further 4 experiments;

FIG. 15 shows the amplification plot of cDNA in RQ-PCR related to six serial dilutions on the strength of a factor equal to 10 of a sample of NPMc+ LAM with mutation A at diagnosis; the standard curve underlines "inclination", correlation coefficient and intercept with Y-axis; the table shows the diagnosis results achieved in 4 samples with mutation A and in 1 with mutation B; in all samples a "Maximum reproducible sensitivity" of $10^{-4}$ has been obtained;

FIG. 16 shows the monitoring of the mutated copy number of NPM, at diagnosis and after the induction treatment in 13 patients with NPMc+ LAM with mutation A (copy number expressed as copy number of NPM with mutation A/10000 copies of ABL);

(Abbreviation: CR=complete remission, PR=partial remission, NR=Not Response);

FIG. 17 shows the monitoring of mutated copy number of NPM, at diagnosis after the induction treatment and during the follow-up in 3 patients with NPMc+ LAM mutation A; the RQ-PCR shows a different kinetic in the diminution of copy number; within 50 day therapy all patients evidenced complete hematological remission but exhibited a different mutated copy number of NPM1; the patient I (square) shows a persistent hematological remission; a minimum mutated copy number is reached 90 days after the therapy and remains the same during the follow-up; in the patient 11 (diamond) the mutated copy number of NPM1 reaches a minimum around 100 days after the therapy; a decisive increase of the copy number is evident during the follow-up along with the hematological relapse around 200 days after the therapy; in the patient III (triangle) the mutated copy number of NPM1 reaches a minimum around 140 days after the therapy; a decisive increase of the copy number is evident during the follow-up along with the hematological relapse (not represented in figure) that occurred about one month apart (there isn't the molecular datum of relapse); (abbreviation: CR=complete remission).

EXAMPLE 1

Study of Gene Expression of NPM and of Diagnostic and Prognostic Value Thereof in LAMs A study that allowed to identify a large subgroup of acute myeloid leukaemias (about a third of the LAMs in the adult) characterized by the cytoplasmic NPM localization in leukaemic blasts, mutations of NPM gene, high frequency of normal karyotype, and good response to the induction chemotherapy, has been carried out.

Materials and Methods

Tumour Samples and Patients

The immunohistochemical studies have been carried out on 1845 paraffin embedded tumour samples. LAMs include: 591 primary LAMs (age 15-60, excluded M3 subgroup) of GIMEMA/EORTC study AML12 and 70 acute promyelocytic leukaemias, 69 primary and 135 secondary LAMs out of protocol. The remaining samples represent haemopoietic and extra-haemopoietic tumours other than LAM.

With informed approval, the osteomedullary biopsy of each patient with LAM has been fixed in B5, transferred in 70% alcohol, decalcified and included in paraffin.

Antibodies

Monoclonal antibodies against NPM (Cordell et al., 1999; Falini et al., 2002), that allow the protein identification on routine paraffin embedded sections have been employed. The biopsy samples have been also stained with monoclonal antibodies against the following molecules: nucleolin (C23) (Saint Cruz Biotechnology Inc., CA, USA), glicophorin, CD34 (DakoCytomation, Glostrup, Denmark), CD133 (Miltenyi Biotech, Bologna, Italy), and ALK (Falini et al., 1999).

Immunohistochemical Staining

Immunostaining has been carried out using the APAAP technique (Cordell et al., 1984). The sub-cellular NPM distribution (nucleus vs cytoplasm) has been assessed not knowing FAB subtype, cytogenetic or molecular biology. The cases have been classified as NPMc+ (positive cytoplasm) or NPMc− (negative cytoplasm). All cases have been stained in parallel for nucleolin (C23) that, as expected, in case of NPMc+, has shown a restricted nuclear expression.

Molecular and Cytogenetic Analysis

The cytogenetic investigations have been carried out after short-term cultures. The karyotypes have been analyzed after G-banding and have been described according to Human Cytogenetic Nomenclature of the International System (Mitelman, 1995). The FISH investigations have been carried out as previously described (Crescenzi et al., 2000).

The RT-PCR for the major fusion transcripts (PML-RARα, AML1-ETO, CBFB-MYH11, BC R-ABL and DEK-CAN), Southern Blotting, FISH analysis for MLL re-arrangements and analysis for FLT3 (ITD and D835) and MLL-ITD mutations have been carried out as previously described (Van Dongen et al., 1999; Soekarman et al., 1992; Noguera et al., 2002; tip et al., 1995).

Analysis of NPM Mutations

In the present study, the mutation analysis of NPM gene has been carried out in 161 cases of lympho-haemopoietic malignant tumours: 52 NPMc+ LAMs, NPMc-56 LAMs, 9 chronic myeloid leukaemias (CML), 7 acute lymphoblastic leukaemias (ALL) and 37 lymphoid neoplasias. Five patients with NPMc+ LAM have been analyzed both at diagnosis and in complete remission step after chemotherapy.

For analysis of the NPM coding region, one microgram RNA was retrotranscribed using the RT-PCR Thermoscript System (Invitrogen Corporation, Carlsbad, Calif., USA) and cDNA sequences were amplified with primers NPM1__25F, 5'-GOT TGT TCT CTG GAG GAG CGT TC-3' (SEQ ID No 36) and NPM1__1112R, 5'-CCT GGA CAA CAT TTA TCA AAC ACG GTA-3' (SEQ ID No 37) using Expand High-Fidelity Plus PCR system (Roche Applied Science, Mannheim, Germany).

In order to amplify exon 12 sequences from genomic DNA, two oligonucleotides were designed which specifically anneal to the flanking intron sequence regions (NPM1-F: 5'-TTA ACT CTC TGG TGG TAG AAT GM-3' (SEQ ID No 82) and NPM1-R: 5'-CM GAG TAT TTG CCA TTC CTA AC-3' (SEQ ID No 83)). PCR products were purified according to standard methods and sequenced directly from both ends. All mutations were confirmed in independent PCR products and, in representative cases, by cloning in pGEM-T Easy (Promega, Madison, Wis., USA) and sequencing.

Relationships Between NPM Mutations and Other Mutations

The normal karyotype LAM cases with NPM mutations of AMLCG 99 protocol were analyzed for the presence of other mutations, particularly FLT3-ITD, FLT3-D835, MLL-PTD, CEBPA, NRAS, and KIT.

Expression Vectors: Plasmid-Construction

To follow sub-cellular destiny of mutated and wild-type NPM protein in transfection experiments, plasmids expressing wild-type (pEGFPd-NPMwt) or mutant (pEGFPd-NPMmA) NPM alleles fused to the Enhanced Green Fluorescent Protein (EGFP) were generated. To this end, NPM cDNA sequences were amplified from a NPMc+ LAM patient (code 497A/30) carrying a heterozygous mutation in the gene exon 12 with primers NPM189F_BamHI, 5'GCC ACG GAT CCG AAG ATT CGA TGG AC3' (SEQ ID No 50), and NPM1__1044R_EcoRI, 5'ATC AAG AAT TCC AGA AAT GAA ATA AGA CG3' (SEQ ID No 51), and cloned in frame into pEGFP-C1 vector (BD Biosciences Clontech, Palo Alto, Calif., USA). Sequencing analysis confirmed the absence of Taq-introduced errors in both plasmids.

Transient Transfection Experiments

NIH 3T3 cells were transiently transfected with pEGFPd-NPMwt, pEGFPd-NPMmA and empty pEGFP-C1 vector using the Lipofectamin 2000 reagents (Invitrogen). Transfection efficiency was monitored by Western blotting. Images were obtained with a BioRad MRC 1024 confocal microscope after nuclei counter-staining with propidium iodide. The confocal slices were obtained with a SCI Octane workstation and the reconstruction of the images starting from confocal slices was been carried out using "Shadow Projection" module of Imaris software (Bitplane, Zurich, CH).

Statistic Analysis

Chi-square analysis in two-way contingency tables discloses the association between categorical variables. Statistical differences between means were analyzed by t-test. The relationship between NPM localization and FLT3-ITD/D835 mutations, adjusted for age and cytogenetics, was investigated applying a logistic regression model with these factors as independent variables and NPM as dependent variable. Cases with major translocations were excluded because their absolute association with nucleus-restricted NPM expression don't provide a valid parameter estimate.

The association between clinical and biological features (white blood cell count at presentation, NPM sub-cellular expression, FLT3 mutations) and response to induction therapy was valued in 126 normal karyotype LAM (79 NPMc+ and 47 NPMc−) treated according to the GIMEMA LAM99P protocol. A multivariate Logistic model was applied. In all the statistic analyses in two-way, two values of p<0.05 were considered of statistic importance.

Results

Cytoplasmic Localization of NPM

Cytoplasmic NPM expression, defined as NPMc+ (FIG. 1A), was found in 208/591 (35.2%) primary LAM cases of the GIMEMA/EORTC study (FIG. 1B). Such find appears specific for primary LAMs, not being detectable in secondary LAMs and in other human tumours that show always an exclusive nuclear NPM expression (FIG. 1B). In NPMc+ leukaemic cells, nucleolin (C23), another nucleolar antigen, retains its nucleus-restricted localization as showed in FIG. 1A. In NPMc+ LAMs, the anomalous NPM expression is usually found in almost all leukaemic cells; except in cases of M5b (monocytic leukaemia), where cytoplasmic NPM is expressed only in a variable percent of the neoplastic population, namely 30-60% of leukaemic cells, preferentially those more immature (monoblasts). In contrast, NPMc− LAMs rarely contain NPMc+ leukaemic cells, mostly mitotic elements as shown in FIG. 1A on the right.

The anomalous cytoplasmic NPM expression of leukaemic cells must be considered a long-term event, as documented by its comparison in 25 patients with NPMc+ LAM in relapse of disease up to 3 years after the initial diagnosis.

Morphology of NPMc+ LAM

Morphology of NPMc+ LAM

The anomalous cytoplasmic NPM expression was found in all FAB categories, except M3 (acute promyelocytic leukaemia), M4eo (acute myelomonocytic leukaemia with eosinophilia), and M7 (acute megakaryocytic leukaemia) as shown in FIG. 1C. Particularly, the figure shows the correlation between NPM sub-cellular expression and morphology in 591 primary LAMs of GIMEMA/EORTC study plus 70 acute promyelocytic leukaemias with t(15;17) (out of protocol). The frequency of cytoplasmic NPM expression ranged from 13.6% in MO (minimally differentiated LAM) to 93.7% in M5b (acute monocytic leukaemia). Most NPMc+ LAM of M5b and M6 (acute erythroid leukaemia) type and about 30% of NPMc+ M1 (LAM without maturation), M2 (LAM with maturation) and M4 cases are characterized for the presence of cytoplasmic NPM not only in myeloid blasts but also in erythroid precursors, particularly in the proerythroblasts (FIG. 1D) and, less frequently, in the megakaryocytes (not shown data).

The presence of cytoplasmic NPM in different hematopoietic lineages led to the expression analysis of some molecules, as CD34 and CD133 antigens, which occur on hematopoietic stem cells. CD34-positivity (defined as 20% positive cells) was detected in 12/159 (7.5%) NMPc+ LAM and in 227/317 (71.6%) NMPc− LAM (p<0.001) as shown in FIGS. 2A-2E. Therefore NPMc+ appears mutually exclusive with CD34 and CD133 expression. CD34-negative NMPc+ LAMs characteristically also lacking CD 133, as shown in FIG. 2F.

The wide morphological spectrum and the involvement of various hematopoietic lineages of the NPMc+ LAM reflects a possible origin thereof from CD34−/CD38− rare hematopoietic stem cells, which were identified in several animal species, included murine and human species (Goodell et al., 1997; Engelhardt et al., 2002). Alternatively, CD34 could be unregulated as effect of the leukaemic transformation.

Karyotype of NMPc+ LAM

Cytogenetic data are available in 493/591 cases of LAM (166 NPMc+ and 327 NPMc−). Over 85% (142/166) of NPMc+ LAM has a normal karyotype as shown in FIG. 3A. In contrast, only 26.9% (88/327 cases) of NPMc− LAM has a normal karyotype (p<0.001). Overall, 61.7% of normal karyotype LAM are NPMc+ (142/230 cases) as shown in FIG. 3B. 24 NPMc+ LAM cases show the presence of smaller chromosomal translocations and, among these, 12 (50%) cases have both normal and abnormal metaphases.

None of the LAM cases carrying major genetic abnormalities is NPMc+, as shown in FIGS. 3B, 3C and 3D.

FLT3-ITD and Other Genes Mutations in NPMc+ LAM

FLT3, ITD or D835 mutations were detected in 591219 (26.9%) and 13/202 (6.4%) LAM cases with a normal karyotype, respectively; one case is carrier of both ITD and D835 mutations. FLT3-ITD mutation was 2.5 fold more frequent in NPMc+ cases than NPMc− cases (p<0.003), as shown in histograms of FIG. 3E. A multivariate logistic regression model adjusted for age and cytogenetics allows to establish an independent association between cytoplasmic NPM (dependent variable) and FLT3-ITD, as shown in FIG. 3G. No statistical association is observed between FLT3-D835 mutations and NPM sub-cellular localization (p=0.5), possibly because of low number of D835-mutation cases.

In a subsequent study on cases of AMLCG 99 protocol (Schnittger et al., 2005), an increased FLT3-ITD mutation frequency in LAM cases with NPM mutation was confirmed. In contrast, NPM mutation is rarely associated to MLL (MLL-PTD) and CEPBA mutations.

Response to Induction Therapy of NPMc+ LAM

Response to induction therapy was evaluated in 126 LAM cases with normal karyotype (79 NPMc+ and 47 NPMc−) treated according to the GIMEMA LAM99P protocol. In table 1 is shown logistic regression model of the response to induction therapy in 126 patients.

TABLE 1

| Parameter | Analysis of maximum-likelihood assessment | | | | | Odds Ratio Assess | | |
| --- | --- | --- | --- | --- | --- | --- | --- | --- |
| | DF | Assess | Stand. Error | Wald Chi-square | Pr > Chi-square | OR | 95 OR Confidence range | |
| Intercept | 1 | 0.9596 | 0.3761 | 6.5112 | 0.0107 | | | |
| FLT3 (M vs U)* | 1 | −0.4020 | 0.4541 | 0.7836 | 0.3760 | 0.669 | 0.2 | 1.6 |
| NPM (Cit vs Nucl)# | 1 | 1.0946 | 0.4647 | 5.5486 | 0.0185 | 2.988 | 1.2 | 7.4 |
| WBC (≦80 vs >80) | 1 | −1.3123 | 0.4748 | 7.6399 | 0.0057 | 0.269 | 0.1 | 0.6 |
| Age (≦48 vs >48) | 1 | −0.3405 | 0.4498 | 0.5732 | 0.4490 | 0.711 | 0.2 | 1.7 |

Cit. = cytoplasmic positivity; Nucl. = nucleus-restricted positivity.
*M = Mutated; U = Not mutated; WBC: number of white blood cells;

The multivariate model for complete response achievement includes white blood cell count (categorized at the 75$^{th}$ percentile), age (categorized at median value), NPM sub-cellular expression and FLT-3 mutations. Analysis is shown in table 1 and shows that the white blood cell count and NPM are both independent prognostic factors. Particularly as negative prognostic factor impinges a white blood cell count over 80×10$^9$/L (p<0.006; OR=0.269; CI 95%:0.1-0.6) and as positive prognostic factor the fact that leukaemic cells have cytoplasmic NPM (p<0.019; OR=2.988; CI 95%:1.2-7.4).

NPM Mutations as Prognostic Factor in Normal Karyotype LAMs

According to the presence of NPM gene and FLT3-ITD gene mutations, normal karyotype LAMs can be divided in 4 subgroups: mutated NPM/mutated FLT3, mutated NPM/not mutated FLT3, not mutated NPM/mutated FLT3 and not mutated NPM/not mutated FLT3. The analysis carried out by the authors on 401 LAM cases with normal karyotype (Schnittger et al, 2005) shows that the presence of a NPM mutation in absence of a FLT3 mutation identifies a subgroup of leukaemias with more favorable prognosis. Similar results were reported subsequently also in other two studies (Dhoner et al., 2005; Verhaak et al., 2005).

Analysis of NPM Mutations in LAMs and in Other Tumours

NPMc+ LAM doesn't express NPM-ALK, NPM-RARα, NPM-MLF1 fusion proteins, or other fusion proteins containing NPM, as shown by absence of respective fusion genes upon FISH, absence of respective fusion transcripts upon RT-PCR, absence of said fusion proteins upon immunohistochemistry, exclusive presence of 38 kDa NPM polypeptide upon Western Blotting, and demonstration of cytoplasmic NPM through four different anti-NPM monoclonal antibodies.

In the present study, analysis of the NPM coding region, carried out by RT-PCR and direct sequencing, revealed mutations affecting exon 12 in all but one NPMc+ case. FIG. 4A is a schematic representation of the NPM gene, and mutations are summarized in FIG. 4B. In total, six different sequence variants were observed, all of them leading to a frameshift in the region encoding for the carboxyl-terminus domain of the NPM protein. The most frequent mutation (type A: gatctctgTCTGgcagtggagga agtctctttaagaaaatag (SEQ ID No 57)) is a duplication of a TCTG tetranucleotide at positions 956-959 of the reference oligonucleotide sequence NM_002520 (GenBank) as shown in FIG. 4C; the resulting shift in the reading frame is predicted to alter the C-terminal portion of the NPM protein by substituting the last seven amino acids (WQWRKSL(SEQ ID No 58)) with 11 different residues (CLAVEEVSLRK(SEQ ID No 59)). Three additional mutations (type B: gatctctgCATGgcagtggaggaagtct cttaagaaaatag (SEQ ID No 60), type C: gatctctgCGTGgcagtggaggaagtct ctttaagaaaatag (SEQ ID No 61), and type D: gatctctgCCTG-gcagtggaggaagtct ctttaagaaaatag (SEQ ID No 62)) include distinct 4-base pair insertion at position 960, all resulting in the same frameshift as mutation A. In the last two mutations (type E: gatctctggcagtCTCTTGCCC aagtctctttaagaaaatag (SEQ ID No 63) and type F: gatctctggcagtCCCT GGAGAaagtctctttaagaaaatag (SEQ ID No 64)), nucleotides 965-969 (GGAGG) are deleted and in place of them, two different 9-base pair sequences are inserted, not modifying the frameshift and creating a new carboxyl-terminus domain of 9 amino acids. Regardless of the specific type of mutation, the mutants are characterized by replacement of at least one of the two tryptophan residues (W) that in wild-type sequence are at position 288 and 290. The obtained results are according to previous evidences in studies carried out on mice that show the importance of tryptophan amino acid for nucleolar localization (Nishimura et al., 2002). In addition, all mutant proteins shared the same last 5 amino acid residues VSLRK (SEQ ID No 29). Thus, despite genetic heterogeneity, all NPM gene mutations result in a novel sequence in place of the NPM protein C-terminus.

The presence of mutations in the NPM exon 12 and their specific association with NPMc+ LAM was confirmed in 11 samples also by sequencing analysis of genomic DNA. NPM mutations are heterozygous and occur only in the malignant clone, as they are not present in bone marrow samples from patients in complete remission (N=5) after chemotherapy. Mutations are observed in NPMc+ LAM of all FAB categories, included NPMc+ cases with abnormal karyotype or CD34 expression. Conversely, all 56 of the NPMc-LAMs as well as 53 malignancies other than LAM, and NPMc− display wild-type NPM sequences as shown in table 2.

TABLE 2

| Tumour type | N. | FAB | CD34+ | Mut. FLT3 | Mut. NPM |
| --- | --- | --- | --- | --- | --- |
| LAM NPMc+ | 52 | | | | |
| normal karyotype | 49 | All* | 2/49 | 25/46 | 48/49 |
| Abnormal karyotype | 3 | M1, M5b | 1/3 | 1/3 | 3/3 |
| LAM NPMc− | 56 | | | | |
| normal karyotype | 12 | M1-M6 | 8/10 | 4/12 | 0/12 |
| Abnormal karyotype** | 44 | M1-M6 | 5/8 | 3/8 | 0/44*** |
| LMC | 9 | n.a. | 0/9 | n.d. | 0/9 |
| Lymphoid neoplasias | 44# | n.a. | n.d. | n.d. | 0/44 |

*Except for M3, M4eo and M7.
**includes 7 t(15; 17 s); 12 t(8; 21 s); 13 Inv(16); 1 MLL rearrangement; 1 inv(3; 1 t(6; 9), a complex karyotype;
***Case with Inv 16 that shows a deletion of three nucleotides in exon 6 of NPM1 at positions 583-585 without involving 3' terminal.
includes: 7 acute lymphoblastic leukaemias; 7 lymphocyte B chronic lymphatic leukaemias; 5 mantellari lymphomas; 5 follicular lymphomas; 10 big cells B lymphomas; 5 Burkitt lymphomas; 5 multiple myelomas.
Mut.: mutated;
n.a.: not applicable;
n.d.: undone.

In subsequent studies, the authors confirmed afore described results for 1009 LAM cases subjected to sequencing of NPM gene. FIG. 6 shows 40 NPM mutations till now individualized.

Transfection of the Mutated NPM Gene

To confirm whether the NPM exon 12 mutations are responsive for cytoplasmic dislocation of the NPM protein, NIH 3T3 cells were transiently transfected with expression vectors encoding for the wild-type and mutant allele fused with EGFP. Confocal microscopy showed the expected nucleolar localization for the EGFP-NPM wild-type protein, whereas the NPM mutant isoform is clearly dislocated into the cytoplasm as shown in FIG. 4D.

These results indicate clearly a causal correlation between the genetic event (NPM mutations) and the cytoplasmic localization of the NPM protein. In addiction, the fact that mutated NPM is closely associated with the normal karyotype and is not seen in leukaemias with major cytogenetic abnormalities suggests that the NPM mutation is the primary leukaemogenic event. The mutation might interfere with the normal function of NPM, such as, for example, interaction with the Arf or p53 protein, (Colombo et al., 2002; Kurki et al., 2004; Horn et al., 2004). Mutations might also perturb other NPM functions that have been mapped within C-terminal domain, such as nucleic acid binding (Hingorani et al., 2000), ATP (Chang et al., 1998), DNA-polymerase alpha-stimulatory activity, or binding with the tumour suppressor gene Arf (Bertwistle et al, 2004).

EXAMPLE 2

Production of Specific Antibodies Against Polypeptide Sequences of C-Terminal of the Leukaemia-Specific NPM The polypeptide sequences represent ideal immunogenes for the production of specific antibodies that include all types of polyclonal and monoclonal antibodies, human monoclonal antibodies, and humanized antibodies produced by genetic recombination techniques.

The peptides corresponding to A, B, C, D, E and F sequences of FIG. 4B can be synthesized chemically according to standard procedures.

Every animal species is employable for antibody preparation. Methods for the antibody production and immunization procedure of animal species (inoculation routes of antigen, use of Freund adjuvant to increase the immunogenetics of injected mixture, frequency of immunizations, etc) are largely described in the scientific literature.

Monoclonals

Balb/c Mice can be inoculated by intraperitoneal route with specific peptides bound to KLH (3 immunizations of 150 micro grams of peptide every 10 days). Such immunization program is followed by an intravenous booster (150 micro grams), three days before the fusion, with the purpose to increase immune response to the maximum.

Monoclonal antibodies can be produced with the "hybridoma method" (Goding J., 1983) that consists in the formation of hybrid cells resulting from spleen normal cells with myeloma cells. The authors of the present invention use the P3-NS1-Ag-4-1 myeloma lineage (abbreviated as NS-1) provided them from Prof. David Y Mason laboratory, Oxford, and deriving from P3K lineage, which synthesizes only a light chains that are not secreted but degraded internally and lack HGPRT enzyme.

Following the cellular fusion, the hybrid selection is carried out with addition of hypoxanthine, aminopterin and thymidine (HAT) to the medium. The only cells able to survive under this condition possess:

1. myeloma neoplastic characteristic of growing in vitro;
2. hypoxanthine guanidine phosphoribosil transferase enzyme (HGPRT) of spleen cells that allows them to use hypoxanthine and thymidine for synthesizing nucleotides and therefore DNA.

Not fused myeloma cells die because the lack HGPRT enzyme and therefore cannot use hypoxanthine for biosynthesizing nucleotides, while spleen cells die (even if they are HGPRT$^+$) because they are unable to grow in vitro.

For purposes of the present research, the hybridoma supernatant can be tested directly on cytological samples or on paraffin embedded sections of LAM samples containing mutated form of NPM (NPMc+ LAM) and normal form (wild-type) of NPM (NPMc– LAM). The rational criterion of screening is the identification of hybridomas producing specific monoclonal antibodies against peptides of the invention (corresponding to C-terminal of NPM), namely antibodies reacting with NPMc+ LAM but not with NPMc–. Such antibodies have the advantage that can be used both on cytological samples (smears and cytocentrifugates) and on paraffin embedded tissue sections and, in addiction, both for diagnostic purpose and for monitoring leukaemic minimal residual disease. After identification, hybrids can be cloned according to well known methods ("limiting dilution") and grown in vitro in large amounts. Clones can be then cryostored in liquid nitrogen so that to have an available "bank" of the aforesaid antibodies.

Polyclonal Antibodies

Polyclonal antibodies against peptides of the present invention (specific sequences of C-terminal of mutated NPM) can be produced in several animal species. Polyclonal antibodies are referred both to whole animal serum containing such antibodies and to serum fractions enriched in antibody.

Particularly, IgG or IgM serum fractions that contain only the specific antibodies for peptides of the present invention, can be obtained by eluting serum through a column containing bonded peptides of the present invention (affinity chromatography) and subsequently purifying this fraction by a column containing protein A or protein G. These antibodies have the advantage that can also be used on cytological samples (smears and cytocentrifugates) and not only on paraffin embedded tissue sections, and for monitoring leukaemic minimal residual disease in addiction to diagnostic purpose.

Production of Sil-C Polyclonal Antibody

Materials and Methods

The Sil-C antibody was produced by immunizing the rabbits with a 11 amino acid synthetic peptide (NHCOCH3-CLAVEEVSLRK-COOH (SEQ ID No 59)) (Inbio Ltd, Tallin, Estonia) which comprises two mutated tryptophans, a NES portion and the VSLRK peptide (SEQ ID No 29) of mutant A. The rabbit sera were purified by affinity chromatography using columns containing the peptide used as immunogen (elution with 0.23 M Tris, 0.2 M $Na_2HPO_4$, pH 0.8). The reactivity against the peptide was shown by ELISA technique. Particularly, the ELISA plates were adsorbed overnight at 4° C. with 50 µl of peptide at a concentration of 10 µg/ml in TBS. After the blocking with PBS containing 3% bovine fetal serum, the rabbit serums were added at increasing dilutions to the wells (from 1/100 up to 1/72900). After the washing in PBS-Tween 20 (0.05%), to each well were added 50 µl of a secondary goat antibody conjugated with peroxidase (dilution 1/5000 in PBS).

The antibody-antigen reaction was observed adding to each well 50 µl of O-phenylenediamine dihydrochloride. The reading was carried out at 492 nm. Pre-immune serums were used as negative control. The biochemical characterization of antibodies was carried out with standard Western blotting, immunoprecipitation and co-precipitation techniques.

Results

A polyclonal antibody (named Sil-C), which recognizes specifically an antigenic epitope comprising two mutated tryptophans, a NES portion and the VSLRK peptide (SEQ ID No 29) belonging to mutated nucleophosmin proteins (NPM) as defined in attached claims 1-6, was produced.

In Western blotting experiments, Sil-C antibody recognizes a 37 kDA specific band only in whole lysed cells from leukaemias with NPM mutations (NPMc+ LAM) (patients 1-3) but not from patients with LAM without NPM mutations (NPMc−) (cases 4-6) (FIG. 5A, on top in the left). In contrast, the monoclonal anti-NPM 376 antibody reacting with both wild-type and mutated NPM, identifies a 37 kDA band in all tested leukaemic patients, regardless of the presence or not of mutations of NPM gene (FIG. 5A, in bottom on the left). In patient No. 2, carrier of a NPM mutation type A, Sil-C antibody recognizes a 37 kDa band only in the cytoplasmic fraction of leukaemic cells (FIG. 5B, on top in the right). The picture, as expected, differs from that of the monoclonal 376 antibody which identifies a band with the same molecular weight, both in lysed cytoplasmic fraction and in those of the nuclear fraction (FIG. 5B, in bottom in the right).

These biochemical data were also confirmed at cytological level by immunohistochemical staining of medullary biopsies from 10 patients with NPMc+ LAM. In these samples, the monoclonal anti-NPM antibodies, recognizing both normal and mutated NPM, identify NPM both in nucleus, and in cytoplasm (FIG. 5E). In contrast, Sil-C antibody identifies exclusively NPM protein at cytoplasmic level (FIG. 5D). The specificity of this reaction is clearly shown by the fact that: i) it is completely abolished from the pre-incubation of Sil-C antibody with the peptide used as immunogen; ii) Sil-C antibody doesn't stain biopsy samples of patients with NPMc− LAM, namely lacking NPM mutations (FIGS. 5F and 5G).

These results show that Sil-C antibody recognizes specifically NPM mutants and that the mutants are restricted exclusively in the cytoplasm of leukaemic cells that containing NPM mutations. The availability of specific antibodies against leukaemic NPM mutants opens new perspectives from a diagnostic and therapeutic standpoint.

From a diagnostic standpoint, these reagents could be employed for the diagnosis at the beginning and also for monitoring minimal residual disease in combination with techniques of quantitative PCR (see below).

From a therapeutic standpoint, it is supposable the use of intracellular antibodies ("intrabodies") able to inhibit the leukaemic NPM mutated proteins without damaging the function of physiological NPM protein.

EXAMPLE 3

Preparation of Vaccines

The vaccines can be administered in formulations recognized by "T cell receptor" (mononuclear cells from peripheral blood) or presented by anti-gen-presenting cells (e.g. dendritic cells, cells B, macrophages).

In this context the term "vaccine" means any substance or compound that serves to induce anti-tumour immunity anti-tumour immunity means cytotoxic responses (T cellular), induction of antibodies that recognizes tumour cells and production of cytokines with anti-neoplastic activity. The anti-tumour activity can be measured in vitro (cytotoxicity) or in vivo in experimental animal models.

Efficacy of the anti-tumour vaccines is known to be increased when various polypeptides, in combination, having different structures, are used. Therefore to that end anti-LAM NPMc+ vaccines can contain different synthesis polypeptides with different specificity and sequences provided they induce the recognition of tumour cells containing NPM gene mutations.

The vaccine of this invention can be conjugated with immunogenic molecules universally known as carriers.

It can contain, in its formulation, suitable solutions for inoculum (physiological saline, various saline solutions) and excipients.

In addition, the vaccine can contain or be administered with adjuvants, namely any molecule with immunostimulant activity. The adjuvant administration can be carried out in any time point preceding or following inoculum of anti-tumour vaccine.

The vaccine of the present invention can be administered by systemic or local route in single or multiple dose.

The evaluation of the immune response will be carried out according to the methods well known and described in scientific literature. Particularly, after vaccine inoculum, anti-gen epitopes are presented to B and T cells by anti-gen-presenting cells.

Therefore the determination of cytotoxic responses can be carried out on both CD4+ and CD8+ cells T, and all cellular populations able to induce cytolysis or apoptosis (e.g. neutrophiles, NK cells). Specifically, the activation, (immunophenotype), proliferation ability, (by methods of incorporation of radioactive markers), cytotoxic ability on opportunely prepared targets, ability to secrete cytokines (ELISA, ELISPOT methods) thereof can be measured.

As to antibody responses these can be measured in vitro or in vivo with experiments of serum transfer and inhibition of the tumour growth.

The efficacy in vivo in animal models can be measured according to statistic significance criterions verifying the anti-tumour response in opportunely designed control groups.

Object of the evaluation will be survival, measurement of tumour biomarkers, inhibition of the growth of tumour cells, regression of tumour masses, reduction of tumour-induction ability.

EXAMPLE 4

Study of Mechanism of Cytoplasmic Accumulation of NPM Mutants

The present applicants elucidated the molecular mechanism that leads to the aberrant cytoplasmic accumulation of NPM in NPMc+ acute myeloid leukaemia.

Materials and Methods

Cells for Transfection, AML Samples and OCI/AML3 Cellular Line

For transfection experiments, NIH-3T3 and H1299 cells were used. Leukaemic cells from 5 leukaemic patients (3 of which carrying the mutation A of NPM and 2 carrying wild-type NPM gene), were isolated by separation with Ficoll-Hypaque and used for biochemical studies and confocal microscope analysis. Biopsies of bone marrow (n=373) and pellet of blasts of peripheral blood (n=20), from 393 patients with AML of the GIMEMA AML 99P and GIMEMA AML12/EORTC protocol, were fixed in B5 and included in paraffin. OCI/AML3 cellular line, which we identified as the only containing the mutation A in exon 12 of NPM gene (among 79 tested myeloid human lines) (Quentmeier et al., 2005) was grown in alpha-MEM with 10% FBS plus glutamine and antibiotics at standard concentrations.

Mutational Analysis of NPM Gene

Studies were carried out on leukaemic cells of 393 adult ALM patients of the GIMEMA AML99P and GIMEMA AML12/EORTC protocol. The selection of cases for mutational analysis was carried out based on material availability for NPM immunohistochemical identification. The mutations of exon 12 of NPM gene were analysed with RT-PCR and sequencing as previously described or using DHPLC (Wave™ System, Transgenomic Inc., Omaha, Nebr.; USA).

Plasmid Construction

The mutants A, B, C, and D of NPM were produced by PCR using NPMwt as template; the same forward primer (5' CGC CAC GCT AGC GAA GAT TCG ATG GAC) (SEQ ID No 65) was used and a different reverse primer for each mutant (mutant A-5': CTA TTT TCT TAA AGA GAC TTC CTC CAC TGC CAG ACA GAG ATC TTG AAT AGC CTC TTG G (SEQ ID No 66); mutant B-5': CTA TTT TCT TAA AGA GAC TTC CTC CAC TGC CAT GCA GAG ATC TTG AAT AGC CTC TTG G (SEQ ID No 67); mutant C-5': CTA TTT TCT TAA AGA GAC TTC CTC CAC TGC CAC GCA GAG ATC TTG AAT AGC CTC TTG G(SEQ ID No 68); mutant D-5': CTA TTT TCT TAA AGA GAC TTC CTC CAC TGC CAG GCA GAG ATC TTG AAT AGC CTC TTG G (SEQ ID No 69)). The products of the respective PCRs were cloned in pcDNA3.1/NT-GFP-TOPO (Invitrogen, Carlsbad; Calif., USA), and checked with insert sequencing. To produce the double N-terminal flag-HA tag in plasmids with wt NPM and mutation A, a PCR was carried out using as template wild-type NPM or mutant A; as forward and reverse primer were respectively used 5' CGC CAC GCT AGC GAA GAT TCG ATG GAC (SEQ ID 65) and 5' TCA AGA ATT CCA GAA ATG AAA TAA GAC (SEQ ID No 70). The PCR product was digested using NheI and ECORI, and the fragment was subcloned in PCIN4 vector, containing the Flag-HA tag at N-terminal end of the fragment. The precision of Flag-HA-NPM-wt and Flag-HA-NPM-mutant A sequences was confirmed by sequencing.

NPM mutants E, G and R were produced through QuikChange Fine Site-Directed Mutagenesis Kit (Stratagene, You Jolla, Calif.), using as template pEGFP-C1-A/PMwt, and according to manufacturer instructions. Primers were designed on the followings sequences:

```
NPM_MUT_E:
                                        (SEQ ID No 71)
5'-GATCTCTGGCAGTCTCTTGCCCAAGTCTCTTTAAG-3';

NPM_MUT_G:
                                        (SEQ ID No 72)
5'-GATCTCTGGCAGTGCTTCGCCCAAGTCTCTTTAAG-3';

NPM_MUT_R:
                                        (SEQ ID No 73)
5'-GATCTCTGGCAGAGGATGGAGGAAGTCTCTTTAAG-3'.
```

NPM_MUT_A A290W, NPM_MUT_A C288W+A290W, e NPM_MUT_A_NO_NES plasmids were produced using pEGFP-C1-NPMmA as template, exploiting the localization of mutagenesis sites between cutting sites of BglII and EcoRI enzymes. By using a partially complementary primer couple, containing the desired mutation and protruding ends compatible with ends produced by the digestion with BglII-EcoR, it was possible to ligate the double strand DNA produced by annealing primers to pEGFP-C1-NPMmA vector previously digested using the two above restriction enzymes.

The sequences of the used primers are:

```
NPM_MUT_A A290W_FOR:
                                        (SEQ ID No 74)
5'-GATCTCTGTCTGTGGGTGGAGGAAGTCTCTTTAAGAAAATAGG-3';

NPM_MUT_A A290W_REV:
                                        (SEQ ID No 75)
5'-AATTCCTATTTTCTTAAAGAGACTTCCTCCACCCACAGACAGA-3';

NPM_MUT_A C288W + A290W_FOR:
                                        (SEQ ID No 76)
5'-GATCTCTGGCTGTGGGTGGAGGAAGTCTCTTTAAGAAAATAGG-3';

NPM_MUT_A C288W + A290W_REV:
                                        (SEQ ID No 77)
5'-AATTCCTATTTTCTTAAAGAGACTTCCTCCACCCACAGCCAGA-3'

NPM_MUT_A_NO_NES_FOR:
                                        (SEQ ID No 78)
5'-GATCTCTGTGGAGCAGGGGAGGAAGGCTCTTTAAGAAAATAGG-3';

NPM_MUT_A_NO_NES_REV:
                                        (SEQ ID No 79)
5'-AATTCCTATTTTCTTAAAGAGCCTTCCTCCCCTGCTCCACAGA-3'.
```

Every construct was verified by sequencing.

Inhibition of the CRM 1-Dependent Nuclear Exportation

The H1299 cells were seeded on the surface of six-well plates 24 hours before transfection. 5 μg of expression vector encoding for wild type HA-NPM, GFP-NPM-mutant A, or both, were transfected using the precipitation method with calcium-phosphate. After 24 hours, the cells were treated with 20 nM leptomycin B, a Crm1 specific inhibitor (Sigma, St. Louis, Mo., USA) for 8 hours or not treated, respectively. The cells then were fixed in 4% paraformaldehyde for the immunofluorescence study.

NIH-3T3 cells were transfected using Lipofectamin 2000 (Invitrogen Carlsbad, Calif., USA) following the manufacturer instructions. After 24 hours, the cells grown on the slide were incubated with cycloeximide (Merck Biosciences Ltd, Nottingham UK) 10 micro grams/ml (30 minutes) and leptomycin B (Merck Biosciences Ltd, Nottingham UK) 20 ng/ml (5 hours), or other Crm1 inhibitors such as ratjadons A and C (Alexis Biochemicals, Carlsbad, Calif., USA) 20 ng/ml (5 hours).

The cells were fixed in 4% paraformaldehyde (10 minutes) for immunofluorescence and confocal microscope analysis.

For "time course" experiments, transfected cells were transferred inside an Attofluor chamber (Molecular Probes, Eugene, Oreg., USA) and were observed using a MRC-1024 confocal apparatus (Biorad Cambridge, UK) assembled on an Olympus IMT-2 microscope. The images of a single section were recorded before and after the addition of leptomicin B, at 60 second intervals, using the time-series function of Laser-Sharp program (BioRad). The excitation wavelength was 488 nm and images were detected using a filter from 505 to 550 nm on the PMT2.

The images were processed and analysed using the well known ImageJ program (Rasband WS, Image J, U.S. National Institutes of Health, Bethesda, Md., USA, http://rsb.info.nih.gov/ij/, 1997-2005).

For western-blotting analyses of the sub-cellular distribution of GFP-NPM mutant A protein, NIH-3T3 cells transfected with GFP vector or with GFP-NPM mutant A, as described above, were incubated with leptomicin B 20 ng/ml (or with methanol as control) without cycloeximide for 3 or 6 hours. Then cells were harvested, washed with PBS and lysed in hypotonic buffer according to the method of Schreiber et al. (1989). The supernatant was preserved as cytoplasmic fraction. The pellet, containing nuclei, was again washed with the hypotonic buffer, then solubilised in a hypertonic buffer and boiled in a solution containing SDS before loading.

Equivalent dilutions (with the same cell number) of cytoplasmic and nuclear fractions were loaded, blotted on nitrocellulose and incubated with an anti-GFP monoclonal antibody (Roche, Indianapolis, Ind., USA) for Western-blot analysis of the distribution of GFP-NPM mutant A.

Cells deriving from two patients with NPMc+AML (carrying the mutation A) and from OCI/AML3 cellular line were harvested in medium ($10^6$ cell/ml in 24-well plates) and incubated at 37° C. with 5% $CO_2$ for 5 hours. After the incubation overnight with leptomycin B (20 ng/ml), the cells were washed with PBS and centrifuged. The cell pellet was fixed in B5 and paraffin for the immunostaining.

Immunostaining Procedures

The DAPI staining was used to visualise nucleuses of H1299 cells transfected with the GFP-NPM-mutant A and with GFP-NPM wt. For Flag-HA constructs, the fixed cells were made permeable with 0.2% Triton-X 100 (10 minutes) followed by blocking with 10% anti-goat serum (30 minutes). Then primary anti-HA antibody was added (1:1000, Roche Indianapolis, Ind., USA) for 1 hour followed by incubation for 30 minutes with the secondary Alexa-568 antibody (1:1000, Molecular Probes, Oregon, USA). The images were taken using a digital camera with the Spot 4.09 program (Diagnostic Instruments, Sterling Heights, Mich., USA).

The nuclei of NIH 3T3 cells transfected with GFP-NPMwt and GFP-NPM mutant A were stained with propidium iodide. The nucleolin staining (C23) of NIH-3T3 cells was carried out with the primary anti-nucleolin antibody purchased from DakoCytomation (Glostrup, Denmark), followed by Texas Red conjugated secondary antibody (Southern Biotechnology Associates, Birmingham, Ala.); the nuclei were contrastained with the TO-PRO-3 (Molecular Probes, Oregon, USA).

The NPM coloration of paraffin embedded sections of AML cases containing the mutation A was carried out with monoclonal anti-NPM antibodies followed by a Alexa 488 conjugated secondary (Molecular Probes, Oregon, USA); the nuclei were contra-stained with propidium iodide. The images were taken with a confocal microscope Zeiss LSM 510 (Carl Zeiss, Jena, Del.), using laser excitation wavelengths at 488 nm (for ALexa 488), 543 nm (for Texas Red and the propidium iodide) and 633 nm (for TO-PRO-3), respectively. The laser intensity tuning, diameter of pinholes, and configuration of the light detection were set to achieve the best signal/noise ratio and avoid fluorescence crossover. The images were then transferred to a SGI Octane workstation (Silicon graphics, Mountain View, Calif., USA) for further elaboration; 3D reconstruction was made with the shade or iso-surface method using the Imaris program (Bitplane, Zurich, CH).

NPM research on paraffin embedded sections using alkaline phosphatase method was done for 393 patients as previously described. The samples were classified as cytoplasmic or nuclear NPM without knowing the results of mutational analysis.

Cellular Extracts, Western Blotting, and Co-Immunoprecipitation

The nuclear and cytoplasmic extracts were prepared according to the method of Schreiber et al. (1989). For co-immunoprecipitation experiments, the cells were lysed in 1 ml of ice-cold lysis buffer (1% NP-40, 150 mM NaCl, 25 mM Tris, pH 7.5, 1 mM EDTA, 1 mM $Na_3VO_4$ 1 μg/ml leupeptine, 1 μg/ml aprotinin and 1 mM PMSF). After 20 minutes of ice incubation, lysed products were centrifuged at 14,000><g for 10 minutes 4° C. and incubated with 4 μg of an unspecific control IgG or specific polyclonal rabbit anti-NPM, named Sil-C, or monoclonal mouse anti-NPM (Clone 376) antibody, respectively, and 30 ul of the Protein A/G Plus-agarose beads (Saint Cruz Biotechnology, Inc.) in incubation overnight at 4° C. The beads then were washed at least thrice with the washing buffer (0.1% NP-40, 150 mM NaCl, 25 mM Tris pH 7.5, 1 mM EDTA and inhibitors). The proteins were separated on a SDS-polyacrylamide gel (SDS-PAGE) and transferred on a PVDF membrane (Millipore), where were incubated with primary antibodies, namely rabbit polyclonal anti-Crml (Saint Cruz Biotechnology, Inc.) or mouse monoclonal anti-Crm1 (BD Transduction Laboratories); respectively; after incubation with a HRP-conjugated secondary antibody, peptides recognized in Western blot were detected using ECL method according to manufacturer instructions (Amersham Bioscience).

Results

The analysis of 40 mutations of NPM gene till now identified in thousand leukaemic patients (FIG. 6), shows that, despite their genetic heterogeneity, all mutations determine some common alterations at level of the carboxyl-terminal portion of the corresponding mutated NPM proteins.

The FIG. 6 shows the changes in the tryptophans 288 and 290 and the creation of a NES motif in 40 mutant NPM proteins identified in leukaemic patients; the mutation frequency (%) is present only for 393 AML cases here studied for which were available, in addition to the molecular data, also the results of the immunohistochemical (1H) staining. Alterations are of two types: i) the mutation of both the tryptophans 288 and 290 (or only 290) and ii) the creation a new motif named NES ("Nuclear Export Signal motif). NES is a protein structure that is specifically recognized by Crm1 (or Exportin 1), the protein physiologically delegated to the transport of other proteins from nucleus to cytoplasm. From a molecular standpoint, NES motif is defined as a sequence of about 10 amino acids of type YxxxYxxYxY (SEQ ID No 56) where Y indicates a hydrophobic amino acid of leucine, isoleucine, methionine, valine or phenylalanine type and x is equivalent to others amino acids. In the NES, the hydrophobic amino acids Y are spaced by precise intervals (varying from 1 to three spaces), where the spacing is represented by other amino acids that, in the scheme, are indicated with the x letter.

The NES type can vary from each other NPM mutant. The type and the frequency of NES in the various leukaemic NPM mutants are illustrated in FIG. 6. The more frequent NES motif, found in about 65% of mutants, is denominated Lxxx-VxxVxL (where L=leueine, V=valine and x is equivalent to other amino acids) (SEQ ID No 1). The remaining 35% of NPM mutant proteins contains rarer NES variants, in which the valine in second position of NES is replaced with another hydrophobic amino acid. Examples of this type, illustrated in FIG. 6, are NESs of type LxxxLxxVxL(SEQ ID No 2), LxxxFxxVxL(SEQ ID No 3), LxxxMxxVxL(SEQ ID No 4), LxxxCxxVxL(SEQ ID No 5) (where L=Leucine; V=Valine; F=Phenylalanine; M=Methionine; C=Cysteine; and x is equivalent to another amino acid).

Relationship Between NES Type and Mutations of Tryptophans in Position 288 and 290

From FIG. 6 can be deduced that tryptophan in position 290 is mutated in all 40 leukaemic NPM mutants. On the contrary, 13 of the 40 mutants (32.5%) preserve tryptophan in position 288. A careful analysis of protein structures of the 40 mutants clearly indicates that a relationship exists between NES type and mutations at level of tryptophans 288 and 290 (FIG. 6 and Table 3). Particularly it is shown as the more frequent NES motif, (namely LxxxVxxVxL (SEQ ID No 1) type) is always associated to mutations of both tryptophans 288 and 290, while tryptophan 288 is preserved only in NPM mutant proteins that contain a NES variant of type above-indicted namely those in which valine in second position of NES is replaced with another hydrophobic amino acid (FIG. 6 and Table 3). Table 3 shows the correlation between NES motif and the tryptophans 288 and 290 in 40 NPM mutant proteins of leukaemic patients.

TABLE 3

| NES Variant | Motif | NPM Mutants (n=) | Mut W (288) | Mut W (290) |
|---|---|---|---|---|
| 1 | L-XXX-V-XX-V-X-L | 26/40 | 26/26 | 6/26 |
| 2 | L-XXX-L-XX-V-X-L | 6/40 | 1/6* | 6/6 |
| 3 | L-XXX-F-XX-V-X-L | 3/40 | 0/3 | 3/3 |
| 4 | L-XXX-M-XX-V-X-L | 2/40 | 0/2 | 2/2 |
| 5 | L-XXX-C-XX-V-X-L | 2/40 | 0/2 | 2/2 |
| 6 | L-XXX-F-XXX-L-FKKIV | 1/40 | 0/1 | 1/1 |

*The mutation Q of FIG. 6 causes a mutation of both two tryptophans 288 and 290 in presence of the variant 2 of NES (L-xxx-L-xx-V-x-L); mutW: mutated tryptophan.

The most common NES motif is the variant 1; the other NES variants (type 2-6) are less frequent and they differentiate from the variant 1 for the presence, in the place of Valine (V) in NES second position, of a Leucine (L), Phenylalanine (F), Methionine (M), or Cysteine (C).

Cytoplasmic Expression of NPM Mutants is a NES-Dependent Event

The fact that all NPM mutants contain a new NES motif in their carboxyl-terminal portion suggests that the cytoplasmic removal of NPM can result from an active transport of NPM mutants by means of Crm1, the receptor delegated to the protein transport from nucleus to cytoplasm.

The authors have carried out some experiments to verify whether the nucleus-cytoplasm transport of NPM leukaemic mutants is altered somehow, in the presence of substances that, as already known, inhibit the activity of the Crm1/Esportin 1, as well as Leptomicin B or the Ratjadons.

The results of the experiments are clear. FIG. 7 shows as the nuclear export of NPM mutants is NES-dependent. Under basal conditions, HI299 or NIH3T3 cells transfected with cDNAs that encode for labelled NPM mutant proteins show the expected aberrant cytoplasmic localization of mutants. In contrast, in the presence of Leptomicin B (LMB), NPM mutant proteins are re-localized from the cytoplasmic to the nuclear compartment (nucleoplasm) (panels 7A and 7B). FIGS. 7C-E shows the analysis at different time points of the LMB effects on the mutant A associated to eGFP (eGFP—NPMmutA) in NIH-3T3 cells: the addition of LMB results in a reduction of fluorescence in cytoplasm and Golgi area and concomitant fluorescence increase in nucleoplasm.

About 50% of mutant type A (the more common one) is re-localized in nucleus in 20 minutes and the whole process is completed in 1 hour (panels C-D).

The Western-blot analysis of the sub-cellular distribution of Type A NPM mutant bound to GFP in Leptomicin B treated NIH-3T3 cells confirmed that, over time, the GFP-NPM protein mutant A (molecular weight 64 kDa), unlike the GFP protein (molecular weight 27 kDa), progressively accumulates in the pellet containing nucleuses (FIG. 7E). On the contrary, in untreated NIH-3T3 cells, both GFP-NPM and GFP proteins are, as expected, only in the cytoplasmic fraction. In fact, the LMB treatment induces a time-dependent accumulation of eGFP-NPMmutA in the pellet fractions (P). The purity of the sub-cellular fractions was measured by removal of the antibody and blotting with an anti-β-tubulin antibody (inferior panel FIG. 7E). A not significant contamination was measured for the over-expressed proteins (as it is clear in GFP blotting) (middle panel). In untreated cells, eGFP—NPMmutA was found only in the cytoplasmic fractions (C). The experiment was carried out in the absence of dicycloeximide so that the continuous presence of GFP—NPMmA in the cytoplasmic fractions during the treatment with LMB has been shown over time.

Figure 8A:
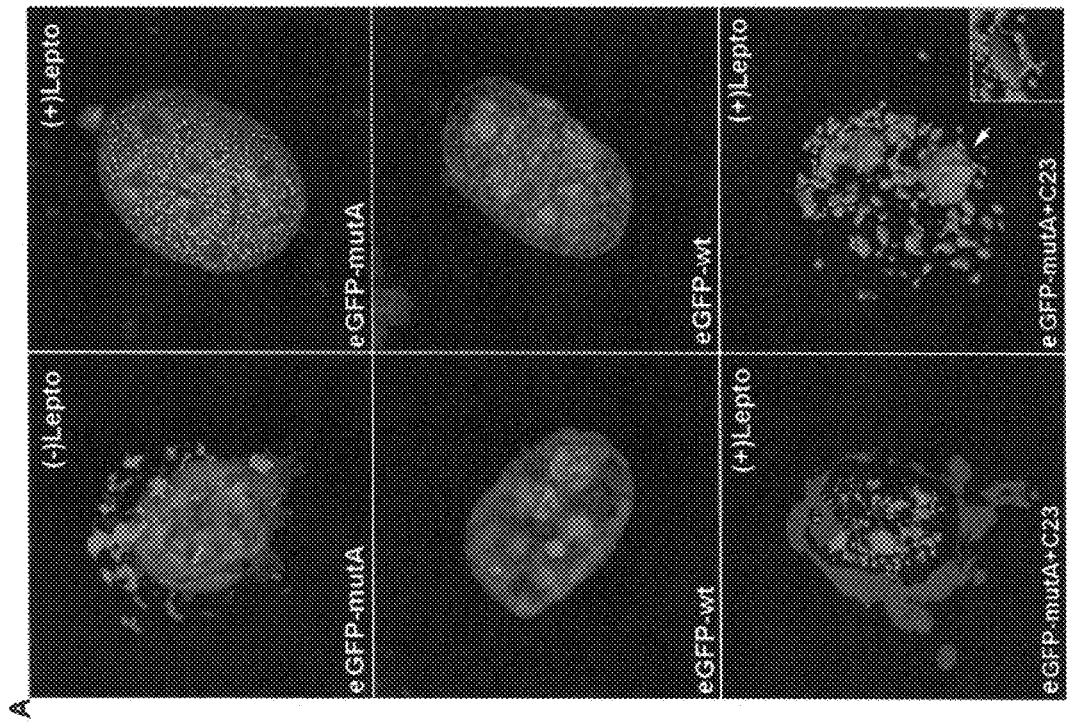

The confocal microscope analysis of cells transfected with various constructs of NPM-EFG clearly shows that NPM mutants, after Leptomicin B treatment, are re-localized in the nucleus and, specifically, in nucleoplasm (FIG. 8A, on top), rather than in the nucleolus, that is the place in which physiologically the wild-type NPM protein localizes (FIG. 8A, middle). The nucleoplasmic re-localization of mutants by Leptomicin B is also shown through double staining at confocal microscope that underlines the presence of a mutual exclusiveness between the localization places of NPM mutant, displaced in nucleoplasm, and nucleolin (C23) that, as expected, is selectively expressed at nucleolar level (FIG. 8A, in bottom).

Figure 8B:
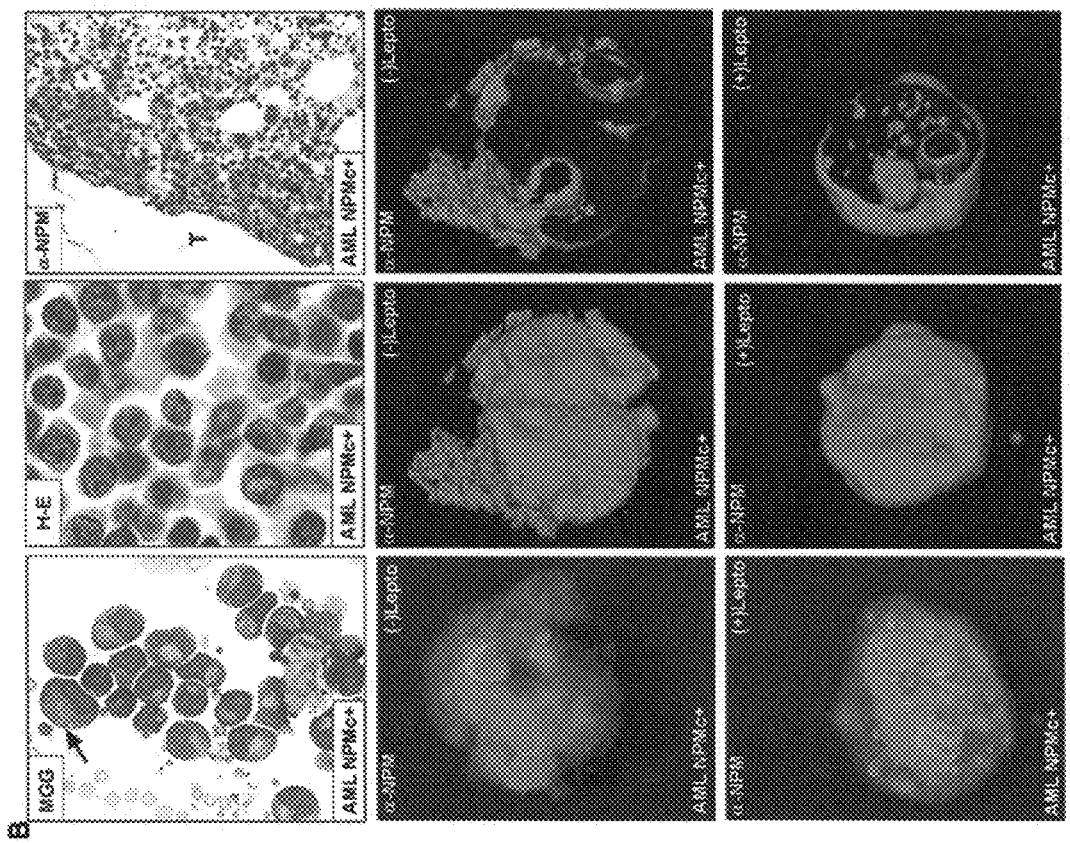

The nucleoplasmic re-localization of NPM after treatment with Crm1 inhibitors was also confirmed on cells of patients with NPMc+ AML (FIG. 8B).

An identical effect of the Crm1 inhibitors on the mutant was also observed in OCI-AML3 human myeloid line that includes type A NPM mutation (FIG. 9A). In these cells, by co-precipitation experiments a direct physical interaction between mutated NPM protein and Crm1 was also shown (FIG. 9B).

The fundamental role played by NES motif in the process of expulsion from nucleus of NPM mutants and their consequent accumulation in cytoplasm, is shown also by site-directed mutagenesis experiments. In fact, the substitution in type A NPM mutant of two valines of NES for two glycines (NPM mutA no-NES), vanishes the ability of mutant to be exported from nucleus to cytoplasm (FIG. 10).

Cytoplasmic Accumulation of Mutants Depends on the Coordinated Action of NES and Mutations of Tryptophans 288 and 290

The role of two tryptophans 288 and 290 in NPM cytoplasmic accumulation was evaluated using natural NPM mutants (from leukaemic patients) and NPM mutants constructed by site-directed mutagenesis. To assess the effect on nucleolar bond of a single mutation at level of tryptophan 290, we used the natural leukaemic mutant type E that, as illustrated in FIG. 6, maintains tryptophan 288. Following treatment with Leptomicin B, type E NPM mutant is re-localized at nuclear level. However, unlike that observed with mutant A, the re-localization occurs not only at nucleoplasma but also at nucleolus level (FIG. 10). A nuclear compartment distribution very similar to that of mutant E, is also observed with an artificial construct of type A NPM mutant in which the mutated tryptophan in position 290 was re-inserted by site-directed mutagenesis (A290W). When both two tryptophans 288 and 290 are re-inserted in mutant A (C288W+A290W), the mutant protein, despite the presence of NES, locates completely in nucleoli, independently from the presence of Leptomicin B. The results of these experiments are illustrated in FIG. 10.

These observations clearly show that the tryptophans 288 and 290 contribute significantly to NES-mediated nuclear expulsion of NPM mutants. In conclusion, in order that the aberrant cytoplasmic accumulation of NPM occurs, it is necessary that NES and the mutations of two tryptophans (or only tryptophan 290) act in combination. In other words, it is impossible to have cytoplasmic accumulation of NPM mutants when only NES is present in the absence of mutations of two tryptophans 288 and 290 (or only tryptophan 290), or vice versa.

NPM Mutants Dislocate the NPM Wild-Type Protein from its Physiological Place (Nucleolus) to the Cytoplasm Because all leukaemic NPM mutated proteins preserve the dimerization domain in the N-terminal site, it can be hypothesized that they can form heterodimers with NPM wild-type protein, like among the fusion proteins (NPM-ALK and NPM-MLF1) and same NPM wild-type protein.

FIG. 11A shows that, by heterodimerization mechanism, the mutants are able to bind and dislocate the NPM wild-type protein in cytoplasm. In fact, by co-transfecting H1299 cells with vectors encoding for (wild-type)-HA NPM and (mutant A)-eGFP NPM, it is observed that the mutant and the wild-type NPM protein co-locate in cytoplasm. About 30% of cells were transfected and for about 70% of these, NPM mutant causes a partial recruitment of the wild-type form of NPM from the nucleoli to nucleoplasm and cytoplasm. These results are also confirmed by co-precipitation experiments of wild-type NPM (HA labelled) and mutant NPM (Flag labelled) (FIG. 11B). To transfect H1299 cells, plasmids encoding for FH-PMwt and FH-NPM mutant A were used. In the left panel of FIG. 11B, 5% of whole lysed cells derived from stably transfected cells with FH-NPMwt, FH-NPM mutant A or 111299 control cells was subjected to Western blot with α-NPM or α-HA. In the right panel, the 95% remaining of lysed cells was immuno-precipitated with an anti-Flag antibody (M2), and used for Western blot with α-NPM or it α-HA.

The possible mechanism of the altered nucleus-cytoplasm restricted transport of mutants and wild-type NPMs is schematised in FIG. 11C.

Immunohistochemistry to Predict all Mutations at Level of Exon 12 of NPM Gene

As above illustrated, the mechanism responsible of the accumulation of NPM mutant proteins in the cytoplasm of leukaemic cells, depend on the mutations of tryptophans 288 and 290 and creation of NES. Because these alterations are present in all till now identified leukaemic NPM mutants, it is hypothesized that the immunohistochemical staining with anti-NPM antibodies is able to predict, by demonstrating cytoplasmic delocalization of NPM, all mutations occurring at level of exon 12 of NPM gene.

To verify this hypothesis, we have compared the sub-cellular expression of NPM protein (nuclear vs cytoplasmic) with the mutational state of NPM gene. The study was carried out on 393 patients with AML of GIMEMA AML99P/AML 12 EORTCs protocol. Obtained results clearly show that the presence of a cytoplasmic positivity for NPM is predictive with absolute specificity of mutations at level of exon 12 of NPM (Table 4).

TABLE 4

| LAM (N = 373) | NPM protein localization* | NPM gene mutations (Exon-12) |
|---|---|---|
| 191 | Cytoplasmic | 191/191 |
| 202 | Nuclear | 0/202 |

*Determined on paraffin embedded sections with monoclonal anti-NPM antibodies

Immunohistochemical test can be used for diagnostic purpose as indicated in FIG. 12. The test is rapid, economic, easily interpretable, highly sensitive and specific. For all these reasons it could be used as first step in the molecular characterization of AMLs. In fact in NPMc+ AMLs it isn't necessary to carry out cytogenetic, FISH and molecular analysis, for the major chromosomal alterations, such as t(15; 17), t(8;21), inv16, t(6;9) and 11q23/MLL because they are mutually exclusive with the cytoplasmic positivity for NPM. On the contrary, in NPMc AMLs, these analyses are compulsory. Cytogenetics helps for the identification of rare translocations with potential prognostic impact in 14% of NPMc+ AML with minor chromosomal anomalies. Mutations of FLT3 gene should be searched in all AML patients AML (independently on NPM) because its correlation with the sub-cellular expression of NPM can help to identify new prognostic subgroups in normal karyotype AML (Schnittger et al., 2005; Dohner et al., 2005; Verhaak et al., 2005). The use of immunohistochemistry to identify NPM mutations has also a clinical importance, because the cytoplasmic distribution of NPM and gene mutations are predictive of a good response to induction therapy, and a better long-term prognosis compared with cases of acute leukaemia with normal karyotype without mutation of NPM gene (NPMc-AML) (Schnittger et al., 2005; Dohner et al, 2005; Verhaak et al., 2005).

The above illustrated data explain mechanism through which the exon 12 specific mutations of NPM gene alter the nucleus-cytoplasm transport of mutated and wild-type NPM proteins. The mechanism is identical both in transfected and leukaemic cells of patients with NPMc+ AML and in OCI/AML3 human leukaemic line. Particularly, the mutations lead to two fundamental changes in the carboxyl-terminated region of NPM mutants: 1) a NES is produced that potentiates the expulsion of mutant proteins by Crm1; and 2) two tryptophans 288 and 290 (or only tryptophan 290) are lost which, under normal conditions, are essential for the bond of NPM protein to nucleoli.

The primary sequence analysis of wild-type NPM protein allowed to detect an hypothetical physiological NES of Lxx-PxxLxL (SEQ ID No 81) type, which is localized in the zone between residues 94 and 102 of NPM (Wang et al., 2005). Despite the presence of this NES, the wild-type NPM protein, under physiological conditions, locates mainly in nucleoli and this suggests that the part of NPM protein that is normally expelled from nucleus to cytoplasm through physiological NES, is decidedly inferior to that of the same protein that, by two NLSs ("nuclear localization signals"), is able to go back from cytoplasm into nucleus. Because the murine and human artificial wild-type NPM mutants without the two tryptophans 288 and 290 (different with respect to the leukaemic Type A NPM mutant only for the lack of C-terminal NES) locate exclusively in nucleoplasm (Nishimura et al., 2002), it is very likely that the additional NES, created by the mutation at level of C-terminal region, confers to leukaemic NPM mutant a greater ability to be exported out of nucleus; this could be due to the additive effect and/or increased Crm1 affinity of the second NES.

Although both, 288 and 290, play a role in the nucleolar localization of NPM, tryptophan 290 could be more important, because it is constantly altered in all till now identified leukaemic NPM mutants. The mutation of both two tryptophans allows the maximum inhibition of the nucleolar bond and nucleoplasmic delocalization of mutants to be achieved in leukaemic NPMc+. cell Of great importance is the observation that NES motif more commonly found in NPM mutants (LxxxVxxVxL) (SEQ ID No 1) is always associated with mutations of both tryptophans. In contrast, tryptophan 288 appears to be maintained only in those NPM mutants including less common variants of NES, namely those characterized by the presence of leucine phenylalanine, cysteine or methionine in the second position of NES, in place of valine (Table 3). These two observations indicate a likely functional difference among NESs of the C-terminal region of leukaemic NPM mutants.

The results of our studies show also unequivocally that the aberrant cytoplasmic accumulation of mutants can occur only due to the coordinated action of NES and mutated tryptophans. It is possible that the anomalous accumulation of NPM mutants occurs according to the following mechanism: i) mutated leukaemic NPM proteins preserving two nuclear localization signals (NLS), enter into nucleus; ii) their ability to bind the nucleoli is completely inhibited when the tryptophans are mutated, or partially inhibited when only tryptophan 290 is altered, resulting in the accumulation of mutants in nucleoplasm; iii) nucleoplasmic mutants are caught by Crml that determines rapid expulsion thereof in cytoplasm where they progressively accumulate.

The explanation of the altered transport mechanism of NPM in NPMc+ leukaemia suggests, as possible therapeutic intervention area, the "re-localization" of leukaemic NPM mutants and wild-type NPM protein in their physiological sites, through the use of Crml inhibitors or small synthesis molecules that interfere with the NPM mutant-Crml bond or wild-type NPM protein or other molecules able to interact with NPM (ARF, etc.).

EXAMPLE 5

Development of a Quantitative POR System for Evaluation and Monitoring of Minimal Residual Disease Several heterozygote NPM1 mutations suggest the necessity of a mutation-specific system for disease monitoring. In the development of system it is worth considering that the two most frequent mutations, so-called mutation A and B, include over 95% of all mutated cases.

Materials and Methods

A specific evaluation method uses a forward primer designed on exon 11 (cNPM1-F: 5'-5'-GAAGAATTGCTTC-CGGATGACT-3'(SEQ ID No 52)), a probe on the junction exon 11/exon 12 (c.Probe: 5'-FAM-ACCAAGAGGCTAT-TCAA-MGB-3' (SEQ ID No 55)) and mutation-specific reverse primers (cNPM mut.A-R: 5'-CTTCCTCCACTGC-CAGACAGA-3' (SEQ ID No 53) and cNPM mut.B-R: 5'-TTCCTCCACTGCCATGCAG-3' (SEQ ID No 54)). Forward primer and probe are the same regardless of different mutations (FIG. 13).

Step 1=Retro-transcription reaction according to EAC protocol (Gabert et al., Leukaemia 2003).

Step 2=Amplification reaction uses a mixture containing 12.5 µl of Taq Man universal PCR Master Mix (Applied Biosystem), 300 nM Primers, 200 nM of probe and 5 µl of cDNA in a total volume of 25 µl. Conditions: 2 minutes at 50° C. (UNG enzyme activation), 10 min at 95° C. (UNG enzyme inactivation and AmpliTaq polymerase activation) followed by 50 cycles at 95° C. for 15 seconds, at 62° C. for 1 minute for mutation A and at 59° C. for 1 minute for mutation B. As quantitative and qualitative RNA control ABL gene can be amplified. The analysis setting of instrument (ABI PRISM 7700 Sequence Detection System, Applied Biosystem) includes a "threshold" of 0.1 with "a baseline" from 3 to 15 both for ABL and NPM. System sensitivity and specificity are analyzed using sequential dilutions, by a factor equal to 10, by mixing RNA extracted from medullary leukaemic cells with NPM mutation type A or B and RNA obtained from a pool of medullary cells from patients without NPM mutations (verified by sequencing).

The standard plot of absolute quantitative evaluation for mutation A is constructed using a plasmid construct. Such a construct consists of plasmid vector pCRII-TOPO, (Invitrogen, Groningen, Netherlands) plus a portion of NPM1 gene containing mutation A. The amplification of mutation A is obtained by RT-PCR with the primers NPM1__390_F (5'-GGTCTTAAGGTTGAAGTGTGGT-3' (SEQ ID No 38)) and NPM1__1043_R (5'-TCAACTGTTACAGAAAT-GAAATAAGACG-3' (SEQ ID No 39)).

The plasmid is prepared in five sequential dilutions: $10^5$, $10^4$, $10^3$, $10^2$, 10 copies. The results of RQ-PCR for mutation A normalized on ABL transcripts are expressed as copy number of NPM with mutation A every $10^4$ copies of ABL.

The "maximum reproducible sensitivity", according to guidelines about Minimal Residual Disease defined by an European Study Group (van der Velden V H J et al, 2003), is defined as the lowest dilution in which all sample' replicates are positive within a Ct (Cycle threshold) of 1.5, and the highest Ct of replicates is at least of 3.0 Ct lower than the lowest value of background. The "maximum sensitivity" is defined as minimum dilution in which at least a sample is positive and at least 1.0 Ct lower than the smallest Ct of background. With these definitions, a result is defined as "positive, not quantifiable" in the presence of amplified in 1 of 2 replicates below the maximum reproducible sensitivity, but still 1.0 Ct lower than the lowest background.

Results

The sensitivity and specificity of "Reverse Quantitative" PCR(RQ-PCR) were tested in the dilution series of $10^5$, $10^4$, $10^3$, $10^2$, 10 plasmid copies. The Ct values (Cycle Threshold) and the "slope" of plot for plasmid are shown in the following figure.

The standard plasmid plots show a "mean slope" of −0.38 and an "intercept" of 39.5±0.45 Ct. The correlation coefficient is high (>0.99 in all experiments) and demonstrates the accurate identification of the presence of copies of mutation A in unknown samples. The maximum reproducible sensitivity of RQ-PCR corresponds to 10 plasmid molecules (FIG. 14).

Sequential dilutions based on a factor equal to 10 were carried out to simulate the sensitivity and reproducibility of RQ-PCR in monitoring of minimal residual disease in 5 patient diagnosed as afflicted with (acute myeloblastic leukaemia) NPMc+AML (4 patients with mutation A and 1 with mutation B).

RNA extracted from medullary leukaemic cells with type A or B NPM mutation was diluted with RNA achieved from a pool of medullary cells from patients without NPM mutations.

Maximum reproducible sensitivity equal to $10^{-4}$ was found in all 5 patients with mutations A or B, while the maximum sensitivity was $10^{-6}$ in the sample with type B mutation and in 3 of 4 samples with type A mutation. The maximum sensitivity equal to $10^{-5}$ was observed in one of samples with A mutation. The background amplification was observed only in one case and at very high Ct values (Ct>48), showing the high specificity of system (FIG. 15).

Using the plasmidic calibration plot 13 patients afflicted with AML with NPM mutation type A were analyzed at diagnosis and after induction treatment.

The results were expressed as "copy number of NPM1 Mut.A/10000 copies of ABL." At diagnosis, all samples show>30000 copies. After induction treatment the copy number diminishes markedly in 10 patients that evidenced complete haematological remission. In 5 patients the reached copy number was <70 while in the other 5 patients it ranged between 580 and 5046. A small or no diminution of the copy number was evidenced in 3 cases: 2 complete remissions and 1 partial remission (FIG. 16).

In 3 patient afflicted with AML with mutations of type A NPM1 gene the aforesaid system was used for monitoring the minimal residual disease both during the therapy and in the follow-up.

The cDNA specific RQ-PCR showed a copy number<10 after the first or the second cycle of consolidation therapy. A different kinetics in the diminution of the copy number was observed in the three samples as shown in FIG. 17. A small but persistent number of mutated copies is associated with the haematological remission in a patient (square). In one of the remaining cases the number of mutated copies markedly decreases after consolidation treatment (diamonds); such diminution is less pronounced in the second patient (triangles). In the last two patients the copy number again increases and in both cases haematological relapse occurs (FIG. 17).

In conclusion the system has such sensitivity, specificity and reproducibility characteristics to be used in clinical tests.

BIBLIOGRAPHY

Grimwade D, Walker H, Oliver F, et al. Blood 1998; 92:2322-33.
Schnittger S, Schoch C, Dugas M, et al. Blood 2002; 100:59-66.
Byrd J C, Mrozek K, Dodge R K, et al. Blood 2002; 100: 4325-36.
Bullinger L, Dohner K, Bair E, et al. N Engl J Med 2004; 350:1605-16.
Valk P J, Verhaak R G, Beijen M A, et al. N Engl J Med 2004; 350:1617-28.
Frohling S, Schlenk R F, Breitruck J, et al. Blood 2002; 100:4372-80.
Pabst T, Mueller B U, Zhang P, et al. Nat Genet. 2001; 27:263-70.
Steudel C, Wermke M, Schaich M, et al. Genes Chromosomes Cancer 2003; 37:237-51.
Carnicer M J, Nomdedeu J F, Lasa A, et al. Leuk Res 2004; 28:19-23.
Christiansen D H, Pedersen-Bjergaard J. Leukaemia 2001; 15:1848-51.
Falini B., et al. N Engl J Med 2005; 352:254-66.
Cordell J L, Pulford K A, Bigerna B, et al. Blood 1999; 93:632-42.
Borer R A, Lehner C F, Eppenberger H M, Nigg E A. Cell 1989; 56:379-90.
Dumbar T S, Gentry G A, Olson M 0. Biochemistry 1989; 28:9495-501.
Okuda M, Horn H F, Tarapore P, et al. Cell 2000; 103:127-40.
Gabert J, Beillard E, van der Velden V H J, et al. Leukaemia 2003; 17:2318-2357.
Bertwistle D, Sugimoto M, Sherr C J. Mal Cell Biol 2004; 24:985-96.
Colombo E, Marine J C, Danovi D, Falini B, Pelicci P G. Nat Cell Biol 2002; 4:529-33.
Kurki S, Peltonen K, Latonen L, et al. Cancer Cell 2004; 5:465-75.
Grisendi S., et al. Nature 2005; 437:147-53.
Morris S W, Kirstein M N, Valentine M B, et al., Science 1994; 263:1281-4.
Redner R L, Rush E A, Faas S, Rudert W A, Corey S J. Blood 1996; 87:882-6.
Yoneda-Kato N, Look A T, Kirstein M N, et al. Oncogene 1996; 12:265-75.
Falini B, Pileri 5, Zinzani P L, et al., Blood 1999; 93:2697-706.
Falini B, Mason D Y. Blood 2002; 99:409-26.
Bischof D, Pulford K, Mason D Y, Morris S W. Mol Cell Biol 1997; 17:2312-25.
Falini B, Pulford K, Pucciarini A, et al. Blood 1999; 94:3509-15.
Schnittger S, et al. Blood (online Aug. 2, 2005).
Jaffe E, Harris N, Stein H, et al. Lyon: IARC Press; 2001.
Downward J. BMJ 2004; 328:1245-48.
Stocks M R. Drug Discov Today 2004; 9:960-66.
Shuker S B, et al. Science 1996; 274 :1531-34.
Dohner K, et al. Blood (online Jul. 28, 2005).
Verhaak R G, et al. Blood (online Aug. 18, 2005).
Cordell J L, Falini B, Erber W N, et al. J Histochem Cytochem 1984; 32:219-29.
Mitelman F. Base1: Karger; 1995.
Crescenzi B, Fizzotti M, Piattoni 5, et al. Cancer Genet Cytogenet 2000; 120:25-9.
Van Dongen J J, Macintyre E A, Gabert J A, et al. Leukaemia 1999; 13:1901-28.
Soekarman D, von Lindern M, Daenen S, et al. Blood 1992; 79:2990-7.
Van der Velden V H J, Hochhaus A, Cazzaniga G, et al Leukaemia 2003; 17:1013-1034.
Noguera N I, Breccia M, Divona M, et al. Leukaemia 2002; 16:2185-9.
Cimino G, Rapanotti M C, Elia L, et al. Cancer Res 1995; 55:1625-8.
Goodell M A, Rosenzweig M, Kim H, et al. Nat Med 1997; 3:1337-45.
Engelhardt M, Lubbert M, Guo Y. Leukaemia 2002; 16:1603-8.
Nishimura Y, Okhubo T., Furuichi Y, Umekawa H. Biosci Biotechnol Biochem 2002; 66:2239-42.
Horn H F, Vousden K H. Nature 2004; 427:110-1.
Hingorani K, Szebeni A, Olson M 0. J Biol Chem 2000; 275:24451-7.
Chang J H, Lin J Y, Wu M H, Yung B Y. Biochem J 1998; 329(Pt 3):539-44.
Goding J. Monoclonal Antibodies. Academic Press 1983.
Quentmeier H., Leukaemia 2005; 19:1760-67.
Schreiber E, et al. Nucleic Acids Res. 1989; 17:6419.
Wang W, et al. Nat Cell Biol 2005; 7:823-30,
Gabert J, et al. Leukaemia 2003; 17:1013-1034.

The invention claimed is:

1. Isolated oligonucleotide sequences encoding human nucleophosmin (NPM) comprising a loss of a tryptophan residue at position 290 and comprising a signal motif of nuclear export (NES) beginning at position 287 of the human nucleophosmin protein,
wherein the NES comprises the amino acid sequence YxxxYxxYxY (SEQ ID No 56) wherein Y is a hydrophobic amino acid selected from the group consisting of leucine, isoleucine, methionine, valine, phenylalanine, and x can be any amino acid, and
wherein said sequences are deoxyribonucleotide or ribonucleotide sequences.

2. Isolated oligonucleotide sequences encoding protein according to claim 1, wherein both tryptophan residues 288 and 290 are deleted.

3. Isolated oligonucleotide sequences encoding the protein according to claim 1, wherein said amino acid sequence YxxxYxxYxY (SEQ ID No 56) is selected from the group consisting of LxxxVxxVxL (SEQ ID No 1), LxxxLxxVxL (SEQ ID No 2), LxxxFxxVxL (SEQ ID No 3), LxxxMxxVxL (SEQ ID No 4), and LxxxCxxVxL (SEQ ID No 5).

4. Isolated oligonucleotide sequences encoding the protein according to claim 3
wherein the amino acid sequence LxxxVxxVxL (SEQ ID No 1) is selected from the group consisting of LCLAVEEVSL (SEQ ID No 6); LCMAVEEVSL (SEQ ID No 7); LCVAVEEVSL (SEQ ID No 8); LSRAVEEVSL (SEQ ID No 9); LCTAVEEVSL (SEQ ID No 10); LSQAVEEVSL (SEQ ID No 11); LCHAVEEVSL (SEQ ID No 12); LCRAVEEVSL (SEQ ID No 13); LCRGVEEVSL (SEQ ID No 14); LCQAVEEVSL (SEQ ID No 15); LCAAVEEVSL (SEQ ID No 16); LCKAVEEVSL (SEQ ID No 17);
wherein the amino acid sequence LxxxLxxVxL (SEQ ID No 2) is selected from the group consisting of LWQSLAQVSL (SEQ ID No 18); LWQSLEKVSL (SEQ ID No 19); LWQSLSKVSL (SEQ ID No 20); and LCTFLEEVSL (SEQ ID No 21);
wherein the amino acid sequence LxxxFxxVxL (SEQ ID No 3) is selected from the group consisting of LWQCFAQVSL (SEQ ID No 22); LWQCFSKVSL (SEQ ID No 23); LWQRFQEVSL (SEQ ID No 24); and LWQDFLNRL (SEQ ID No 25);
wherein the amino acid sequence LxxxMxxVxL (SEQ ID No 4) is selected from the group consisting of LWQSMEEVSL (SEQ ID No 26); and LWQRMEEVSL (SEQ ID No 27); or
wherein the amino acid sequence LxxxCxxVxL (SEQ ID No 5) is LWQCCSQVSL (SEQ ID No 28).

5. Isolated oligonucleotide sequences encoding the protein according to claim 1 wherein said human nucleophosmin protein comprises a VSLRK peptide (SEQ ID No 29) in the C-terminal region.

6. Isolated oligonucleotide sequences encoding the protein according to claim 5 further comprising a D-amino acid upstream of the N-terminal end of the amino acid sequence YxxxYxxYxY (SEQ ID No 56).

7. Isolated oligonucleotide sequences encoding the protein according to claim 1, wherein said protein is fused to a reporter protein wherein said reporter protein is selected from the group consisting of EGFP, beta-galactosidase, luciferase, and GFP.

8. Isolated oligonucleotide sequences according to claim 1, wherein said deoxyribonucleotide sequences include at least one of the sequences selected from the group consisting of SEQ ID NOs: 57 and 60-64 in the C-terminal region of the sequence of the human nucleophosmin.

9. Isolated oligonucleotide sequences according to claim 1, wherein said sequences are labeled with an agent selected from the group consisting of fluorescent substance, biotin, radioisotope, and nanoparticle.

10. An isolated expression vector comprising the oligonucleotide sequences as defined in claim 1.

11. An isolated host cell permissive for at least one of the proteins as defined in claim 1.

12. A method of diagnosing acute myeloid leukemia (AML) or monitoring residual AML disease, the method comprising
detecting, in a biological sample from a subject, the presence of an oligonucleotide sequence according to any one of claims 1, 2 and 3-7, and
diagnosing the subject as having AML or residual AML disease when the oligonucleotide sequence is present in the sample,
wherein said detecting comprises nucleic acid amplification with a primer pair selected from:

```
i)      NPM1_25F:
                                              (SEQ ID No 36)
        5'-GGTTGTTCTCTGGAGCAGCGTTC-3';

NPM1_111 2R:
                                              (SEQ ID No 37)
        5'-CCTGGACAACATTTATCAAACACGGTA-3';

ii)     NPM1_390F:
                                              (SEQ ID No 38)
        5'-GGTCTTAAGGTTGAAGTGTGGT-3';

NPM1_1043_R;
                                              (SEQ ID No 39)
        5'-TCAACTGTTACAGAAATGAAATAAGACG-3';

iii)    NPM_940F_mutA
                                              (SEQ ID No 40)
        5'-GAGGCTATTCAAGATCTCTGTCT-3';

NPM1_1112 R
                                              (SEQ ID No 41)
        5'-CCTGGACAACATTTATCAAAGACGGTA-3';

iv)     NPM_940F_mutB
                                              (SEQ ID No 42)
        5'-GAGGCTATTCAAGATCTCTGCAT 3';

NPM1_1112 R
                                              (SEQ ID No 43)
        5'-CCTGGACAACATTTATCAAACACGGTA3';

v)      NPM_940F_mutC
                                              (SEQ ID No 44)
        5'-GAGGCTATTCAAGATCTCTGCGT-3';

NPM1_1112 R
```

-continued (SEQ ID No 45)
5'-CCTGGACAACATTTATCAAACACGGTA-3';

vi) NPM_940F_mutD
(SEQ ID No 46)
5'-GAGGCTATTCMGATCTCTGCCT-3';

NPM1_1112 R
(SEQ ID No 47)
5'-CGTGGACAACATTTATCAAACACGGTA-3';

vii) NPM1 -F:
(SEQ ID No 48)
5'-TTAACTCTCTGGTGGTAGAATGAA-3';

NPM1-R:
(SEQ ID No 49)
5'-CCAGACTATTTGCCATTCCTAAC-3';

viii) NPM1_89F_BamHI:
(SEQ ID No 50)
5'-GCCACGGATCCGAAGATTCGATGGAC-3';

NPM1_1044R_EcoRI:
(SEQ ID No 51)
5'ATCAAGAATTCCAGAAATGAAATAAGA CG-3';

ix) cNPM-F:
(SEQ ID No 52)
5'-GAAGAATTGCTTCCGGATGACT-3'
and cNPM mut.A-R:
(SEQ ID No 53)
5'-CTTCCTCCACTGCCAGACAGA-3'
or cNPM mut.B-R:
(SEQ ID No 54)
5'-TTCCTCCACTGCCATGCAG-3'.

13. The method of claim 12, wherein a primer of the primer pair is labeled with an agent selected from the group consisting of fluorescent substance, biotin, radioisotope, and nanoparticle.

* * * * *

SEQUENCE LISTING

```
<160> NUMBER OF SEQ ID NOS: 142

<210> SEQ ID NO 1
<211> LENGTH: 10
<212> TYPE: PRT
<213> ORGANISM: Artificial
<220> FEATURE:
```

<223> OTHER INFORMATION: NES motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

Leu Xaa Xaa Xaa Val Xaa Xaa Val Xaa Leu
 1               5                  10

<210> SEQ ID NO 2
<211> LENGTH: 10
<212> TYPE: PRT
<213> ORGANISM: Artificial
<220> FEATURE:
<223> OTHER INFORMATION: NES motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Leu Xaa Xaa Xaa Leu Xaa Xaa Val Xaa Leu
 1               5                  10

<210> SEQ ID NO 3
<211> LENGTH: 10
<212> TYPE: PRT
<213> ORGANISM: Artificial
<220> FEATURE:
<223> OTHER INFORMATION: NES motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Leu Xaa Xaa Xaa Phe Xaa Xaa Val Xaa Leu
 1               5                  10

<210> SEQ ID NO 4
<211> LENGTH: 10
<212> TYPE: PRT
<213> ORGANISM: Artificial
<220> FEATURE:
<223> OTHER INFORMATION: NES motif
<220> FEATURE:
<221> NAME/KEY: misc_feature
<222> LOCATION: (2)..(4)
<223> OTHER INFORMATION: Xaa can be any naturally occurring amino acid

```
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 4

Leu Xaa Xaa Xaa Met Xaa Xaa Val Xaa Leu
1               5                   10

<210> SEQ ID NO 5
<211> LENGTH: 10
<212> TYPE: PRT
<213> ORGANISM: Artificial
<220> FEATURE:
<223> OTHER INFORMATION: NES motif
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Leu Xaa Xaa Xaa Cys Xaa Xaa Val Xaa Leu
1               5                   10

<210> SEQ ID NO 6
<211> LENGTH: 10
<212> TYPE: PRT
<213> ORGANISM: Artificial
<220> FEATURE:
<223> OTHER INFORMATION: NES motif

<400> SEQUENCE: 6

Leu Cys Leu Ala Val Glu Glu Val Ser Leu
1               5                   10

<210> SEQ ID NO 7
<211> LENGTH: 10
<212> TYPE: PRT
<213> ORGANISM: Artificial
<220> FEATURE:
<223> OTHER INFORMATION: NES motif

<400> SEQUENCE: 7

Leu Cys Met Ala Val Glu Glu Val Ser Leu
1               5                   10

<210> SEQ ID NO 8
<211> LENGTH: 10
<212> TYPE: PRT
<213> ORGANISM: Artificial
<220> FEATURE:
<223> OTHER INFORMATION: NES motif

<400> SEQUENCE: 8

Leu Cys Val Ala Val Glu Glu Val Ser Leu
1               5                   10

<210> SEQ ID NO 9
```

```
<211> LENGTH: 10
<212> TYPE: PRT
<213> ORGANISM: Artificial
<220> FEATURE:
<223> OTHER INFORMATION: NES motif

<400> SEQUENCE: 9

Leu Ser Arg Ala Val Glu Glu Val Ser Leu
1               5                   10

<210> SEQ ID NO 10
<211> LENGTH: 10
<212> TYPE: PRT
<213> ORGANISM: Artificial
<220> FEATURE:
<223> OTHER INFORMATION: NES motif

<400> SEQUENCE: 10

Leu Cys Thr Ala Val Glu Glu Val Ser Leu
1               5                   10

<210> SEQ ID NO 11
<211> LENGTH: 10
<212> TYPE: PRT
<213> ORGANISM: Artificial
<220> FEATURE:
<223> OTHER INFORMATION: NES motif

<400> SEQUENCE: 11

Leu Ser Gln Ala Val Glu Glu Val Ser Leu
1               5                   10

<210> SEQ ID NO 12
<211> LENGTH: 10
<212> TYPE: PRT
<213> ORGANISM: Artificial
<220> FEATURE:
<223> OTHER INFORMATION: NES motif

<400> SEQUENCE: 12

Leu Cys His Ala Val Glu Glu Val Ser Leu
1               5                   10

<210> SEQ ID NO 13
<211> LENGTH: 10
<212> TYPE: PRT
<213> ORGANISM: Artificial
<220> FEATURE:
<223> OTHER INFORMATION: NES motif

<400> SEQUENCE: 13

Leu Cys Arg Ala Val Glu Glu Val Ser Leu
1               5                   10

<210> SEQ ID NO 14
<211> LENGTH: 10
<212> TYPE: PRT
<213> ORGANISM: Artificial
<220> FEATURE:
<223> OTHER INFORMATION: NES motif

<400> SEQUENCE: 14

Leu Cys Arg Gly Val Glu Glu Val Ser Leu
1               5                   10

<210> SEQ ID NO 15
<211> LENGTH: 10
<212> TYPE: PRT
```

<213> ORGANISM: Artificial
<220> FEATURE:
<223> OTHER INFORMATION: NES motif

<400> SEQUENCE: 15

Leu Cys Gln Ala Val Glu Glu Val Ser Leu
1               5                   10

<210> SEQ ID NO 16
<211> LENGTH: 10
<212> TYPE: PRT
<213> ORGANISM: Artificial
<220> FEATURE:
<223> OTHER INFORMATION: NES motif

<400> SEQUENCE: 16

Leu Cys Ala Ala Val Glu Glu Val Ser Leu
1               5                   10

<210> SEQ ID NO 17
<211> LENGTH: 10
<212> TYPE: PRT
<213> ORGANISM: Artificial
<220> FEATURE:
<223> OTHER INFORMATION: NES motif

<400> SEQUENCE: 17

Leu Cys Lys Ala Val Glu Glu Val Ser Leu
1               5                   10

<210> SEQ ID NO 18
<211> LENGTH: 10
<212> TYPE: PRT
<213> ORGANISM: Artificial
<220> FEATURE:
<223> OTHER INFORMATION: NES motif

<400> SEQUENCE: 18

Leu Trp Gln Ser Leu Ala Gln Val Ser Leu
1               5                   10

<210> SEQ ID NO 19
<211> LENGTH: 10
<212> TYPE: PRT
<213> ORGANISM: Artificial
<220> FEATURE:
<223> OTHER INFORMATION: NES motif

<400> SEQUENCE: 19

Leu Trp Gln Ser Leu Glu Lys Val Ser Leu
1               5                   10

<210> SEQ ID NO 20
<211> LENGTH: 10
<212> TYPE: PRT
<213> ORGANISM: Artificial
<220> FEATURE:
<223> OTHER INFORMATION: NES motif

<400> SEQUENCE: 20

Leu Trp Gln Ser Leu Ser Lys Val Ser Leu
1               5                   10

<210> SEQ ID NO 21
<211> LENGTH: 10
<212> TYPE: PRT
<213> ORGANISM: Artificial
<220> FEATURE:

<223> OTHER INFORMATION: NES motif

<400> SEQUENCE: 21

Leu Cys Thr Phe Leu Glu Glu Val Ser Leu
1               5                   10

<210> SEQ ID NO 22
<211> LENGTH: 10
<212> TYPE: PRT
<213> ORGANISM: Artificial
<220> FEATURE:
<223> OTHER INFORMATION: NES motif

<400> SEQUENCE: 22

Leu Trp Gln Cys Phe Ala Gln Val Ser Leu
1               5                   10

<210> SEQ ID NO 23
<211> LENGTH: 10
<212> TYPE: PRT
<213> ORGANISM: Artificial
<220> FEATURE:
<223> OTHER INFORMATION: NES motif

<400> SEQUENCE: 23

Leu Trp Gln Cys Phe Ser Lys Val Ser Leu
1               5                   10

<210> SEQ ID NO 24
<211> LENGTH: 10
<212> TYPE: PRT
<213> ORGANISM: Artificial
<220> FEATURE:
<223> OTHER INFORMATION: NES motif

<400> SEQUENCE: 24

Leu Trp Gln Arg Phe Gln Glu Val Ser Leu
1               5                   10

<210> SEQ ID NO 25
<211> LENGTH: 9
<212> TYPE: PRT
<213> ORGANISM: Artificial
<220> FEATURE:
<223> OTHER INFORMATION: NES motif

<400> SEQUENCE: 25

Leu Trp Gln Asp Phe Leu Asn Arg Leu
1               5

<210> SEQ ID NO 26
<211> LENGTH: 10
<212> TYPE: PRT
<213> ORGANISM: Artificial
<220> FEATURE:
<223> OTHER INFORMATION: NES motif

<400> SEQUENCE: 26

Leu Trp Gln Ser Met Glu Glu Val Ser Leu
1               5                   10

<210> SEQ ID NO 27
<211> LENGTH: 10
<212> TYPE: PRT
<213> ORGANISM: Artificial
<220> FEATURE:
<223> OTHER INFORMATION: NES motif

```
<400> SEQUENCE: 27

Leu Trp Gln Arg Met Glu Glu Val Ser Leu
1               5                   10

<210> SEQ ID NO 28
<211> LENGTH: 10
<212> TYPE: PRT
<213> ORGANISM: Artificial
<220> FEATURE:
<223> OTHER INFORMATION: NES motif

<400> SEQUENCE: 28

Leu Trp Gln Cys Cys Ser Gln Val Ser Leu
1               5                   10

<210> SEQ ID NO 29
<211> LENGTH: 5
<212> TYPE: PRT
<213> ORGANISM: Artificial
<220> FEATURE:
<223> OTHER INFORMATION: C-terminal peptide

<400> SEQUENCE: 29

Val Ser Leu Arg Lys
1               5

<210> SEQ ID NO 30
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 30

Asp Leu Cys Leu Ala Val Glu Glu Val Ser Leu Arg Lys
1               5                   10

<210> SEQ ID NO 31
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 31

Asp Leu Cys Met Ala Val Glu Glu Val Ser Leu Arg Lys
1               5                   10

<210> SEQ ID NO 32
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 32

Asp Leu Cys Val Ala Val Glu Glu Val Ser Leu Arg Lys
1               5                   10

<210> SEQ ID NO 33
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 33
```

Asp Leu Cys Leu Ala Val Glu Glu Val Ser Leu Arg Lys
1               5                   10

<210> SEQ ID NO 34
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 34

Asp Leu Trp Gln Ser Leu Ala Gln Val Ser Leu Arg Lys
1               5                   10

<210> SEQ ID NO 35
<211> LENGTH: 13
<212> TYPE: PRT
<213> ORGANISM: Artificial
<220> FEATURE:
<223> OTHER INFORMATION: Mutated C-terminal NPM sequence

<400> SEQUENCE: 35

Asp Leu Trp Gln Ser Leu Glu Lys Val Ser Leu Arg Lys
1               5                   10

<210> SEQ ID NO 36
<211> LENGTH: 23
<212> TYPE: DNA
<213> ORGANISM: Artificial
<220> FEATURE:
<223> OTHER INFORMATION: Primer NPM forward

<400> SEQUENCE: 36
ggttgttctc tggagcagcg ttc                                      23

<210> SEQ ID NO 37
<211> LENGTH: 27
<212> TYPE: DNA
<213> ORGANISM: Artificial
<220> FEATURE:
<223> OTHER INFORMATION: Primer NPM reverse

<400> SEQUENCE: 37
cctggacaac atttatcaaa cacggta                                  27

<210> SEQ ID NO 38
<211> LENGTH: 22
<212> TYPE: DNA
<213> ORGANISM: Artificial
<220> FEATURE:
<223> OTHER INFORMATION: Primer NPM forward

<400> SEQUENCE: 38
ggtcttaagg ttgaagtgtg gt                                       22

<210> SEQ ID NO 39
<211> LENGTH: 28
<212> TYPE: DNA
<213> ORGANISM: Artificial
<220> FEATURE:
<223> OTHER INFORMATION: Primer NPM reverse

<400> SEQUENCE: 39
tcaactgtta cagaaatgaa ataagacg                                 28

<210> SEQ ID NO 40
<211> LENGTH: 23

```
<212> TYPE: DNA
<213> ORGANISM: Artificial
<220> FEATURE:
<223> OTHER INFORMATION: Primer NPM forward mutA

<400> SEQUENCE: 40
gaggctattc aagatctctg tct                                          23

<210> SEQ ID NO 41
<211> LENGTH: 27
<212> TYPE: DNA
<213> ORGANISM: Artificial
<220> FEATURE:
<223> OTHER INFORMATION: Primer NPM reverse mutA

<400> SEQUENCE: 41
cctggacaac atttatcaaa cacggta                                      27

<210> SEQ ID NO 42
<211> LENGTH: 23
<212> TYPE: DNA
<213> ORGANISM: Artificial
<220> FEATURE:
<223> OTHER INFORMATION: Primer NPM forward mut B

<400> SEQUENCE: 42
gaggctattc aagatctctg cat                                          23

<210> SEQ ID NO 43
<211> LENGTH: 27
<212> TYPE: DNA
<213> ORGANISM: Artificial
<220> FEATURE:
<223> OTHER INFORMATION: Primer NPM reverse mut B

<400> SEQUENCE: 43
cctggacaac atttatcaaa cacggta                                      27

<210> SEQ ID NO 44
<211> LENGTH: 21
<212> TYPE: DNA
<213> ORGANISM: Artificial
<220> FEATURE:
<223> OTHER INFORMATION: Primer NPM forward mut C

<400> SEQUENCE: 44
gaggctattc aagatctgcg t                                            21

<210> SEQ ID NO 45
<211> LENGTH: 27
<212> TYPE: DNA
<213> ORGANISM: Artificial
<220> FEATURE:
<223> OTHER INFORMATION: Primer NPM reverse mut C

<400> SEQUENCE: 45
cctggacaac atttatcaaa cacggta                                      27

<210> SEQ ID NO 46
<211> LENGTH: 23
<212> TYPE: DNA
<213> ORGANISM: Artificial
<220> FEATURE:
<223> OTHER INFORMATION: Primer NPM forward mut D

<400> SEQUENCE: 46
gaggctattc aagatctctg cct                                          23
```

-continued

<210> SEQ ID NO 47
<211> LENGTH: 27
<212> TYPE: DNA
<213> ORGANISM: Artificial
<220> FEATURE:
<223> OTHER INFORMATION: Primer NPM reverse mut D

<400> SEQUENCE: 47
cctggacaac atttatcaaa cacggta                                       27

<210> SEQ ID NO 48
<211> LENGTH: 24
<212> TYPE: DNA
<213> ORGANISM: Artificial
<220> FEATURE:
<223> OTHER INFORMATION: Primer NPM1 forward

<400> SEQUENCE: 48
ttaactctct ggtggtagaa tgaa                                          24

<210> SEQ ID NO 49
<211> LENGTH: 23
<212> TYPE: DNA
<213> ORGANISM: Artificial
<220> FEATURE:
<223> OTHER INFORMATION: Primer NPM1 reverse

<400> SEQUENCE: 49
ccagactatt tgccattcct aac                                           23

<210> SEQ ID NO 50
<211> LENGTH: 26
<212> TYPE: DNA
<213> ORGANISM: Artificial
<220> FEATURE:
<223> OTHER INFORMATION: Primer NPM forward

<400> SEQUENCE: 50
gccacggatc cgaagattcg atggac                                        26

<210> SEQ ID NO 51
<211> LENGTH: 29
<212> TYPE: DNA
<213> ORGANISM: Artificial
<220> FEATURE:
<223> OTHER INFORMATION: Primer NPM reverse

<400> SEQUENCE: 51
atcaagaatt ccagaaatga aataagacg                                     29

<210> SEQ ID NO 52
<211> LENGTH: 22
<212> TYPE: DNA
<213> ORGANISM: Artificial
<220> FEATURE:
<223> OTHER INFORMATION: Primer NPM forward

<400> SEQUENCE: 52
gaagaattgc ttccggatga ct                                            22

<210> SEQ ID NO 53
<211> LENGTH: 21
<212> TYPE: DNA
<213> ORGANISM: Artificial
<220> FEATURE:
<223> OTHER INFORMATION: Primer NPM forward mut A -continued

<400> SEQUENCE: 53
cttcctccac tgccagacag a                                              21

<210> SEQ ID NO 54
<211> LENGTH: 19
<212> TYPE: DNA
<213> ORGANISM: Artificial
<220> FEATURE:
<223> OTHER INFORMATION: Primer NPM reverse mut B

<400> SEQUENCE: 54
ttcctccact gccatgcag                                                 19

<210> SEQ ID NO 55
<211> LENGTH: 17
<212> TYPE: DNA
<213> ORGANISM: Artificial
<220> FEATURE:
<223> OTHER INFORMATION: Probe
<220> FEATURE:
<221> NAME/KEY: misc_feature
<222> LOCATION: (1)..(1)
<223> OTHER INFORMATION: wherein a FAM label is attached
<220> FEATURE:
<221> NAME/KEY: misc_feature
<222> LOCATION: (17)..(17)
<223> OTHER INFORMATION: wherein a MGB label is attached

<400> SEQUENCE: 55
accaagaggc tattcaa                                                   17

<210> SEQ ID NO 56
<211> LENGTH: 10
<212> TYPE: PRT
<213> ORGANISM: Artificial
<220> FEATURE:
<223> OTHER INFORMATION: NES motif
<220> FEATURE:
<221> NAME/KEY: MISC_FEATURE
<222> LOCATION: (1)..(1)
<223> OTHER INFORMATION: Xaa is a hydrophobic amino acid selected from
      the group consisting of leucine, isoleucine, methionine, valine,
      and phenylalanine
<220> FEATURE:
<221> NAME/KEY: MISC_FEATURE
<222> LOCATION: (2)..(4)
<223> OTHER INFORMATION: Xaa can be any naturally occuring amino acid
<220> FEATURE:
<221> NAME/KEY: MISC_FEATURE
<222> LOCATION: (5)..(5)
<223> OTHER INFORMATION: Xaa is a hydrophobic amino acid selected from
      the group consisting of leucine, isoleucine, methionine, valine,
      and phenylalanine
<220> FEATURE:
<221> NAME/KEY: MISC_FEATURE
<222> LOCATION: (6)..(7)
<223> OTHER INFORMATION: Xaa can be any naturally occuring amino acid
<220> FEATURE:
<221> NAME/KEY: MISC_FEATURE
<222> LOCATION: (8)..(8)
<223> OTHER INFORMATION: Xaa is a hydrophobic amino acid selected from
      the group consisting of leucine, isoleucine, methionine, valine,
      and phenylalanine
<220> FEATURE:
<221> NAME/KEY: MISC_FEATURE
<222> LOCATION: (9)..(9)
<223> OTHER INFORMATION: Xaa can be any naturally occuring amino acid
<220> FEATURE:
<221> NAME/KEY: MISC_FEATURE
<222> LOCATION: (10)..(10)
<223> OTHER INFORMATION: Xaa is a hydrophobic amino acid

<400> SEQUENCE: 56

```
Xaa Xaa Xaa Xaa Xaa Xaa Xaa Xaa Xaa Xaa
1               5                   10
```

```
<210> SEQ ID NO 57
<211> LENGTH: 42
<212> TYPE: DNA
<213> ORGANISM: Artificial
<220> FEATURE:
<223> OTHER INFORMATION: Mutated C-terminal NPM sequence

<400> SEQUENCE: 57
gatctctgtc tggcagtgga ggaagtctct ttaagaaaat ag        42

<210> SEQ ID NO 58
<211> LENGTH: 7
<212> TYPE: PRT
<213> ORGANISM: Artificial
<220> FEATURE:
<223> OTHER INFORMATION: C-terminal NPM sequence

<400> SEQUENCE: 58

Trp Gln Trp Arg Lys Ser Leu
1               5

<210> SEQ ID NO 59
<211> LENGTH: 11
<212> TYPE: PRT
<213> ORGANISM: Artificial
<220> FEATURE:
<223> OTHER INFORMATION: Mutated C-terminal NPM sequence

<400> SEQUENCE: 59

Cys Leu Ala Val Glu Glu Val Ser Leu Arg Lys
1               5                   10

<210> SEQ ID NO 60
<211> LENGTH: 41
<212> TYPE: DNA
<213> ORGANISM: Artificial
<220> FEATURE:
<223> OTHER INFORMATION: Mutated C-terminal NPM sequence

<400> SEQUENCE: 60
gatctctgca tggcagtgga ggaagtctct taagaaaata g         41

<210> SEQ ID NO 61
<211> LENGTH: 42
<212> TYPE: DNA
<213> ORGANISM: Artificial
<220> FEATURE:
<223> OTHER INFORMATION: Mutated C-terminal NPM sequence

<400> SEQUENCE: 61
gatctctgcg tggcagtgga ggaagtctct ttaagaaaat ag        42

<210> SEQ ID NO 62
<211> LENGTH: 42
<212> TYPE: DNA
<213> ORGANISM: Artificial
<220> FEATURE:
<223> OTHER INFORMATION: Mutated C-terminal NPM sequence

<400> SEQUENCE: 62
gatctctgcc tggcagtgga ggaagtctct ttaagaaaat ag        42

<210> SEQ ID NO 63
```

```
<211> LENGTH: 42
<212> TYPE: DNA
<213> ORGANISM: Artificial
<220> FEATURE:
<223> OTHER INFORMATION: Mutated C-terminal NPM sequence

<400> SEQUENCE: 63
gatctctggc agtctcttgc ccaagtctct ttaagaaaat ag                         42

<210> SEQ ID NO 64
<211> LENGTH: 42
<212> TYPE: DNA
<213> ORGANISM: Artificial
<220> FEATURE:
<223> OTHER INFORMATION: Mutated C-terminal NPM sequence

<400> SEQUENCE: 64
gatctctggc agtccctgga gaaagtctct ttaagaaaat ag                         42

<210> SEQ ID NO 65
<211> LENGTH: 27
<212> TYPE: DNA
<213> ORGANISM: Artificial
<220> FEATURE:
<223> OTHER INFORMATION: Primer NPM forward mut A-D

<400> SEQUENCE: 65
cgccacgcta gcgaagattc gatggac                                          27

<210> SEQ ID NO 66
<211> LENGTH: 58
<212> TYPE: DNA
<213> ORGANISM: Artificial
<220> FEATURE:
<223> OTHER INFORMATION: Primer NPM reverse mut A

<400> SEQUENCE: 66
ctattttctt aaagagactt cctccactgc cagacagaga tcttgaatag cctcttgg        58

<210> SEQ ID NO 67
<211> LENGTH: 58
<212> TYPE: DNA
<213> ORGANISM: Artificial
<220> FEATURE:
<223> OTHER INFORMATION: Primer NPM reverse mut B

<400> SEQUENCE: 67
ctattttctt aaagagactt cctccactgc catgcagaga tcttgaatag cctcttgg        58

<210> SEQ ID NO 68
<211> LENGTH: 58
<212> TYPE: DNA
<213> ORGANISM: Artificial
<220> FEATURE:
<223> OTHER INFORMATION: Primer NPM reverse mut C

<400> SEQUENCE: 68
ctattttctt aaagagactt cctccactgc cacgcagaga tcttgaatag cctcttgg        58

<210> SEQ ID NO 69
<211> LENGTH: 58
<212> TYPE: DNA
<213> ORGANISM: Artificial
<220> FEATURE:
<223> OTHER INFORMATION: Primer NPM reverse mut D

<400> SEQUENCE: 69
```
ctattttctt aaagagactt cctccactgc caggcagaga tcttgaatag cctcttgg    58

<210> SEQ ID NO 70
<211> LENGTH: 27
<212> TYPE: DNA
<213> ORGANISM: Artificial
<220> FEATURE:
<223> OTHER INFORMATION: Primer NPM reverse

<400> SEQUENCE: 70
tcaagaattc cagaaatgaa ataagac                                      27

<210> SEQ ID NO 71
<211> LENGTH: 35
<212> TYPE: DNA
<213> ORGANISM: Artificial
<220> FEATURE:
<223> OTHER INFORMATION: Primer NPM mut E

<400> SEQUENCE: 71
gatctctggc agtctcttgc ccaagtctct ttaag                             35

<210> SEQ ID NO 72
<211> LENGTH: 35
<212> TYPE: DNA
<213> ORGANISM: Artificial
<220> FEATURE:
<223> OTHER INFORMATION: Primer NPM mut G

<400> SEQUENCE: 72
gatctctggc agtgcttcgc ccaagtctct ttaag                             35

<210> SEQ ID NO 73
<211> LENGTH: 35
<212> TYPE: DNA
<213> ORGANISM: Artificial
<220> FEATURE:
<223> OTHER INFORMATION: Primer NPM mut R

<400> SEQUENCE: 73
gatctctggc agaggatgga ggaagtctct ttaag                             35

<210> SEQ ID NO 74
<211> LENGTH: 43
<212> TYPE: DNA
<213> ORGANISM: Artificial
<220> FEATURE:
<223> OTHER INFORMATION: Primer NPM forward mut A A290W

<400> SEQUENCE: 74
gatctctgtc tgtgggtgga ggaagtctct ttaagaaaat agg                    43

<210> SEQ ID NO 75
<211> LENGTH: 43
<212> TYPE: DNA
<213> ORGANISM: Artificial
<220> FEATURE:
<223> OTHER INFORMATION: Primer NPM reverse mut A A290W

<400> SEQUENCE: 75
aattcctatt ttcttaaaga gacttcctcc acccacagac aga                    43

<210> SEQ ID NO 76
<211> LENGTH: 43
<212> TYPE: DNA
<213> ORGANISM: Artificial
<220> FEATURE:

<223> OTHER INFORMATION: Primer NPM forward mut A C288W and A290W

<400> SEQUENCE: 76
gatctctggc tgtgggtgga ggaagtctct ttaagaaaat agg          43

<210> SEQ ID NO 77
<211> LENGTH: 43
<212> TYPE: DNA
<213> ORGANISM: Artificial
<220> FEATURE:
<223> OTHER INFORMATION: Primer NPM reverse mut A C288W and A290W

<400> SEQUENCE: 77
aattcctatt ttcttaaaga gacttcctcc acccacagcc aga          43

<210> SEQ ID NO 78
<211> LENGTH: 43
<212> TYPE: DNA
<213> ORGANISM: Artificial
<220> FEATURE:
<223> OTHER INFORMATION: Primer NPM forward mut A No NES

<400> SEQUENCE: 78
gatctctgtg gagcagggga ggaaggctct ttaagaaaat agg          43

<210> SEQ ID NO 79
<211> LENGTH: 43
<212> TYPE: DNA
<213> ORGANISM: Artificial
<220> FEATURE:
<223> OTHER INFORMATION: Primer NPM reverse mut A No NES

<400> SEQUENCE: 79
aattcctatt ttcttaaaga gccttcctcc cctgctccac aga          43

<210> SEQ ID NO 80
<211> LENGTH: 14
<212> TYPE: PRT
<213> ORGANISM: Artificial
<220> FEATURE:
<223> OTHER INFORMATION: NES motif
<220> FEATURE:
<221> NAME/KEY: MISC_FEATURE
<222> LOCATION: (2)..(4)
<223> OTHER INFORMATION: Xaa can be any naturally occuring amino acid
<220> FEATURE:
<221> NAME/KEY: MISC_FEATURE
<222> LOCATION: (6)..(8)
<223> OTHER INFORMATION: Xaa can be any naturally occuring amino acid

<400> SEQUENCE: 80

Leu Xaa Xaa Xaa Phe Xaa Xaa Xaa Leu Phe Lys Lys Ile Val
1               5                   10

<210> SEQ ID NO 81
<211> LENGTH: 9
<212> TYPE: PRT
<213> ORGANISM: Artificial
<220> FEATURE:
<223> OTHER INFORMATION: NES motif
<220> FEATURE:
<221> NAME/KEY: MISC_FEATURE
<222> LOCATION: (2)..(3)
<223> OTHER INFORMATION: Xaa can be any naturally occuring amino acid
<220> FEATURE:
<221> NAME/KEY: MISC_FEATURE
<222> LOCATION: (5)..(6)
<223> OTHER INFORMATION: Xaa can be any naturally occuring amino acid
<220> FEATURE:
<221> NAME/KEY: MISC_FEATURE

```
<222> LOCATION: (8)..(8)
<223> OTHER INFORMATION: Xaa can be any naturally occuring amino acid

<400> SEQUENCE: 81

Leu Xaa Xaa Pro Xaa Xaa Leu Xaa Leu
1               5

<210> SEQ ID NO 82
<211> LENGTH: 21
<212> TYPE: DNA
<213> ORGANISM: Artificial
<220> FEATURE:
<223> OTHER INFORMATION: Primer NPM forward

<400> SEQUENCE: 82
ttaactctct ggtggtagaa t                                           21

<210> SEQ ID NO 83
<211> LENGTH: 20
<212> TYPE: DNA
<213> ORGANISM: Artificial
<220> FEATURE:
<223> OTHER INFORMATION: Primer NPM reverse

<400> SEQUENCE: 83
gagtatttgc cattcctaac                                             20

<210> SEQ ID NO 84
<211> LENGTH: 38
<212> TYPE: DNA
<213> ORGANISM: Homo sapiens

<400> SEQUENCE: 84
gatctctggc agtggaggaa gtctctttaa gaaaatag                         38

<210> SEQ ID NO 85
<211> LENGTH: 9
<212> TYPE: PRT
<213> ORGANISM: Homo sapiens

<400> SEQUENCE: 85

Asp Leu Trp Gln Trp Arg Lys Ser Leu
1               5

<210> SEQ ID NO 86
<211> LENGTH: 56
<212> TYPE: DNA
<213> ORGANISM: Homo sapiens

<400> SEQUENCE: 86
gaccaagagg ctattcaaga tctctggcag tggaggaagt ctctttaaga aaatag     56

<210> SEQ ID NO 87
<211> LENGTH: 60
<212> TYPE: DNA
<213> ORGANISM: Homo sapiens

<400> SEQUENCE: 87
gaccaagagg ctattcaaga tctctgtctg gcagtggagg aagtctcttt aagaaaatag 60

<210> SEQ ID NO 88
<211> LENGTH: 60
<212> TYPE: DNA
<213> ORGANISM: Homo sapiens

<400> SEQUENCE: 88
```
gaccaagagg ctattcaaga tctctgcatg gcagtggagg aagtctcttt aagaaaatag    60

<210> SEQ ID NO 89
<211> LENGTH: 60
<212> TYPE: DNA
<213> ORGANISM: Homo sapiens

<400> SEQUENCE: 89
gaccaagagg ctattcaaga tctctgcgtg gcagtggagg aagtctcttt aagaaaatag    60

<210> SEQ ID NO 90
<211> LENGTH: 60
<212> TYPE: DNA
<213> ORGANISM: Homo sapiens

<400> SEQUENCE: 90
gaccaagagg ctattcaaga tctctgcctg gcagtggagg aagtctcttt aagaaaatag    60

<210> SEQ ID NO 91
<211> LENGTH: 60
<212> TYPE: DNA
<213> ORGANISM: Homo sapiens

<400> SEQUENCE: 91
gaccaagagg ctattcaaga tctctggcag tctcttgccc aagtctcttt aagaaaatag    60

<210> SEQ ID NO 92
<211> LENGTH: 60
<212> TYPE: DNA
<213> ORGANISM: Homo sapiens

<400> SEQUENCE: 92
gaccaagagg ctattcaaga tctctggcag tccctggaga aagtctcttt aagaaaatag    60

<210> SEQ ID NO 93
<211> LENGTH: 60
<212> TYPE: DNA
<213> ORGANISM: Homo sapiens

<400> SEQUENCE: 93
gaccaagagg ctattcaaga tctctggcag tgcttcgccc aagtctcttt aagaaaatag    60

<210> SEQ ID NO 94
<211> LENGTH: 60
<212> TYPE: DNA
<213> ORGANISM: Homo sapiens

<400> SEQUENCE: 94
gaccaagagg ctattcaaga tctctggcag tgttttcaa aagtctcttt aagaaaatag    60

<210> SEQ ID NO 95
<211> LENGTH: 60
<212> TYPE: DNA
<213> ORGANISM: Homo sapiens

<400> SEQUENCE: 95
gaccaagagg ctattcaaga tctctggcag tccctcgccc aagtctcttt aagaaaatag    60

<210> SEQ ID NO 96
<211> LENGTH: 60
<212> TYPE: DNA
<213> ORGANISM: Homo sapiens

<400> SEQUENCE: 96

```
gaccaagagg ctattcaaga tctctggcag tctctttcta aagtctcttt aagaaaatag    60
```

<210> SEQ ID NO 97
<211> LENGTH: 55
<212> TYPE: DNA
<213> ORGANISM: Homo sapiens

<400> SEQUENCE: 97

```
gaccaagagg ctattcaaga tctctcccgg gcagtaagtc tctttaagaa aatag    55
```

<210> SEQ ID NO 98
<211> LENGTH: 60
<212> TYPE: DNA
<213> ORGANISM: Homo sapiens

<400> SEQUENCE: 98

```
gaccaagagg ctattcaaga tctctggcag tcccttccca aagtctcttt aagaaaatag    60
```

<210> SEQ ID NO 99
<211> LENGTH: 60
<212> TYPE: DNA
<213> ORGANISM: Homo sapiens

<400> SEQUENCE: 99

```
gaccaagagg ctattcaaga tctctgtagc gcagtggagg aagtctcttt aagaaaatag    60
```

<210> SEQ ID NO 100
<211> LENGTH: 60
<212> TYPE: DNA
<213> ORGANISM: Homo sapiens

<400> SEQUENCE: 100

```
gaccaagagg ctattcaaga tctctcccag gcagtggagg aagtctcttt aagaaaatag    60
```

<210> SEQ ID NO 101
<211> LENGTH: 60
<212> TYPE: DNA
<213> ORGANISM: Homo sapiens

<400> SEQUENCE: 101

```
gaccaagagg ctattcaaga tctctgccac gcagtggagg aagtctcttt aagaaaatag    60
```

<210> SEQ ID NO 102
<211> LENGTH: 62
<212> TYPE: DNA
<213> ORGANISM: Homo sapiens

<400> SEQUENCE: 102

```
gaccaagagg ctattcaaga tctctggcag cgtttccgga ggaagtctct ttaagaaaat    60
ag                                                                  62
```

<210> SEQ ID NO 103
<211> LENGTH: 60
<212> TYPE: DNA
<213> ORGANISM: Homo sapiens

<400> SEQUENCE: 103

```
gaccaagagg ctattcaaga tctctgtacc ttcctggagg aagtctcttt aagaaaatag    60
```

<210> SEQ ID NO 104
<211> LENGTH: 60
<212> TYPE: DNA
<213> ORGANISM: Homo sapiens

```
<400> SEQUENCE: 104
gaccaagagg ctattcaaga tctctggcag aggatggagg aagtctcttt aagaaaatag        60

<210> SEQ ID NO 105
<211> LENGTH: 60
<212> TYPE: DNA
<213> ORGANISM: Homo sapiens

<400> SEQUENCE: 105
gaccaagagg ctattcaaga tctctgcagg gcagtggagg aagtctcttt aagaaaatag        60

<210> SEQ ID NO 106
<211> LENGTH: 60
<212> TYPE: DNA
<213> ORGANISM: Homo sapiens

<400> SEQUENCE: 106
gaccaagagg ctattcaaga tctctgccgg gcagtggagg aagtctcttt aagaaaatag        60

<210> SEQ ID NO 107
<211> LENGTH: 60
<212> TYPE: DNA
<213> ORGANISM: Homo sapiens

<400> SEQUENCE: 107
gaccaagagg ctattcaaga tctctgccgc ggagtggagg aagtctcttt aagaaaatag        60

<210> SEQ ID NO 108
<211> LENGTH: 60
<212> TYPE: DNA
<213> ORGANISM: Homo sapiens

<400> SEQUENCE: 108
gaccaagagg ctattcaaga tctctgccag gcagtggagg aagtctcttt aagaaaatag        60

<210> SEQ ID NO 109
<211> LENGTH: 60
<212> TYPE: DNA
<213> ORGANISM: Homo sapiens

<400> SEQUENCE: 109
gaccaagagg ctattcaaga tctctgtttg gcagtggagg aagtctcttt aagaaaatag        60

<210> SEQ ID NO 110
<211> LENGTH: 60
<212> TYPE: DNA
<213> ORGANISM: Homo sapiens

<400> SEQUENCE: 110
gaccaagagg ctattcaaga tctctgtcgg gcagtggagg aagtctcttt aagaaaatag        60

<210> SEQ ID NO 111
<211> LENGTH: 60
<212> TYPE: DNA
<213> ORGANISM: Homo sapiens

<400> SEQUENCE: 111
gaccaagagg ctattcaaga tctctggcag tccatggagg aagtctcttt aagaaaatag        60

<210> SEQ ID NO 112
<211> LENGTH: 60
<212> TYPE: DNA
<213> ORGANISM: Homo sapiens
```

<400> SEQUENCE: 112
gaccaagagg ctattcaaga tctctgtcat gcagtggagg aagtctcttt aagaaaatag    60

<210> SEQ ID NO 113
<211> LENGTH: 60
<212> TYPE: DNA
<213> ORGANISM: Homo sapiens

<400> SEQUENCE: 113
gaccaagagg ctattcaaga tctctgcttg gcagtggagg aagtctcttt aagaaaatag    60

<210> SEQ ID NO 114
<211> LENGTH: 61
<212> TYPE: DNA
<213> ORGANISM: Homo sapiens

<400> SEQUENCE: 114
gaccaagagg ctattcaaga tctctggcaa gatttcttaa atcgtctctt taagaaaata    60
g                                                                    61

<210> SEQ ID NO 115
<211> LENGTH: 59
<212> TYPE: DNA
<213> ORGANISM: Homo sapiens

<400> SEQUENCE: 115
accaagaggc tattcaagat ctctatgcgg cagtggagga agtctcttta agaaaatag     59

<210> SEQ ID NO 116
<211> LENGTH: 60
<212> TYPE: DNA
<213> ORGANISM: Homo sapiens

<400> SEQUENCE: 116
gaccaagagg ctattcaaga tctctggccc gcagtggagg aagtctcttt aagaaaatag    60

<210> SEQ ID NO 117
<211> LENGTH: 60
<212> TYPE: DNA
<213> ORGANISM: Homo sapiens

<400> SEQUENCE: 117
gaccaagagg ctattcaaga tctctgtaag gcagtggagg aagtctcttt aagaaaatag    60

<210> SEQ ID NO 118
<211> LENGTH: 60
<212> TYPE: DNA
<213> ORGANISM: Homo sapiens

<400> SEQUENCE: 118
gaccaagagg ctattcaaga tctctggcag tgctgctccc aagtctcttt aagaaaatag    60

<210> SEQ ID NO 119
<211> LENGTH: 60
<212> TYPE: DNA
<213> ORGANISM: Homo sapiens

<400> SEQUENCE: 119
gaccaagagg ctattcaaga tctctggcag ttattttccc aagtctcttt aagaaaatag    60

<210> SEQ ID NO 120
<211> LENGTH: 60

```
<212> TYPE: DNA
<213> ORGANISM: Homo sapiens

<400> SEQUENCE: 120
gaccaagagg ctattcaaga tctctgtttg gcagtggagg aagtctcttt aagaaaatag    60

<210> SEQ ID NO 121
<211> LENGTH: 60
<212> TYPE: DNA
<213> ORGANISM: Homo sapiens

<400> SEQUENCE: 121
gaccaagagg ctattcaaga tctctgcttg gcagtggagg aagtctcttt aagaaaatag    60

<210> SEQ ID NO 122
<211> LENGTH: 60
<212> TYPE: DNA
<213> ORGANISM: Homo sapiens

<400> SEQUENCE: 122
gaccaagagg ctattcaaga tctctgtaag gcagtggagg aagtctcttt aagaaaatag    60

<210> SEQ ID NO 123
<211> LENGTH: 60
<212> TYPE: DNA
<213> ORGANISM: Homo sapiens

<400> SEQUENCE: 123
gaccaagagg ctattcaaga tctctgtatg gcagtggagg aagtctcttt aagaaaatag    60

<210> SEQ ID NO 124
<211> LENGTH: 60
<212> TYPE: DNA
<213> ORGANISM: Homo sapiens

<400> SEQUENCE: 124
gaccaagagg ctattcaaga tctctgcaga gcagtggagg aagtctcttt aagaaaatag    60

<210> SEQ ID NO 125
<211> LENGTH: 13
<212> TYPE: PRT
<213> ORGANISM: Homo sapiens

<400> SEQUENCE: 125

Asp Leu Trp Gln Cys Phe Ala Gln Val Ser Leu Arg Lys
1               5                   10

<210> SEQ ID NO 126
<211> LENGTH: 13
<212> TYPE: PRT
<213> ORGANISM: Homo sapiens

<400> SEQUENCE: 126

Asp Leu Trp Gln Cys Phe Ser Lys Val Ser Leu Arg Lys
1               5                   10

<210> SEQ ID NO 127
<211> LENGTH: 13
<212> TYPE: PRT
<213> ORGANISM: Homo sapiens

<400> SEQUENCE: 127

Asp Leu Trp Gln Ser Leu Ser Lys Val Ser Leu Arg Lys
1               5                   10
```

```
<210> SEQ ID NO 128
<211> LENGTH: 13
<212> TYPE: PRT
<213> ORGANISM: Homo sapiens

<400> SEQUENCE: 128

Asp Leu Ser Arg Ala Val Glu Glu Val Ser Leu Arg Lys
1               5                   10

<210> SEQ ID NO 129
<211> LENGTH: 13
<212> TYPE: PRT
<213> ORGANISM: Homo sapiens

<400> SEQUENCE: 129

Asp Leu Cys Thr Ala Val Glu Glu Val Ser Leu Arg Lys
1               5                   10

<210> SEQ ID NO 130
<211> LENGTH: 13
<212> TYPE: PRT
<213> ORGANISM: Homo sapiens

<400> SEQUENCE: 130

Asp Leu Ser Gln Ala Val Glu Glu Val Ser Leu Arg Lys
1               5                   10

<210> SEQ ID NO 131
<211> LENGTH: 13
<212> TYPE: PRT
<213> ORGANISM: Homo sapiens

<400> SEQUENCE: 131

Asp Leu Cys His Ala Val Glu Glu Val Ser Leu Arg Lys
1               5                   10

<210> SEQ ID NO 132
<211> LENGTH: 13
<212> TYPE: PRT
<213> ORGANISM: Homo sapiens

<400> SEQUENCE: 132

Asp Leu Trp Gln Arg Phe Gln Glu Val Ser Leu Arg Lys
1               5                   10

<210> SEQ ID NO 133
<211> LENGTH: 13
<212> TYPE: PRT
<213> ORGANISM: Homo sapiens

<400> SEQUENCE: 133

Asp Leu Cys Thr Phe Leu Glu Glu Val Ser Leu Arg Lys
1               5                   10

<210> SEQ ID NO 134
<211> LENGTH: 13
<212> TYPE: PRT
<213> ORGANISM: Homo sapiens

<400> SEQUENCE: 134

Asp Leu Trp Gln Arg Met Glu Glu Val Ser Leu Arg Lys
1               5                   10

<210> SEQ ID NO 135
<211> LENGTH: 13
```

```
<212> TYPE: PRT
<213> ORGANISM: Homo sapiens

<400> SEQUENCE: 135

Asp Leu Cys Arg Ala Val Glu Glu Val Ser Leu Arg Lys
1               5                   10

<210> SEQ ID NO 136
<211> LENGTH: 13
<212> TYPE: PRT
<213> ORGANISM: Homo sapiens

<400> SEQUENCE: 136

Asp Leu Cys Arg Gly Val Glu Glu Val Ser Leu Arg Lys
1               5                   10

<210> SEQ ID NO 137
<211> LENGTH: 13
<212> TYPE: PRT
<213> ORGANISM: Homo sapiens

<400> SEQUENCE: 137

Asp Leu Cys Gln Ala Val Glu Glu Val Ser Leu Arg Lys
1               5                   10

<210> SEQ ID NO 138
<211> LENGTH: 13
<212> TYPE: PRT
<213> ORGANISM: Homo sapiens

<400> SEQUENCE: 138

Asp Leu Trp Gln Ser Met Glu Glu Val Ser Leu Arg Lys
1               5                   10

<210> SEQ ID NO 139
<211> LENGTH: 15
<212> TYPE: PRT
<213> ORGANISM: Homo sapiens

<400> SEQUENCE: 139

Asp Leu Trp Gln Asp Phe Leu Asn Arg Leu Phe Lys Lys Ile Val
1               5                   10                  15

<210> SEQ ID NO 140
<211> LENGTH: 13
<212> TYPE: PRT
<213> ORGANISM: Homo sapiens

<400> SEQUENCE: 140

Asp Leu Cys Ala Ala Val Glu Glu Val Ser Leu Arg Lys
1               5                   10

<210> SEQ ID NO 141
<211> LENGTH: 13
<212> TYPE: PRT
<213> ORGANISM: Homo sapiens

<400> SEQUENCE: 141

Asp Leu Cys Lys Ala Val Glu Glu Val Ser Leu Arg Lys
1               5                   10

<210> SEQ ID NO 142
<211> LENGTH: 13
<212> TYPE: PRT
<213> ORGANISM: Homo sapiens
```

<400> SEQUENCE: 142

Asp Leu Trp Gln Cys Cys Ser Gln Val Ser Leu Arg Lys
1               5                   10